US008565501B2

(12) United States Patent
Asaka

(10) Patent No.: US 8,565,501 B2
(45) Date of Patent: Oct. 22, 2013

(54) BIOLOGICAL LIGHT MEASUREMENT DEVICE AND POSITION DISPLAY METHOD OF LIGHT IRRADIATION POSITION AND LIGHT DETECTION POSITION OR MEASUREMENT CHANNEL

(75) Inventor: Hirokazu Asaka, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 385 days.

(21) Appl. No.: 13/121,309

(22) PCT Filed: Sep. 30, 2009

(86) PCT No.: PCT/JP2009/067023
§ 371 (c)(1),
(2), (4) Date: Mar. 28, 2011

(87) PCT Pub. No.: WO2010/038774
PCT Pub. Date: Apr. 8, 2010

(65) Prior Publication Data
US 2011/0176713 A1    Jul. 21, 2011

(30) Foreign Application Priority Data
Oct. 1, 2008   (JP) .................................. 2008-256510

(51) Int. Cl.
*G06K 9/00*    (2006.01)
(52) U.S. Cl.
USPC ............................ 382/128; 600/310; 600/473
(58) Field of Classification Search
USPC ................................... 382/128; 600/310, 473
See application file for complete search history.

(56) References Cited

U.S. PATENT DOCUMENTS

| 5,803,909 | A | * | 9/1998 | Maki et al. ...................... 600/310 |
| 6,128,517 | A | * | 10/2000 | Maki et al. ...................... 600/310 |

(Continued)

FOREIGN PATENT DOCUMENTS

| JP | 09-019408 | | 1/1997 |
| JP | 2001-079008 | | 3/2001 |
| JP | 2003-088528 | * | 3/2003 |

OTHER PUBLICATIONS

Obrig et al., "Beyond the Visible—Imaging the Human Brain With Light", 2003, J Cereb Blood Flow Metab, 23(1), 1-18.*

(Continued)

*Primary Examiner* — David Zarka
*Assistant Examiner* — Katrina Fujita
(74) *Attorney, Agent, or Firm* — Antonelli, Terry, Stout & Kraus, LLP.

(57) ABSTRACT

There is provided a biological light measurement device capable of simply displaying a light irradiation position and a light detection position or a three-dimensional position of a measurement channel without measuring the light irradiation position and the light detection position or the three-dimensional position of the measurement channel. The biological light measurement device includes a display unit, which displays a two-dimensional head image selected from the data regarding the head shape and a two-dimensional probe, and a control unit that has a coordinate transformation section, which performs coordinate transformation of the positional information regarding the two-dimensional probe set on the displayed two-dimensional head image and calculates the light irradiation position and the light detection position or the position of the measurement channel on a three-dimensional head image.

11 Claims, 38 Drawing Sheets

(56) References Cited

U.S. PATENT DOCUMENTS

| | | | |
|---|---|---|---|
| 6,240,309 B1* | 5/2001 | Yamashita et al. | 600/407 |
| 6,282,438 B1* | 8/2001 | Maki et al. | 600/476 |
| 6,542,763 B1* | 4/2003 | Yamashita et al. | 600/310 |
| 6,901,284 B1* | 5/2005 | Maki et al. | 600/476 |
| 7,047,149 B1* | 5/2006 | Maki et al. | 702/150 |
| 7,228,166 B1* | 6/2007 | Kawasaki et al. | 600/476 |
| 7,233,819 B2* | 6/2007 | Eda et al. | 600/411 |
| 7,613,502 B2* | 11/2009 | Yamamoto et al. | 600/473 |
| 8,180,426 B2* | 5/2012 | Dan et al. | 600/407 |
| 8,235,894 B2* | 8/2012 | Nakagawa | 600/300 |
| 8,406,838 B2* | 3/2013 | Kato | 600/322 |
| 2001/0018554 A1* | 8/2001 | Yamashita et al. | 600/178 |
| 2001/0047131 A1* | 11/2001 | Maki et al. | 600/407 |
| 2004/0127784 A1* | 7/2004 | Yamashita et al. | 600/407 |
| 2005/0131303 A1* | 6/2005 | Maki et al. | 600/473 |
| 2005/0148857 A1* | 7/2005 | Maki et al. | 600/407 |
| 2005/0171440 A1* | 8/2005 | Maki et al. | 600/476 |
| 2006/0184045 A1* | 8/2006 | Yamashita et al. | 600/476 |
| 2006/0184046 A1* | 8/2006 | Yamashita et al. | 600/476 |
| 2006/0184047 A1* | 8/2006 | Yamashita et al. | 600/476 |
| 2007/0073179 A1* | 3/2007 | Afonso et al. | 600/523 |

OTHER PUBLICATIONS

Machine Translation of JP 2003-088528.*

* cited by examiner

THREE-DIMENSIONAL SEMI-ELLIPSOIDAL SURFACE

COORDINATE TRANSFORMATION PROCESSING C

THREE-DIMENSIONAL HEMISPHERICAL SURFACE

HEAD SHAPE IMAGE

THREE-DIMENSIONAL SEMI-ELLIPSOIDAL SURFACE

COORDINATE TRANSFORMATION PROCESSING D

THREE-DIMENSIONAL SEMI-ELLIPSOIDAL SURFACE

THREE-DIMENSIONAL SEMI-ELLIPSOIDAL SURFACE

THREE-DIMENSIONAL SEMI-ELLIPSOIDAL SURFACE

THREE-DIMENSIONAL SEMI-ELLIPSOIDAL SURFACE

● CENTRAL POSITION OF PROBE
○ LIGHT IRRADIATION POSITION
□ LIGHT DETECTION POSITION

BIOLOGICAL LIGHT MEASUREMENT DEVICE AND POSITION DISPLAY METHOD OF LIGHT IRRADIATION POSITION AND LIGHT DETECTION POSITION OR MEASUREMENT CHANNEL

TECHNICAL FIELD

The present invention relates to a biological light measurement device and a position display method of a light irradiation position and a light detection position or a measurement channel and in particular, to a biological light measurement device which measures blood circulation, a blood motion state, and a change in the amount of hemoglobin inside the body by irradiating near-infrared light to the body and measuring the light, which is transmitted through the inside of the body or reflected in the body, and a position display method of a light irradiation position and a light detection position or a measurement channel.

BACKGROUND ART

The biological light measurement device is a device capable of easily measuring blood circulation, a blood moving state, and a change in the amount of hemoglobin inside the body with low restraint and without doing damage to the subject body. In recent years, imaging of the measurement data using a multi-channel device has been realized, and its clinical application is expected.

A device that irradiates visible-wavelength to near-infrared-wavelength light to the body and measures the inside of the body from the reflected light at the position distant by about 10 to 50 mm from the irradiation position, as a principle of the biological light measurement device, is known. Moreover, in biological light measurement devices using a multi-channel, a device with a function of easily displaying and setting the positional relationship between a measured part in an object to be measured and a light irradiation position and a light detection position on two dimensions is also known.

Patent Document 1 discloses a biological light measurement device with a function of measuring a light irradiation position and a light detection position and displaying a body transmitted light intensity image, which is corrected on the basis of the measured light irradiation position and light detection position, and a shape image of an object to be measured as an indication of a measured part so as to overlap each other, in order to clarify the three-dimensional positional relationship among the measured parts in the object to be measured, the light irradiation position and the light detection position, and the body transmitted light intensity image. As a shape image of an object to be measured, a wireframe image, a tomographic image, a CT image, and an MRI image of the object to be measured may be mentioned.

RELATED ART DOCUMENT

Citation List

Patent Document 1: JP-A-2001-79008

SUMMARY OF INVENTION

Technical Problem

In the known document described above, there is a problem in that a light irradiation position and a light detection position should be measured.

Measuring the light irradiation position and the light detection position necessarily results in a cost increase because a measuring person has to use a device having the measurement means.

In addition, the work itself of measuring the light irradiation position and the light detection position at the time of biological light measurement requires time and effort. This causes a burden on the measuring person and the subject body. In particular, since a large number of channels are used in normal biological light measurement, the number of light irradiation positions and light detection positions that should be measured is also increased. This causes a big burden.

On the other hand, for a shape image of the object to be measured, there is a need to roughly detect a light irradiation position and a light detection position and display them so as to overlap each other. For example, this is a case where a measured part is mostly fixed at specific positions, such as the frontal and occipital regions, from the experience of biological light measurements in the past and accordingly, detailed positional information is not needed.

For this need, a measurement result of accurate three-dimensional positions of a light irradiation position and a light detection position or a measurement channel is superfluous information, and the above-described cost and burden are an excessive burden compared with the purpose.

It is an object of the present invention to provide a biological light measurement device that makes it possible to display a light irradiation position and a light detection position on a three-dimensional head image or a calculation position of a measurement channel without actually measuring the light irradiation position and the light detection position or the three-dimensional position of the measurement channel.

Solution to Problem

In order to solve the above-described problems, the present invention is configured as follows. A biological light measurement device of the present invention is a biological light measurement device including a light source unit that irradiates near-infrared light, a two-dimensional probe that measures a transmitted light intensity of the near-infrared light at two-dimensional measurement points of a subject body and outputs a signal corresponding to the transmitted light intensity at each measurement point as measurement data for every measurement channel, a signal processing unit that processes the measurement data of the two-dimensional probe to be imaged, and a display unit that displays the imaged measurement data, and is characterized in that it includes: a storage unit that stores data regarding the head shape for display; and a control unit having a coordinate transformation section which performs coordinate transformation of positional information of the two-dimensional probe, which is set on a two-dimensional head image selected from the data regarding the head shape, in order to calculate a light irradiation position and a light detection position on a three-dimensional head image or the position of the measurement channel.

As described above, according to the present invention, it becomes possible to display a light irradiation position and a light detection position or a position of a measurement channel on a three-dimensional head image without measuring the three-dimensional positions of the light irradiation position and the light detection position by a measuring person.

DESCRIPTION OF EMBODIMENTS

According to a representative embodiment of the present invention, a biological light measurement device includes a probe position easy-input unit. A measuring person sets a light irradiation position and a, light detection position on a head image displayed in a two-dimensional manner, and a control unit calculates three-dimensional light irradiation position and light detection position according to the set information. Accordingly, it becomes possible to display a body transmitted light intensity image and a shape image of an object to be measured as an indication of a measured part so as to overlap each other on a three-dimensional image without measuring the three-dimensional positions of a light irradiation position and a light detection position.

Hereinafter, an overall device configuration, a specific configuration example, and the like of the biological light measurement device of the present invention will be described with reference to the drawings.

(Device Configuration)

Figure 1:
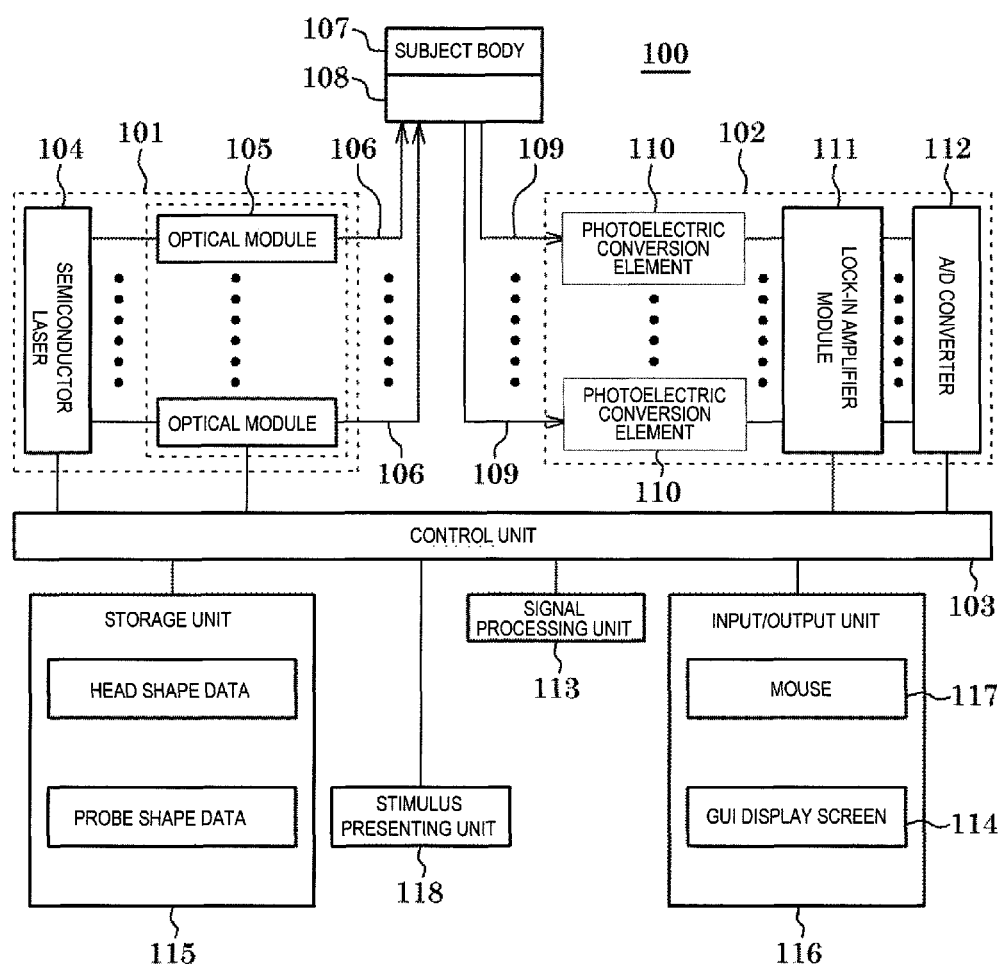
FIG. 1 is a view for explaining the entire configuration of the present invention.

The biological light measurement device of the present invention is a device that irradiates near-infrared light into the body, detects light reflected from the vicinity of the surface of the body or transmitted through the body (hereinafter, simply referred to as transmitted light), and generates an electric signal corresponding to the intensity of the light. As shown in FIG. 1, this biological light measurement device 100 includes a light source unit 101 that irradiates near-infrared light, a light measurement unit 102 that measures transmitted light and converts it into an electric signal, and a control unit 103 that controls driving of the light source unit 101 and the light measurement unit 102.

The light source unit 101 includes a semiconductor laser 104, which emits light with a predetermined wavelength, and a plurality of optical modules 105, which have a modulator for modulating the light generated by the semiconductor laser 104 to have a plurality of different frequencies. Output light of each optical module 105 is irradiated from a predetermined measurement region of a subject body 107, for example, a plurality of places of the head through an optical fiber 106. In addition, a probe holder 108 is fixed to the subject body 107, and the optical fiber 106 and an optical fiber for detection 109 are fixed to the probe holder 108. In the present invention, an approximate midpoint of the light irradiation position of the optical fiber 106 and the light detection position of the optical fiber for detection 109 in the probe holder 108 is defined as a measurement channel.

The probe holder 108 has light irradiation positions and light detection positions, which are arrayed in a square matrix with predetermined distances therebetween according to the head shape of the subject body 107, and calculates a concentration change of oxygenated hemoglobin, a concentration change of deoxygenated hemoglobin, and a change in the total hemoglobin concentration when the brain of the subject body 107 is not stimulated and when the brain is stimulated in the measurement position (measurement channel) which is a middle position of the light irradiation position and the light detection position adjacent to each other.

The light measurement unit 102 includes a photoelectric conversion element 110 such as a photodiode which converts each transmitted light beam, which is guided from a plurality of measurement places of the measurement region through the optical fiber for detection 109, into the amount of electricity corresponding to the amount of light, a lock-in amplifier 111 to which an electric signal from the photoelectric conversion element 110 is input and which selectively detects a modulation signal corresponding to the light irradiation position, and an A/D converter 112 which converts an output signal of the lock-in amplifier 111 into a digital signal.

The light source unit 101 includes "n" optical modules (n is a natural number). Although the wavelength of light depends on the spectral characteristic of an observed matter inside the body, one or a plurality of wavelengths are selected and used from light in a wavelength range of 600 nm to 1400 nm in the case of measuring the oxygen saturation or the amount of blood from the concentration of Hb and $HbO_2$.

The light source unit 101 is configured to generate light beams with two kinds of wavelengths, for example, wavelengths of 780 nm and 830 nm corresponding to two kinds of objects to be measured of oxygenated hemoglobin and deoxygenated hemoglobin, and the light beams with these two wavelengths are mixed and irradiated from one radiation position. The lock-in amplifier 111 selectively detects a modulation signal corresponding to the light irradiation position and these two wavelengths. Hemoglobin amount change signals corresponding to the number of channels, which is twice the number of points (measurement points) between the light irradiation positions and the detection positions, are acquired. In addition, a signal processing unit 113, a storage unit 115, and an input/output unit 116 including a display unit 114 or a mouse 117 are further connected to the control unit 103. In addition, a stimulus presenting unit 118 is provided near the subject body 107 so that a predetermined stimulus generated by the control unit 103 or the like is presented (displayed) on the subject body 107.

The storage unit 115 stores data necessary for processing of the signal processing unit 113 or a processing result. As the data regarding the head shape for display, for example, a plurality of "standard patterns of the head shape" for display corresponding to the age or sex of the subject body 107 is set as a table in a form, in which data of a two-dimensional plane figure and data of a three-dimensional shape (wireframe image) form a pair, and is stored in the storage unit 115. A standard pattern of the head shape or the shape of a probe is prepared beforehand as the positional information enough for a measuring person (user) to understand a specific measured part of a subject body, for example, measurement positions such as the frontal and occipital regions, according to measurement purposes of the subject body 107, on the basis of the past data examples of biological light measurement. Moreover, as the data regarding the head shape for display, data of each shape of a plurality of probe holders provided in the biological light measurement device or data of positional relationship of an optical fiber or an optical fiber for detection in each probe holder is formed as a set and formed as a table as data of a "probe" having a predetermined pattern and is stored in the storage unit 115.

The control unit 103 or the signal processing unit 113 has various kinds of arithmetic processing functions or image processing display functions realized by a CPU, a memory, software, and the like. By the arithmetic processing function, for example, a change signal of the amount of hemoglobin converted into a digital signal is processed. On the basis of the processed information, the signal processing unit 113 generates a graph showing a concentration change of oxygenated hemoglobin, a concentration change of deoxygenated hemoglobin, a change in the total hemoglobin concentration, and the like for every channel or an image obtained by plotting them on the two-dimensional image of the subject body. A processing result of the signal processing unit 113 is displayed on the display unit 114 of the input/output unit 116.

The input/output unit 116 has a function for inputting various instructions required for an operation of the device or outputting a measurement result or a processing result by the measuring person. A display screen of the display unit 114 has a graphical user interface (GUI) function, and it functions as an input unit used when a user inputs instructions required for various kinds of measurements or processing or information, such as the coordinate information, by operating an icon, a "probe" position, and the like on the display screen with the mouse 117 or the like. For example, it is used when a measuring person inputs the information regarding the position coordinates of a probe on the "head shape" by selecting the two-dimensional "head shape" as information equivalent to the position of the probe holder 108 of the subject body 107, that is, the light irradiation position, the light detection position, or the three-dimensional position of a measurement channel with a mouse operation without actually measuring it and setting the two-dimensional position of the "probe" with respect to this "head shape". In addition, it is needless to say that the display unit 114 for the input of two-dimensional position coordinates of the "probe" and a display unit, which displays a processing result of the signal processing unit 113 so as to overlap the position of a head shaped probe, may be separately provided when necessary.

Figure 2:
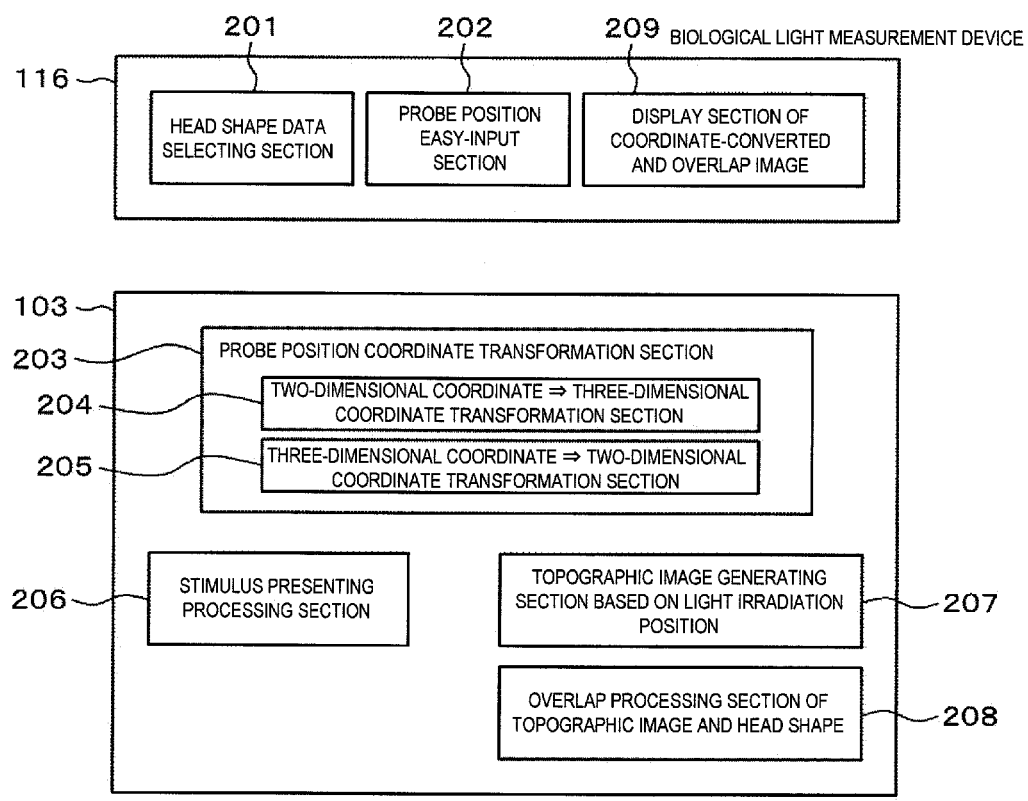
FIG. 2 is a view showing the main functions of a biological light measurement device of the present invention.

FIG. 2 shows a main function of the control unit 103, the display unit 114, or the like in the biological light measurement device 100 of the present invention. The display unit 114 of the biological light measurement device 100 includes: a head shape data selecting section 201 for making a user select a "standard pattern of the head shape" or a "probe", which is optimal for a subject body, from the data of the storage unit 115, such as the "standard head shape"; a probe position easy-input section 202 for generation based on the selected standard pattern of the head shape and the like and for making the user input and set the probe position of the subject body on the screen image of the displayed "head shape"; and a display section 209 that displays a coordinate-converted image, the light irradiation position and the light detection position on the head shape, or an image in which a topographic image overlaps the calculation position of a measurement channel.

The control unit 103 of the biological light measurement device 100 includes: a coordinate transformation section 203 that calculates the light irradiation position and the light detection position or the position of a measurement channel on a three-dimensional head image by performing coordinate transformation processing of the input probe position; a stimulus presenting section 206 that presents a stimulus to the subject body; a topographic image generating section 207 which generates a topographic image on the basis of the light irradiation position; and an overlap processing section 208 that generates a topographic image, on the basis of the input probe position, so as to overlap the light irradiation position and the light detection position on the head shape or the calculation position of a measurement channel. The coordinate transformation section 203 has a function of calculating the light irradiation position and the light detection position on the three-dimensional head image or the position of a measurement channel according to the two-dimensional position information set by the probe position easy-input section 202.

In addition, the coordinate transformation section 203 includes a two-dimensional coordinate to three-dimensional coordinate transformation section 204, which performs transformation from two-dimensional coordinates to three-dimensional coordinates, and a three-dimensional coordinate to two-dimensional coordinate transformation section 205, which performs transformation from three-dimensional coordinates to two-dimensional coordinates. For example, the coordinate transformation section 203 calculates the light irradiation position and the light detection position or the calculation position of a measurement channel by sequentially repeating the coordinate transformation processing between the shapes approximated on the way from the two-dimensional head image to the three-dimensional head image. As will be described in detail later, the coordinate transformation section 203 can perform both two-dimensional display and three-dimensional display of a probe position so that the user information can be input or an operation result can be output and displayed. In addition, the above-described main functions that the biological light measurement device 100 of the present invention have are realized by all of the control unit 103, the display unit 114, and the like using software, and it is needless to say that they are not limited to the block configuration shown in FIG. 2.

In other words, the biological light measurement device 100 of the present invention has a function of easily displaying and setting the light irradiation position and the light detection position or the three-dimensional position of a measurement channel using a display unit with a GUI function. That is, it is possible to realize a function of easily setting the light irradiation position and the light detection position of a subject body on the two-dimensional head image of the display screen, estimating the light irradiation position and the light detection position on the three-dimensional head image by arithmetic processing, such as coordinate transformation, based on the information set in this way, and displaying the actually measured topographic image at the calculation position on the head image obtained by arithmetic processing so as to overlap each other, without measuring the actual light irradiation position and light detection position set in the subject body after a measuring person mounts the probe holder 108 at the head of the subject body 107. Accordingly, since time and effort when measuring the actual light irradiation position and light detection position set in the subject body at the time of biological light measurement can be omitted, a burden on the measuring person and the subject body can be significantly reduced.

(1.0 Specific Example of the Overall Configuration)

Figure 3:
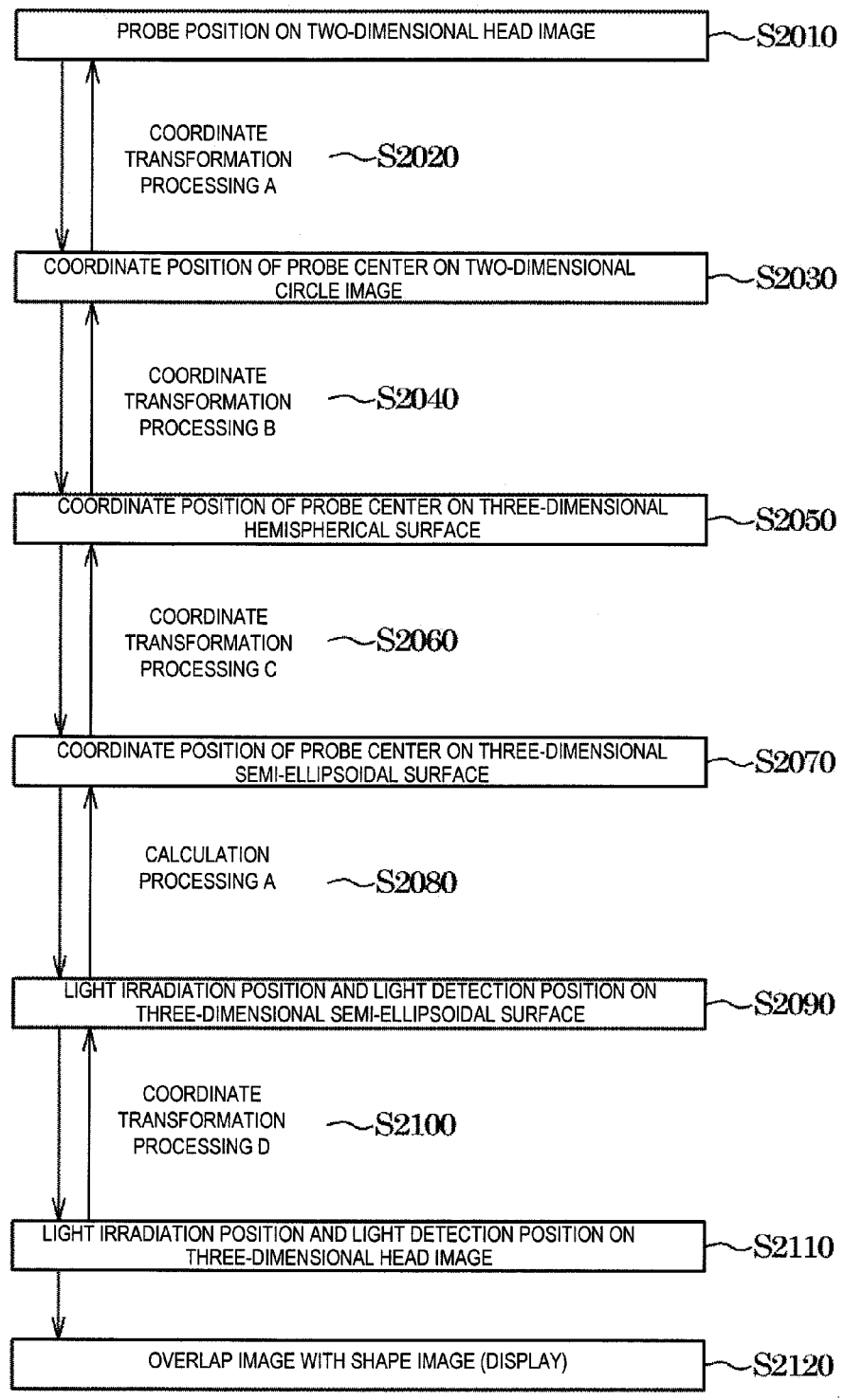
FIG. 3 is a view for explaining the flow chart in an embodiment of the present invention.

Next, a more specific configuration for realizing each function of the biological light measurement device 100 of the present invention will be described using the flow chart of FIG. 3 and examples of operation screens and the like displayed on display screens of FIGS. 4 to 10.

Figure 4A:
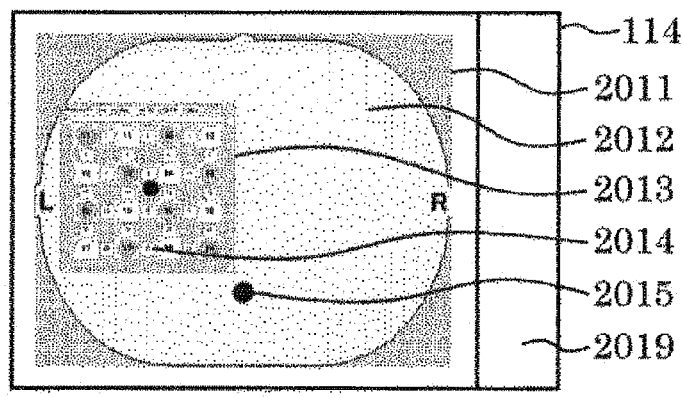
FIG. 4A is a view showing the situation where a measuring person sets a probe position on a two-dimensional head image by a simple operation using a display screen in the embodiment of the present invention.
Figure 4B:
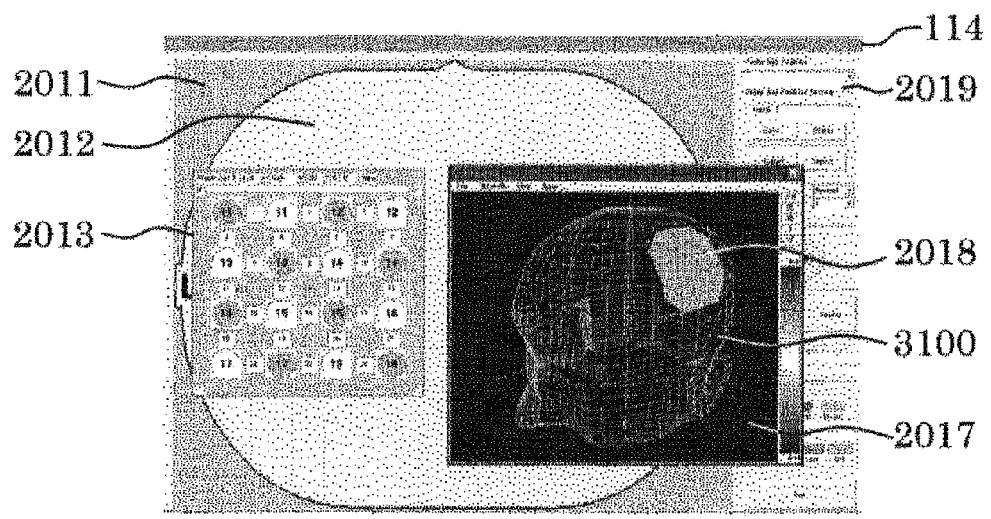
FIG. 4B is a view showing the situation where a measuring person sets a probe position on a screen, on which a two-dimensional head image and a three-dimensional head image are displayed, by a simple operation using a display screen in the embodiment of the present invention.
Figure 4C:
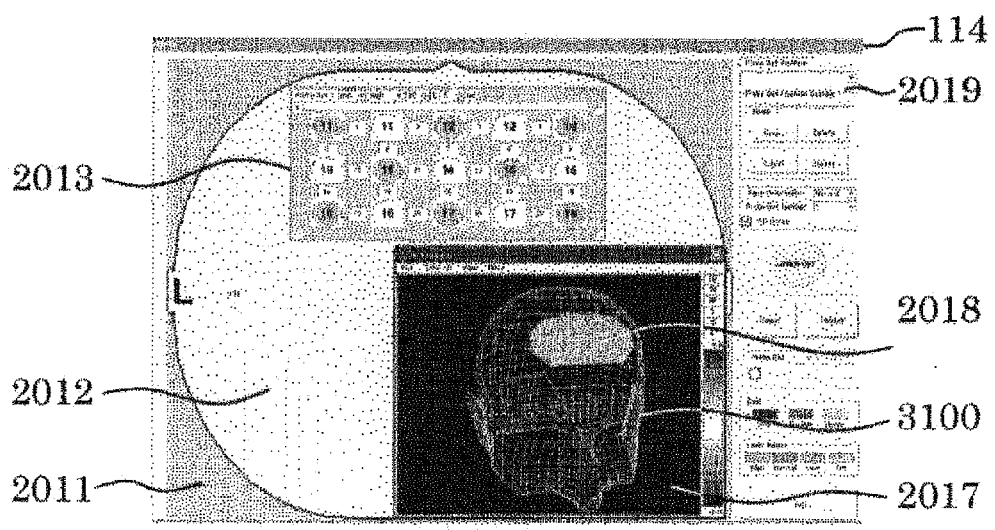
FIG. 4C is a view showing another example in which a measuring person sets a probe position on a screen, on which a two-dimensional head image and a three-dimensional head image are displayed, by a simple operation using a display screen in the embodiment of the present invention.

First, a user selects a "standard pattern of the head shape" or a "probe", which is optimal for a subject body, using a display screen by the head shape data selecting section 201. FIG. 4 (FIGS. 4A, 4B, and 4C) shows an example of the display screen in the present invention.

In the present embodiment, an operation screen 2011 which gives a priority to ease of an operation is assumed. That is, the operation screen 2011 shown in FIG. 4A is displayed on the display screen of the display unit 114. A light irradiation position and a light detection position or a measurement channel, that is, a two-dimensional head image 2012, one probe (two-dimensional probe) 2013 in which a plurality of light irradiation positions and a plurality of light detection positions are set as one group as a whole, a center coordinate position 2014 of a two-dimensional probe, and a center coordinate position 2015 of a two-dimensional head image are displayed on this operation screen 2011. 2019 is an operation input unit in which input columns of various kinds of instructions or data and icons, such as pull down type operation buttons, are disposed. A user may arbitrarily select or change and display the shapes, positions, and sizes of the two-dimensional head image 2012 and the two-dimensional probe 2013 on the operation screen 2011 according to the age of the subject body 107, measurement purposes, type of the probe holder 108 to be used, and the like by mouse operation or the like.

The two-dimensional head image 2012 shown in FIG. 4A is a plane image when the head is viewed from above. A plurality of light irradiation positions and a plurality of light detection positions are regularly arrayed in one square probe corresponding to the shape of the probe holder 108 used, and the probe center is present at the center of the figure. In addition, distances between the light irradiation positions or the light detection positions may be set to be unequal by the installation position of the probe holder 108 so as to correspond to the top view of the probe holder 108 in a state mounted on the head, and the central position of the figure may also be shifted within the probe so that it is displayed on the two-dimensional head image.

In addition, as a two-dimensional head image, it is also possible to form a database so that images when the head is viewed from various directions according to measurement purposes, for example, two-dimensional head images of left and right temporal parts, the front, or the back of the head can be selected as two-dimensional images for positioning by the user.

Then, the user sets the position of the probe 2013 on the selected two-dimensional head image 2012 on the software (S2010).

Then, a measuring person calculates a light irradiation position and a light detection position on the three-dimensional head image using the setting position information regarding the probe position on the two-dimensional head image set by a simple operation (S2110).

First, the user performs coordinate transformation processing on the basis of the position of the probe 2013 on the two-dimensional head image set on the software. In this coordinate transformation processing, coordinate transformation processing between the shapes approximated on the way from the two-dimensional head image to the three-dimensional head image is executed while being sequentially repeated, and the light irradiation position and the light detection position or the calculation position of a measurement channel is calculated. That is, by performing coordinate transformation processing A (S2020), coordinate transformation processing B (S2040), and coordinate transformation processing C (S2060) regarding the position of the probe center, the position of the probe center on the three-dimensional semi-ellipsoidal surface is calculated (S2060).

Moreover, processing of calculating the length of an ellipse arc and processing of calculating a light irradiation position and a light detection position from the coordinate position of the probe center on the three-dimensional semi-ellipsoidal surface are executed (S2080). On the basis of a result of such calculation processing, a light irradiation position and a light detection position on the three-dimensional head image or a measurement channel, that is, a light irradiation position and a light detection position are further calculated (S2110). In addition, types of the shape approximated on the way or the number of times of coordinate transformation processing is not limited to the example described above. For example, the intermediate coordinate transformation processing C (S2060) described above may be omitted. Alternately, it is also possible to set a three-dimensional hemispherical image, instead of the three-dimensional head image, as a final image by performing the coordinate transformation processing B and C on a two-dimensional head image and to calculate a light irradiation position, a light detection position, or a measurement channel from the coordinate position of the probe center on the three-dimensional hemispherical image. Alternatively, it is also possible to set a three-dimensional hemispherical image, instead of the three-dimensional head image, as a final image and to calculate a light irradiation position and a light detection position or a measurement channel.

Then, after the light irradiation position and the light detection position on the three-dimensional head image or the measurement channel (the light irradiation position and the light detection position) is calculated (S2110), a body transmitted light intensity image and a shape image of an object to be measured as an indication of a measured part are displayed so as to overlap each other on three dimensions (S2120).

Moreover, as shown in FIG. 4B, in step (S2010) in which the user sets the probe position on the software, a three-dimensional head image (wireframe image) 3100 may be displayed simultaneously on the operation screen 2011 so as to overlap the two-dimensional head image 2012. This is based on a result in which a result of calculation processing is immediately reflected on the operation screen since the two-dimensional shape data and the three-dimensional shape data are set as a table as a pair and stored in a storage device or on the basis of a bidirectional processing function of coordinate transformation between two dimensions and three dimensions, which will be described in detail later. As a three-dimensional head shape image of an object to be measured which is overlapped, a shape frame image of the head of a subject body is used in the present embodiment. In FIG. 4B, numeric values in circles and rectangular corners within the two-dimensional probe 2013 indicate irradiation positions and light detection positions in the left head of the subject body. In addition, the three-dimensional head image 3100 is displayed in a three-dimensional probe 2017. The position of a three-dimensional probe 2018 in the three-dimensional head image 3100 is a left head corresponding to the position of the two-dimensional probe 2013 in the two-dimensional head image 2012.

FIG. 4C shows a state where a horizontally long rectangle is selected as a shape of the two-dimensional probe 2013 by a mouse operation and the position is also in a frontal part. At this time, the position of the three-dimensional probe 2018 in the three-dimensional head image 3100 is also in the frontal part. By the bidirectional processing function of coordinate transformation processing, the user can change the shape and position of the three-dimensional probe 2018 by a mouse operation or the like. Accordingly, it is possible to change the shape and position of the two-dimensional head image 2012. In addition, it is also possible to make the shape and position of the three-dimensional probe 2018 easily viewed by rotating the three-dimensional head image 3100 by a mouse operation or the like. At this time, the position of a two-dimensional probe in a two-dimensional head image is in cooperation changed, moved, and displayed. Thus, by displaying the two-dimensional head image and the three-dimensional head image simultaneously on the operation screen 2011, it is possible to check more accurately the light irradiation position and the light detection position of the subject body on the head image of the display screen set by a simple operation of a measuring person and to modify it as necessary. According to a situation, a measuring person may operate the three-dimensional probe 2018 on the three-dimensional head image by a simple operation using a mouse or the like and input the three-dimensional position coordinates of the probe holder 108.

Here, the processing S2010 in which a user sets the probe position 2010 on a two-dimensional head image on the software will be described.

First, a user sets the probe position 2010 on the two-dimensional head image 2012, which is displayed on the operation screen 2011 of FIG. 4A, by a mouse operation or the like. Moreover, in the present embodiment, the case is assumed in which the two-dimensional head image 2012 is used to show the approximate positions of the light irradiation position and the light detection position and the accuracy of the positional information of the light irradiation position and the light detection position on the two-dimensional head image 2012 is low accordingly.

In the above conditions assumed, the center coordinate position 2014 of a probe on the two-dimensional head image is used as setting position information of the user on the two-dimensional head image 2012.

Next, processing in a forward direction in the flow of FIG. 3, that is, coordinate transformation processing A to D on a two-dimensional head image→on a three-dimensional head image and calculation processing A (S2080) will be described.

Figure 5:
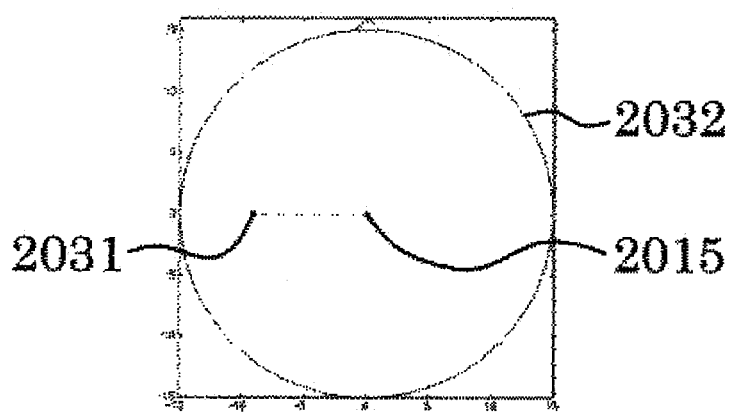
FIG. 5 is a view showing the processing of calculating the coordinate position of the probe center on a two-dimensional circle image from the center coordinate position of the probe on a two-dimensional head image by performing coordinate transformation processing A in the embodiment of the present invention.

In the processing in a forward direction, first, coordinate transformation processing A (S2020) is performed to calculate a coordinate position 2031 of the probe center on a two-dimensional circle image 2032, which is shown in FIG. 5, from the center coordinate position 2014 of the probe on the two-dimensional head image 2012 (S2030). In addition, the center of the two-dimensional circle image 2032 matches the center coordinate position 2015 of the two-dimensional head image.

Figure 6:
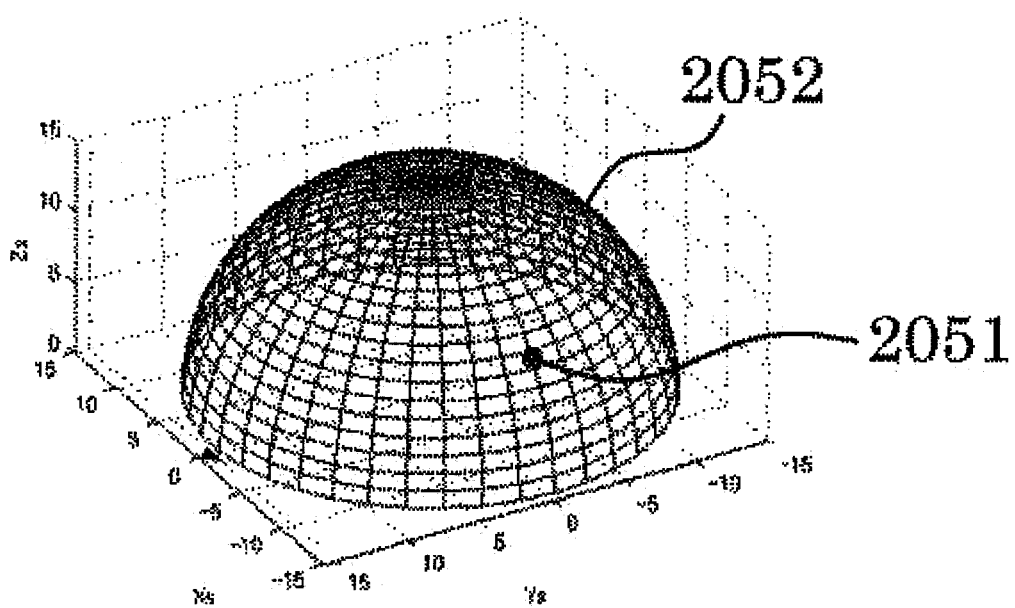
FIG. 6 is a view showing the processing of calculating the coordinate position of the probe center on a three-dimensional hemispherical surface from the coordinate position of the probe center on a two-dimensional circle image by performing coordinate transformation processing B in the embodiment of the present invention.

Then, coordinate transformation processing B (S2040) is performed to calculate a coordinate position 2051 of the probe center on a three-dimensional hemispherical surface 2052, which is shown in FIG. 6, from the coordinate position 2031 of the probe center on the two-dimensional circle image 2012 (S2050).

Figure 7:
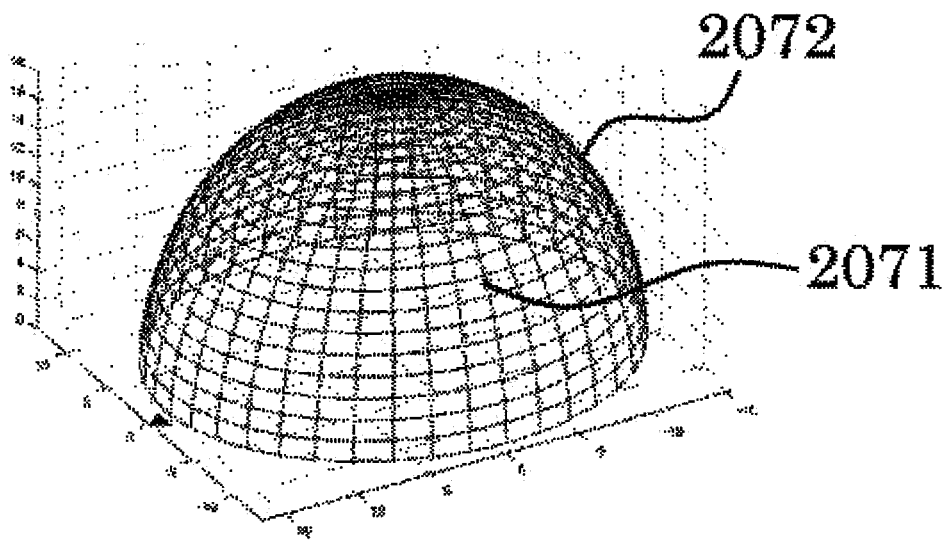
FIG. 7 is a view showing the processing of calculating the coordinate position of the probe center on a three-dimensional semi-ellipsoidal surface from the coordinate position of the probe center on a three-dimensional hemispherical surface by performing coordinate transformation processing C in the embodiment of the present invention.

Then, coordinate transformation processing C (S2060) is performed to calculate a coordinate position 2071 of the probe center on a three-dimensional semi-ellipsoidal surface 2072, which is shown in FIG. 7, from the coordinate position 2051 of the probe center on the three-dimensional hemispherical surface (S2070).

Figure 8:
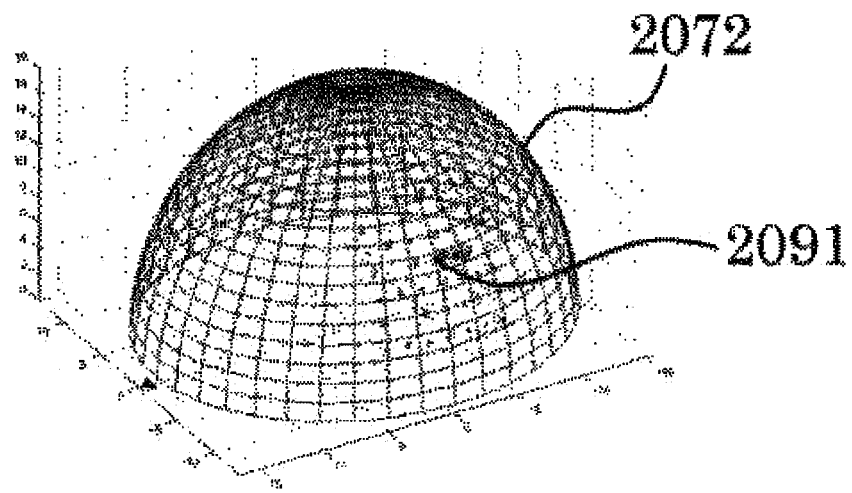
FIG. 8 is a view showing the processing of calculating a light irradiation position and a light detection position on a three-dimensional semi-ellipsoidal surface from the coordinate position of the probe center on a three-dimensional semi-ellipsoidal surface by calculation processing A in the embodiment of the present invention.

Then, by the calculation processing A (S2080), a light irradiation position and light detection position 2091 on the three-dimensional semi-ellipsoidal surface 2072 shown in FIG. 8 is calculated from the coordinate position 2071 of the probe center on the three-dimensional semi-ellipsoidal surface (S2090). Details of the calculation processing A (S2080) will be described later.

Figure 9:
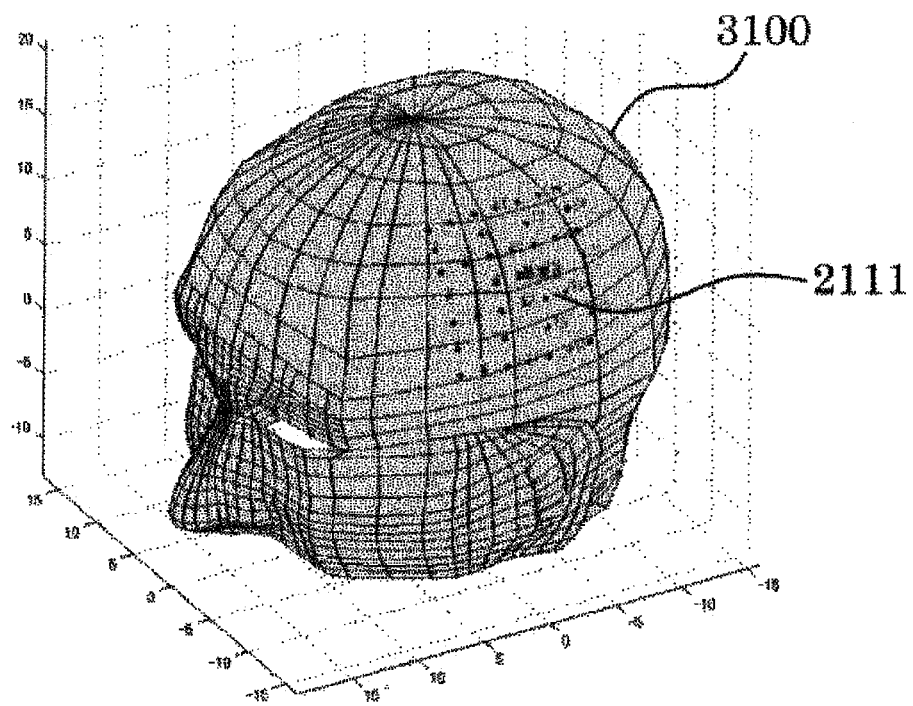
FIG. 9 is a view showing the processing of calculating a light irradiation position and a light detection position on a three-dimensional head image from the light irradiation position and the light detection position on the three-dimensional semi-ellipsoidal surface using coordinate transformation processing D in the embodiment of the present invention.

Then, using the coordinate transformation processing D (S2100), a light irradiation position and light detection position 2111 on the three-dimensional head image 3100 shown in FIG. 9 is calculated from a light irradiation position and light detection position 2090 on the three-dimensional semi-ellipsoidal surface (S2110). Calculating the position on the three-dimensional semi-ellipsoidal surface 2072 in the course of coordinate transformation is performed because the three-dimensional shape of the three-dimensional semi-ellipsoidal surface 2072 is closer to the three-dimensional shape of the three-dimensional head image 3100 than to that of the three-dimensional hemispherical surface 2052 and accordingly, there is an advantage in that processing of coordinate transformation becomes easy.

In addition, it is also possible to calculate a light irradiation position and a light detection position on a three-dimensional head image by performing the same coordinate transformation processing as in the present embodiment using the positional information regarding a light irradiation position and a light detection position on a two-dimensional head image as information regarding the setting position by the user on the two-dimensional head image (S2110).

Figure 10:
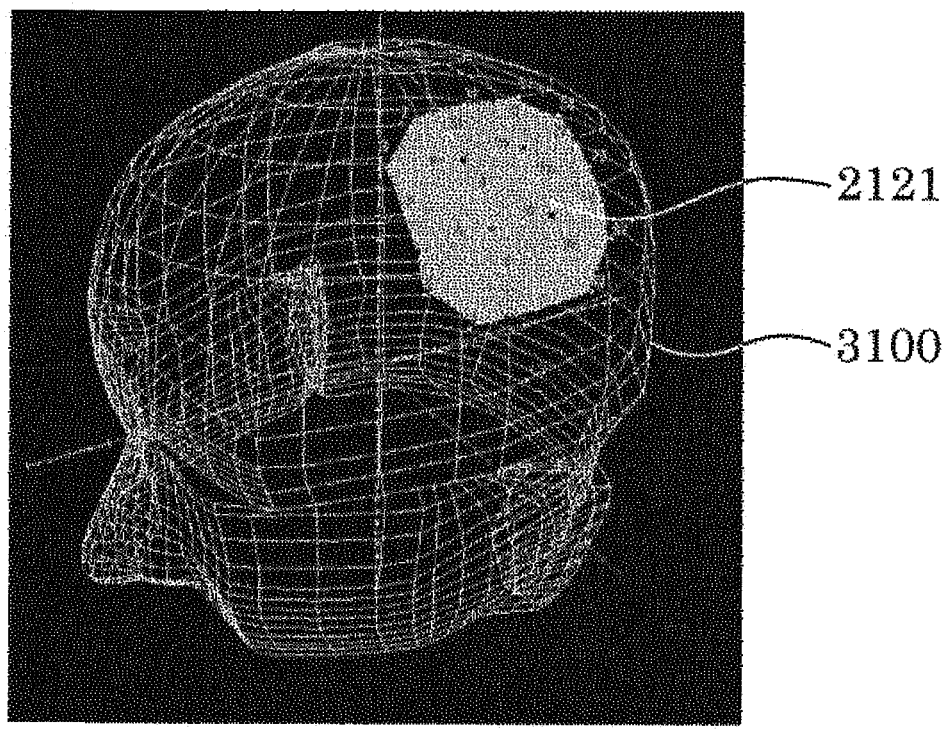
FIG. 10 is a view showing the processing of calculating a light irradiation position and a light detection position on the three-dimensional head image and then displaying a body transmitted light intensity image and a shape image of an object to be measured as an indication of a measured part so as to overlap each other on three dimensions in the embodiment of the present invention.

After the light irradiation position and light detection position 2111 on the three-dimensional head image is calculated, a body transmitted light intensity image 2121 and a shape image of an object to be measured as an indication of a measured part are displayed so as to overlap each other on three dimensions, as shown in FIG. 10 (S2120).

Next, a supplementary explanation regarding the processing (S2120) of overlapping display with a shape image will be given. The topographic image generating section 207 based on the light irradiation position calculates a distance d between a light irradiation position and a light detection position, which are adjacent to each other, in a three-dimensional space from the read light irradiation position and light detection position 2111 for every measurement position. At this time, in the present embodiment, the number of measurement positions is 16. Accordingly, the number of distances d between light irradiation positions and light detection positions in the three dimensional space calculated by the calculation is 24. Then, the topographic image generating section 207 corrects a topographic image Hb data (original), which is based on the two-dimensional light irradiation position and light detection position that are topographic images before correction, according to the following expression (1), and generates a topographic image Hb data (new) based on the three-dimensional light irradiation position and light detection position that are topographic images after correction. Specifically, the pixel value of each pixel of a topographic image obtained by cubic spline interpolation is corrected by the distance d of a measurement position closest to the pixel. In addition, the correction at this time is based on the following expression (1).

$$Hb\ data\ (new) = Hb\ data\ (original) \times Distance \quad (1)$$

Here, Distance=d/30

Then, the topographic image generating section 207 converts the topographic image after correction into a topographic image according to the wireframe image generated previously. Specifically, the topographic image generating section 207 converts the topographic image after correction into a three-dimensional topographic image by performing three-dimensional mapping interpolation of the pixel value of each pixel, which forms a topographic image, so as to match head wireframe coordinates.

Thereafter, the topographic image generating section 207 generates a three-dimensional image in which a topographic image overlaps a wireframe image, converts the three-dimensional image into a two-dimensional image ("three-dimensional topographic image") seen from the viewing position instructed from an input means, and displays it on the display surface of the display means.

Next, processing in a backward direction in the flow chart of FIG. 3, that is, processing on a three-dimensional head image→on a two-dimensional head image will be described.

As previously described, the coordinate transformation processing A (S2020), the coordinate transformation processing B (S2040), the coordinate transformation processing C (S2060), and the coordinate transformation processing D (S2100) are reversible coordinate transformation processing. Therefore, it is also possible to calculate and display the probe position on a two-dimensional head image by setting the probe position on a three-dimensional head image on the three-dimensional head image by the user.

First, for example, on the three-dimensional head image 3100 in a state shown in FIG. 4B, a user sets the probe position 2017 on the three-dimensional head image on the software. Here, simply, the position equivalent to the central point of the probe 2111 on the three-dimensional head image 3100, which is shown in FIG. 9, is assumed to be set.

Then, using the coordinate transformation processing D (S2100), the coordinate position 2071 of the probe center on the three-dimensional semi-ellipsoidal surface 2072 shown in FIG. 7 is calculated from the probe center on the three-dimensional head image.

Then, using the coordinate transformation processing C (S2060), the coordinate position 2051 of the probe center on the three-dimensional hemispherical surface 2052 shown in FIG. 6 is calculated from a coordinate position 2070 of the probe center on the three-dimensional semi-ellipsoidal surface. In addition, using the coordinate transformation processing B (S2040), the coordinate position 2031 of the probe center on the two-dimensional circle image 2032 shown in FIG. 5 is calculated from the coordinate position 2051 of the probe center on the three-dimensional hemispherical surface. Using the coordinate transformation processing B (S2020), the position of the probe 2013 on the two-dimensional head image is calculated from the coordinate position 2031 of the probe center on this two-dimensional circle image.

As previously described, the light irradiation position and light detection position 2091 on the three-dimensional semi-ellipsoidal surface 2072 and the light irradiation position and light detection position 2111 on the three-dimensional head image 3100 are calculated from the coordinate position 2071 of the probe center on the three-dimensional semi-ellipsoidal surface 2072.

As described above, according to the present invention, a body transmitted light intensity image and a shape image of an object to be measured as an indication of a measured part can be displayed so as to overlap each other on three dimensions, without measuring the three-dimensional coordinates of the light irradiation position and the light detection position, by realizing a function in which a measuring person sets a light irradiation position and a light detection position on the head image displayed on two dimensions and calculates a light irradiation position and a light detection position on three dimensions according to the set information. That is, with no need that a measuring person measures the three-dimensional coordinates of a light irradiation position and a light detection position in the head of a subject body, a body transmitted light intensity image of the subject body and a shape image of an object to be measured as an indication of a measured part can be displayed so as to overlap each other on the three-dimensional image. Since an accurate measurement result of the light irradiation position and the light detection position is not needed, a time of the whole biological light measurement can be shortened by omission of position measurement, and the cost and a burden on a measuring person can be reduced.

Next, the coordinate transformation processing in the embodiment of the present invention will be described in more detail.

(2.1. Two-Dimensional Head Image ⇔ Two-Dimensional Circle Image)

Figure 11:
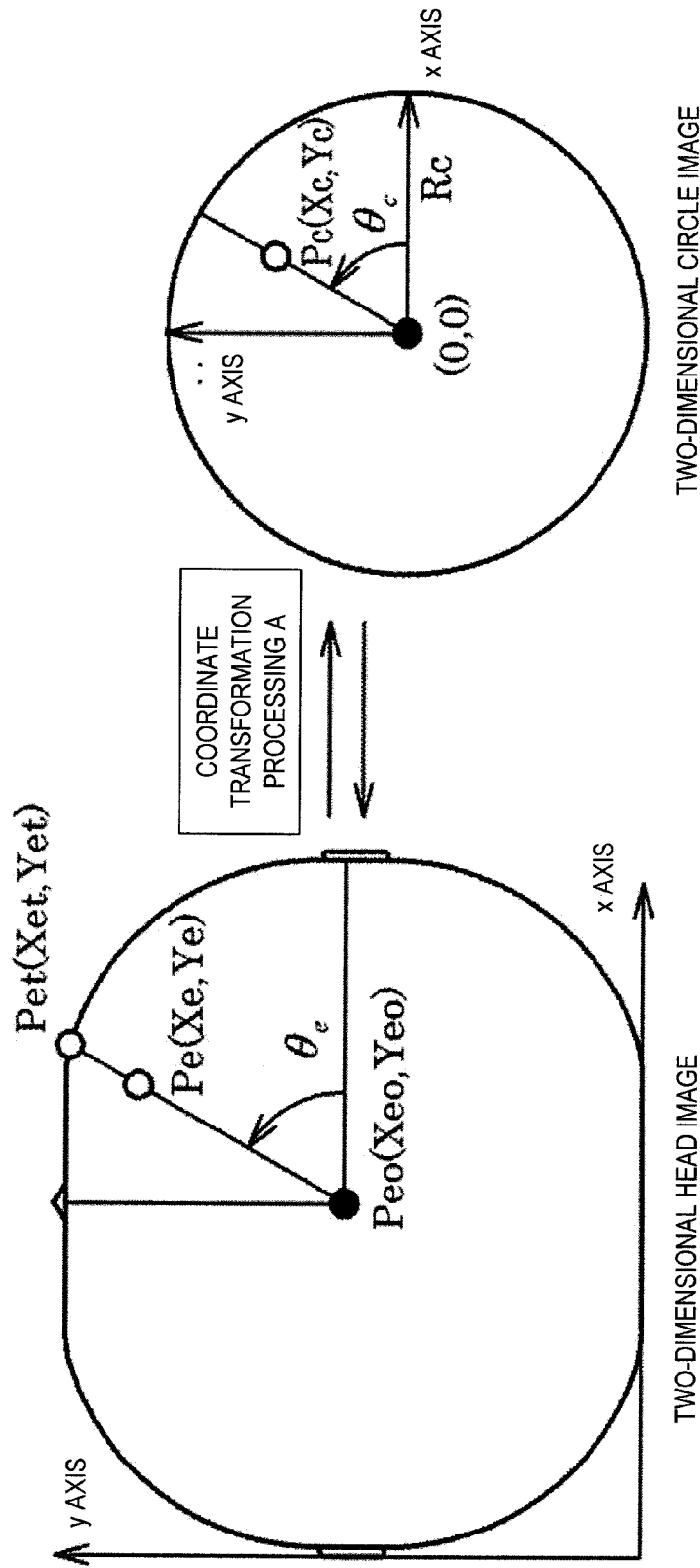
FIG. 11 is a view for explaining the coordinate transformation processing A.

First, the coordinate transformation processing A (S2020) will be described using FIG. 11.

(2.1.1. Coordinate Transformation Processing A Two-Dimensional Head Image→Two-Dimensional Circle Image)

The calculation procedure of making a point on a two-dimensional head image uniquely correspond to a point on a two-dimensional circle image by the coordinate transformation processing A (S2020) will be described. The two-dimensional circle image is assumed to be a circle with a radius Rc and the central point (0 0).

Each coordinate point and each angle of deflection are expressed as follows.

Point Pe(Xe Ye): coordinate point on a two-dimensional head image to be subjected to the coordinate transformation processing A (2020)

Point Oe(Xeo Yeo): central point of a two-dimensional head image

Point Pet (Xet Yet): point of intersection of a straight line OePe and a two-dimensional head image Angle of deflection $\theta_e$: angle of deflection on a two-dimensional head image Angle of deflection $\theta_c$: angle of deflection on a two-dimensional circle image Point Pc(Xc Yc): coordinates on a two-dimensional circle image after coordinate transformation of the point Pe by the coordinate transformation processing A The calculation of coordinate transformation is performed as follows.

(I) In the case of (Xe Ye)=(Xeo Yeo)

$$(Xc\, Yc) = (0\, 0)$$

(II) In the case of (Xe Ye)≠(Xeo Yeo)
(i) The angle of deflection $\theta_e$ is calculated.

$$\theta_e = \arccos\left(\frac{Xe - Xeo}{\sqrt{(Xe - Xeo)^2 + (Ye - Yeo)^2}}\right)$$

$$(0 \le \theta_e \le \pi)$$

The same if Ye−Yeo≥0 (0≤$\theta_e$≤π)

$$\theta_e = -\theta_e \text{ if } Ye - Yeo < 0\, (-\pi \le \theta_e \le 0)$$

(ii) The point of intersection Pet(Xet Yet) of the straight line OePe and a two-dimensional head image is calculated.
(iii) The point Pc(Xc Yc) is calculated.
The angle of deflection on the two-dimensional circle image $\theta_c = \theta_e$.

$$(Xc\ Yc) = Rc \cdot \frac{\sqrt{(Xe - Xeo)^2 + (Ye - Yeo)^2}}{\sqrt{(Xet - Xeo)^2 + (Yet - Yeo)^2}} \cdot (\cos(\theta_c)\sin(\theta_c))$$

is calculated.

(2.1.2. Coordinate Transformation Processing A Two-Dimensional Circle Image→Two-Dimensional Head Image)

The calculation procedure of making a point on a two-dimensional circle image uniquely correspond to a point on a two-dimensional head image by the coordinate transformation processing A (S2020) will be described. It is assumed that the two-dimensional circle image is a circle with a radius Rc and a central point (0 0).

Each coordinate point and each angle of deflection are expressed as follows.

Point Pc(Xc Yc): coordinates on a two-dimensional circle image to be subjected to the coordinate transformation processing A $\theta_c$: angle of deflection on a two-dimensional circle image $\theta_e$: angle of deflection on a two-dimensional head image Point Oe (Xeo Yeo): central point Oe of a two-dimensional head image Point Pet(Xet Yet): point of intersection of a straight line OePe and a two-dimensional head image Point Pe(Xe Ye): coordinates on a two-dimensional head image after coordinate transformation of the point Pc by the coordinate transformation processing A The calculation of coordinate transformation is performed as follows.

(I) In the case of (Xc Yc)=(0 0)

(XeYe)=(XeoYeo)

(II) In the case of (Xc Yc)≠(0 0)

(i) The angle of deflection $\theta_c$ is calculated.

$$\theta_c = \arccos\left(\frac{Xc}{\sqrt{Xc^2 + Yc^2}}\right)$$

$(0 \leq \theta_c \leq \pi)$

The same if Yc≥0 (0≤$\theta_c$≤π)

$\theta_c = -\theta_c$ if Yc<0(−π≤$\theta_c$≤0)

(ii) The point Pet(Xet Yet) is calculated.
(ii-1) The angle of deflection is calculated as $\theta_e = \theta_c$.
(ii-2) A straight line OePet is calculated.
(1) In the case of $$\theta_e \neq \pm\frac{\pi}{2},$$

$$y = \tan\theta_e \times (x - Xeo) + Yeo$$

(2) In the case of $$\theta_e = \pm\frac{\pi}{2},$$

$$x = 0$$

(ii-3) The point Pet(Xet Yet) is calculated by calculating the point of of intersection of the head image and the straight line.

(iii) The point Pe(Xe Ye) is calculated.

$$(Xe\ Ye) = \sqrt{Xet^2 + Yet^2} \cdot \frac{\sqrt{Xc^2 + Yc^2}}{Rc} \cdot (\cos\theta_e\ \sin\theta_e) + (Xeo\ Yeo)$$

(2.2. Two-Dimensional Circle Image ⇔ Three-Dimensional Hemispherical Surface)

Figure 12:
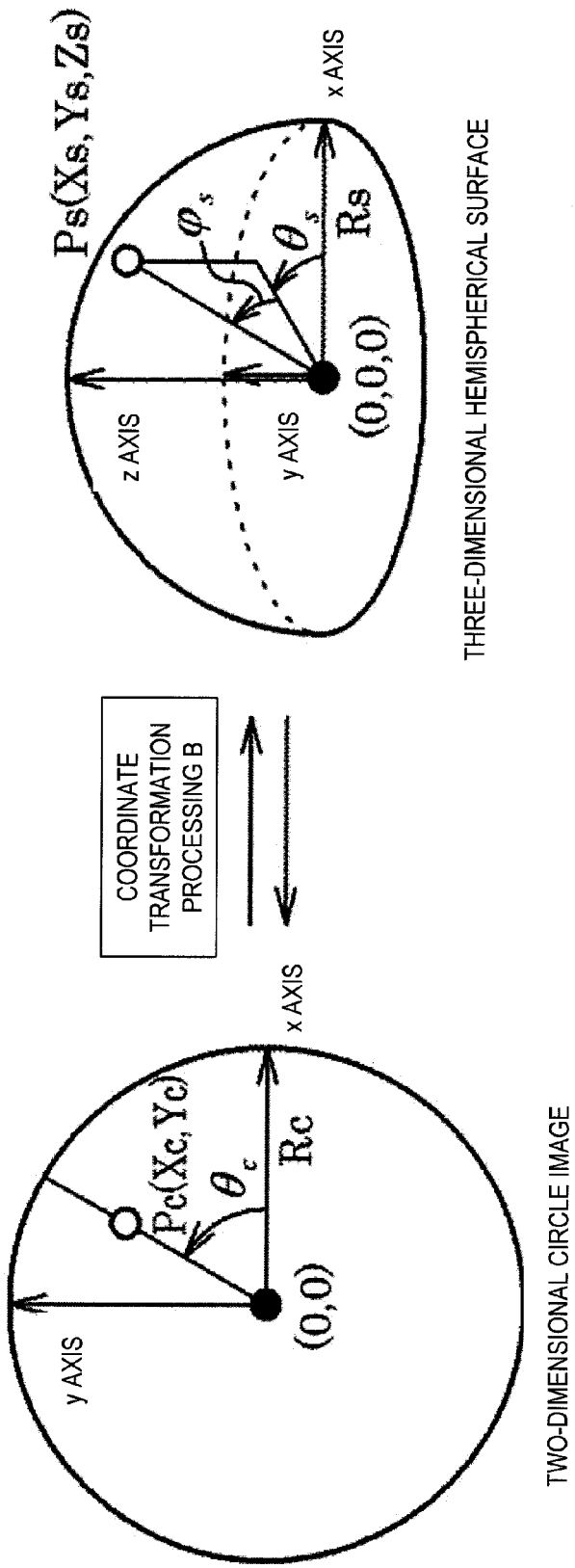
FIG. 12 is a view for explaining the coordinate transformation processing B.

The coordinate transformation processing B (S2040) will be described using FIG. 12.

(2.2.1. Coordinate Transformation Processing B Two-Dimensional Circle Image→Three-Dimensional Hemispherical Surface)

The calculation procedure of making a point on a two-dimensional circle image uniquely correspond to a point on a three-dimensional hemispherical surface by the coordinate transformation processing B (S2040) will be described.

It is assumed that the two-dimensional circle image is a circle with a radius Rc and a central point (0 0) and the three-dimensional hemispherical surface is a hemispherical surface with a radius Rs and a central point (0 0 0).

Each coordinate point is expressed as follows.

Point Pc (Xc Yc): point on a two-dimensional circle image to be subjected to the coordinate transformation processing B Point Ps(Xs Ys Zs): point on a three-dimensional hemispherical surface after coordinate transformation of the point Pc by the coordinate transformation processing B (Zs≥0)

The calculation of coordinate transformation is performed as follows.

(I) Coordinates of the point Pc are transformed into polar coordinates.

Using the polar coordinates, the coordinates of the point Pc are expressed as (Xc Yc)=Rc·(cos $\theta_c$ sin $\theta_c$)

$$\theta_c = \arccos\left(\frac{Xc}{\sqrt{Xc^2 + Yc^2}}\right)$$

$(0 \leq \theta_c \leq \pi)$

The same if Yc≥0 (0≤$\theta_c$≤π)

$\theta_c = -\theta_c$ if Yc<0(−π≤$\theta_c$≤0)

(II) Polar coordinates of the point Ps are calculated, and the point Ps(Xs Ys Zs) is calculated.

Angles of deflection $\theta_s$ and $\phi_s$ used for polar coordinate expression of the point Ps are calculated as follows.

$$\theta_s = \theta_c$$

$$\phi_s = \frac{\pi}{2} \times \left(1 - \frac{\sqrt{Xc^2 + Yc^2}}{Rc}\right)$$

$\left(0 \leq \phi_s \leq \frac{\pi}{2}\right)$

In addition, the coordinates of the point Ps are calculated as $$\begin{pmatrix} Xs \\ Ys \\ Zs \end{pmatrix} = Rs \cdot \begin{pmatrix} \cos\varphi_s \cdot \cos\theta_s \\ \cos\varphi_s \cdot \sin\theta_s \\ \sin\varphi_s \end{pmatrix}$$

(2.2.2. Coordinate Transformation Processing B Three-Dimensional Hemispherical Surface→Two-Dimensional Circle Image)

The calculation procedure of making a point on a three-dimensional hemispherical surface uniquely correspond to a point on a two-dimensional circle image by the coordinate transformation processing B (S2040) will be described.

It is assumed that the two-dimensional circle image is a circle with a radius Rc and a central point (0 0) and the three-dimensional hemispherical surface is a hemispherical surface with a radius Rs and a central point (0 0 0).

Each coordinate point is expressed as follows.

Point Ps(Xs Ys Zs): point on a three-dimensional hemispherical surface to be subjected to coordinate transformation processing B (Zs≥0)

Point Pc (Xc Yc): point on a two-dimensional circle image after coordinate transformation of the point Ps by the coordinate transformation processing B The calculation of coordinate transformation is performed as follows.

(I) Coordinates of the point Ps are transformed into polar coordinates.

Using the polar coordinates, the coordinates of the point Ps are expressed as $$\begin{pmatrix} Xs \\ Ys \\ Zs \end{pmatrix} = Rs \cdot \begin{pmatrix} \cos\varphi_s \cdot \cos\theta_s \\ \cos\varphi_s \cdot \sin\theta_s \\ \sin\varphi_s \end{pmatrix}$$

Angles of deflection $\theta_s$ and $\phi_s$ are calculated as follows.

$$\varphi_s = \arcsin\left(\frac{Zs}{Rs}\right)(Zs \geq 0 \text{ and } 0 \leq \varphi_s \leq \frac{\pi}{2})$$

$$\theta_s = \arccos\left(\frac{Xs}{Rs \times \cos\varphi_s}\right)(0 \leq \theta_s \leq \pi)$$

The same if $$\frac{Ys}{Rs \times \cos\varphi_s} \geq 0$$

$$\theta_s = -\theta_s \text{ if } \frac{Ys}{Rs \times \cos\varphi_s} < 0$$

(II) Polar coordinates of the point Pc are calculated, and the point Pc(Xc Yc) is calculated.

The angle of deflection $\theta_c$ and a moving radius r used for polar coordinate expression of the point Pc are calculated as follows.

$$\theta_c = \theta_s$$

$$r = Rc \times \left(1 - \frac{\varphi_s}{\pi/2}\right)$$

In addition, the coordinates of the point Pc are calculated as (Xc Yc)=r·(cos $\theta_c$ sin $\theta_c$)

(2.3. Three-Dimensional Hemispherical Surface ⇔ Three-Dimensional Semi-Ellipsoidal Surface)

Figure 13:
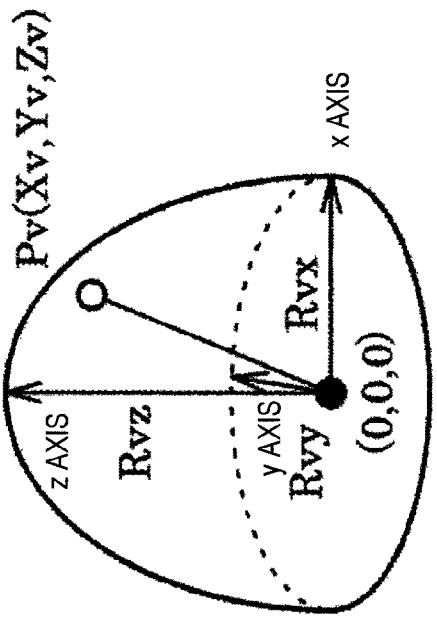
FIG. 13 is a view for explaining the coordinate transformation processing C.
Figure 13:
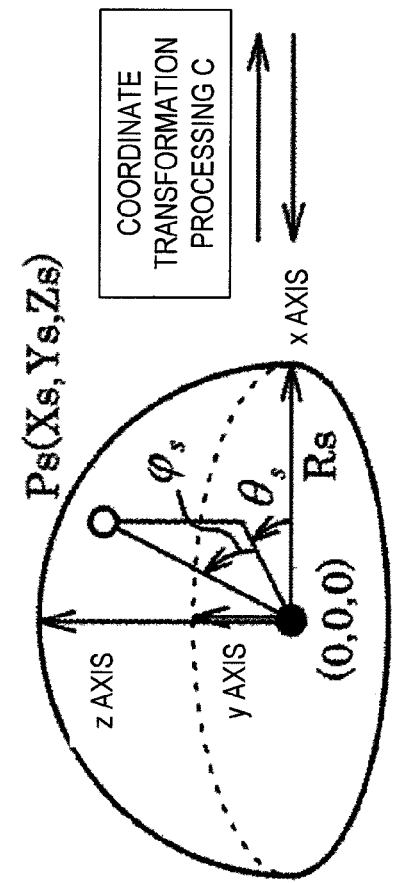

The coordinate transformation processing C (S2060) will be described using FIG. 13.

(2.3.1. Coordinate Transformation Processing C Three-Dimensional Hemispherical Surface→Three-Dimensional Semi-Ellipsoidal Surface)

The calculation procedure of making a point on a three-dimensional hemispherical surface uniquely correspond to a point on a three-dimensional semi-ellipsoidal surface by the coordinate transformation processing C (S2060) will be described.

It is assumed that the three-dimensional hemispherical surface is a hemispherical surface with a radius Rs and a central point (0 0 0). It is assumed that the three-dimensional semi-ellipsoidal surface is a semi-ellipsoidal surface with radii Rvx, Rvy, and Rvz and a central point (0 0 0).

Each coordinate point is expressed as follows.

Point Ps(Xs Ys Zs): point on a three-dimensional hemispherical surface to be subjected to coordinate transformation processing C (Zs≥0)

Point Pv(Xv Yv Zv): point on a three-dimensional semi-ellipsoidal surface after coordinate transformation of the point Ps by the coordinate transformation processing C The calculation of coordinate transformation is performed as follows.

$$(Xv \ Yv \ Zv) = \left(\frac{Rvx}{Rs}Xs \ \frac{Rvy}{Rs}Ys \ \frac{Rvz}{Rs}Zs\right)$$

(2.3.2. Coordinate Transformation Processing C Three-Dimensional Semi-Ellipsoidal Surface→Three-Dimensional Hemispherical Surface)

The calculation procedure of making a point on a three-dimensional semi-ellipsoidal surface uniquely correspond to a point on a three-dimensional hemispherical surface by the coordinate transformation processing C (S2060) will be described.

It is assumed that the three-dimensional semi-ellipsoidal surface is a semi-ellipsoidal surface with radii Rvx, Rvy, and Rvz and a central point (0 0 0). It is assumed that the three-dimensional hemispherical surface is a hemispherical surface with a radius Rs and a central point (0 0 0).

Each coordinate point is expressed as follows.

Point Pv(Xv Yv Zv): point on a three-dimensional semi-ellipsoidal surface to be subjected to coordinate transformation processing C Point Ps(Xs Ys Zs): point on a three-dimensional hemispherical surface after coordinate transformation of the point Pv by the coordinate transformation processing C The calculation of coordinate transformation is performed as follows.

$$(Xs \ Ys \ Zs) = \left(\frac{Rs}{Rvx}Xv \ \frac{Rs}{Rvy}Yv \ \frac{Rs}{Rvz}Zv\right)$$

(2.4. Three-Dimensional Semi-Ellipsoidal Surface ⇔ Three-Dimensional Head Image)

Figure 14:
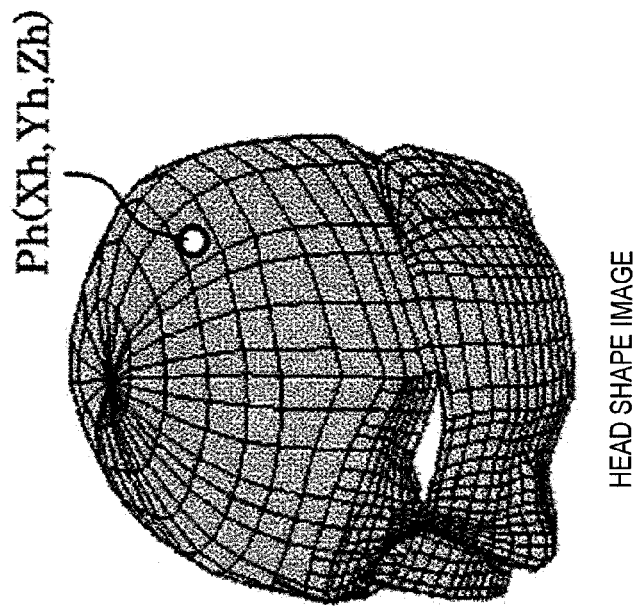
FIG. 14 is a view for explaining the coordinate transformation processing D.
Figure 14:
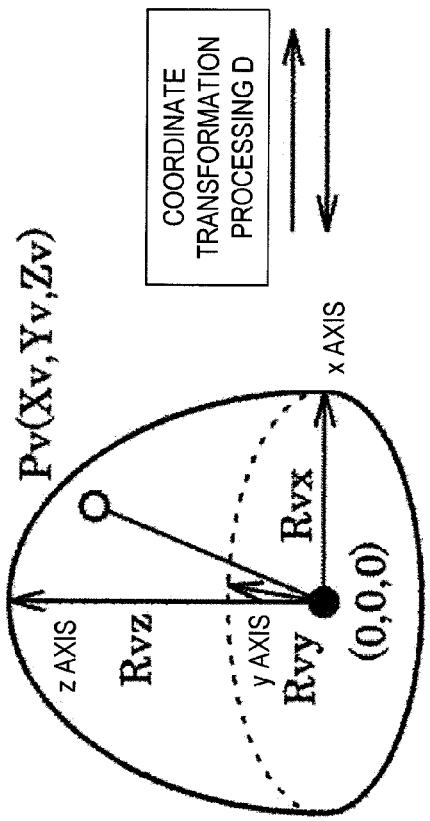

The coordinate transformation processing D (S2100) will be described using FIG. 14.

(2.4.1. Three-Dimensional Semi-Ellipsoidal Surface→Three-Dimensional Head Image)

A point on a three-dimensional semi-ellipsoidal surface is made to uniquely correspond to a point on a three-dimensional head image by the coordinate transformation processing D (S2100).

It is assumed that the three-dimensional semi-ellipsoidal surface is a semi-ellipsoidal surface with radii Rvx, Rvy, and Rvz and a central point (0 0 0).

It is assumed that the three-dimensional head image is formed by N polygons and its central point is (0 0 0).

Although this calculation processing does not depend on the shape of a polygon, it is assumed that the three-dimensional head image is formed by triangle polygons in the present embodiment.

Three points which form each triangle polygon are expressed as $(R_{i,1}, R_{i,2}, R_{i,3}), \ldots (R_{j,1}, R_{j,2}, R_{j,3}), \ldots (R_{N,1}, R_{N,2}, R_{N,3})$. Each coordinate point is expressed as follows.

Point Ov(0 0 0): Central point on a three-dimensional semi-ellipsoid

Point Pv(Xv Yv Zv): point on a three-dimensional semi-ellipsoidal surface to be subjected to coordinate transformation processing D Point Ph(Xh Yh Zh): point on a three-dimensional head image after coordinate transformation of the point Pv by the coordinate transformation processing D The point of intersection of the straight line OvPv and a three-dimensional head image is defined as a point Ph, and it is calculated as follows.

(I) The following calculation is performed for each triangle polygon.

$k_{j,1}, k_{j,2}, k_{j,3}$

Figure 15:
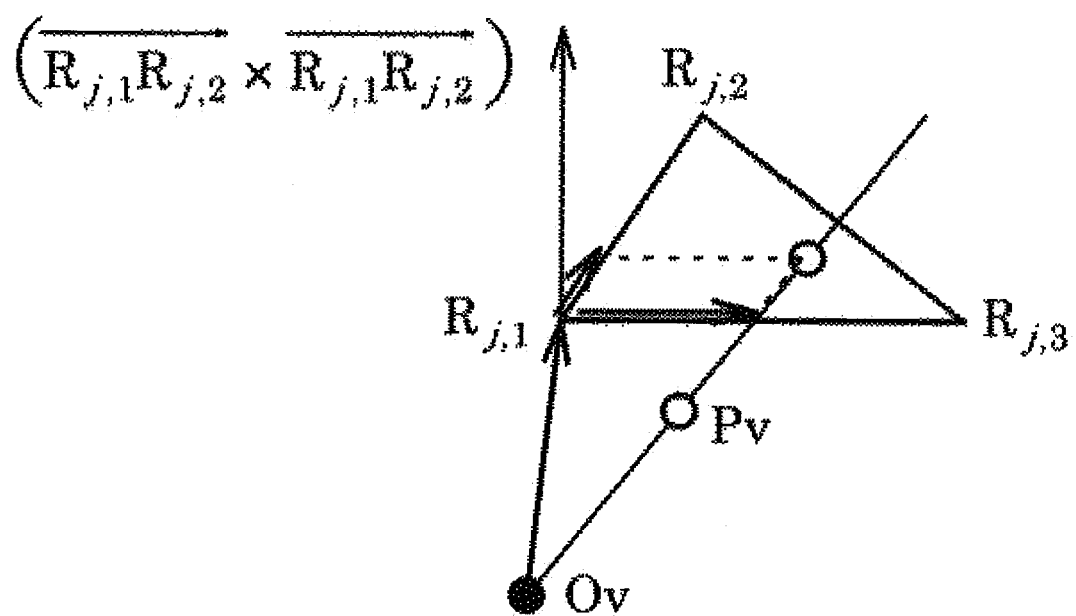
FIG. 15 is a view for explaining the coordinate transformation processing D.

In addition, FIG. 15 shows the relationship between a triangle polygon and a straight line.

$$k_{j,1} = \frac{\overrightarrow{OvR_{j,1}} \cdot (\overrightarrow{R_{j,1}R_{j,2}} \times \overrightarrow{R_{j,1}R_{j,3}})}{\overrightarrow{OvPv} \cdot (\overrightarrow{R_{j,1}R_{j,2}} \times \overrightarrow{R_{j,1}R_{j,3}})}$$

$$k_{j,2} = k_{j,1} \frac{\overrightarrow{OvRv} \cdot (\overrightarrow{OvR_{j,1}} \times \overrightarrow{OvR_{j,3}})}{\overrightarrow{OvR_{j,2}} \cdot (\overrightarrow{OvR_{j,1}} \times \overrightarrow{OvR_{j,3}})}$$

-continued $$k_{j.3} = k_{j.1} \frac{\overrightarrow{OvPv} \cdot (\overrightarrow{OvR_{j.1}} \times \overrightarrow{OvR_{j.2}})}{\overrightarrow{OvR_{j.3}} \cdot (\overrightarrow{OvR_{j.1}} \times \overrightarrow{OvR_{j.2}})}$$

* $\overrightarrow{OR_1} \times \overrightarrow{OR_2}$, $\overrightarrow{OR_1} \times \overrightarrow{OR_3}$, and $\overrightarrow{OR_2} \times \overrightarrow{OR_3}$ indicate a vector cross product.

(II) Find a triangle polygon satisfying $0 \leq k_{j.2} + k_{j.3} \leq 1$, $0 \leq k_{j.2}$, and $0 \leq k_{j.3}$.

(A Triangle Polygon Crossing the Straight Line OvPv is Searched for)

(IIa) When there is a triangle polygon satisfying $0 \leq k_{j.2} + k_{j.3} \leq 1$, $0 \leq k_{j.2}$, and $0 \leq k_{j.3}$, the triangle polygon is expressed as $(R_{j.1}, R_{j.2}, R_{j.3})$ and a calculation result of (I) in the triangle polygon is expressed as $k_{j.1}, k_{j.2}, k_{j.3}$.

(IIb) When there is no triangle polygon satisfying $0 \leq k_{j.2} + k_{j.3} \leq 1$, $0 \leq k_{j.2}$, and $0 \leq k_{j.3}$, find a polygon which satisfies $0 < k_1$ and "distances from three points $|\overrightarrow{OQ} - \overrightarrow{OR_1}| + |\overrightarrow{OQ} - \overrightarrow{OR_2}| + |\overrightarrow{OQ} - \overrightarrow{OR_3}|$ become minimum". The triangle polygon is expressed as $(R_{j.1}, R_{j.2}, R_{j.3})$ and a calculation result of (I) in the triangle polygon is expressed as $k_{j.1}, K_{j.2}, k_{j.3}$.

(III) Using $k_{j.1}$, the coordinates of the point Ph are calculated.

$$(XhYhZh) = k_{j.1} \cdot (XvYvZv)$$

(2.4.2 Three-Dimensional Head Image→Three-Dimensional Semi-Ellipsoidal Surface)

A point on a three-dimensional head image is made to uniquely correspond to a point on a three-dimensional semi-ellipsoidal surface by the coordinate transformation processing D (S2100). It is assumed that the three-dimensional semi-ellipsoidal surface is a semi-ellipsoidal surface with radii Rvx, Rvy, and Rvz and a central point (0 0 0). It is assumed that the central point of a three-dimensional head image is (0 0 0).

Each coordinate point is expressed as follows.

Point Ov(0 0 0): Central point on a three-dimensional semi-ellipsoid

Point Ph(Xh Yh Zh): point on a three-dimensional head image to be subjected to coordinate transformation processing D Point Pv(Xv Yv Zv): point on a three-dimensional semi-ellipsoidal surface after coordinate transformation of the point Ph by the coordinate transformation processing D The point of intersection of the straight line OvPh and a three-dimensional semi-ellipsoidal surface is defined as a point Pv, and it is calculated as follows.

$$k_1 = \sqrt{\frac{1}{\frac{Xh^2}{Rvx^2} + \frac{Yh^2}{Rvy^2} + \frac{Zh^2}{Rvz^2}}}$$

$$(Xv\ Yv\ Zv) = k_1 \cdot (Xh\ Yh\ Zh)$$

(3. Calculation of Approximation of a Three-Dimensional Head Image to Three-Dimensional Semi-Ellipsoid)

A three-dimensional head image is approximated using a three-dimensional semi-ellipsoid. Although some approximation methods may be considered, three radii Rvx, Rvy, and Rvz of a three-dimensional semi-ellipsoid are simply calculated from a three-dimensional head image in the present embodiment.

The procedure of calculating three radii of a three-dimensional semi-ellipsoid using four points of a right ear $P_{h.R}$, a left ear $P_{h.L}$, the Nasion $P_{h.N}$, and the crown $P_{h.T}$ in a three-dimensional head image will be described using FIG. 16.

Figure 16:
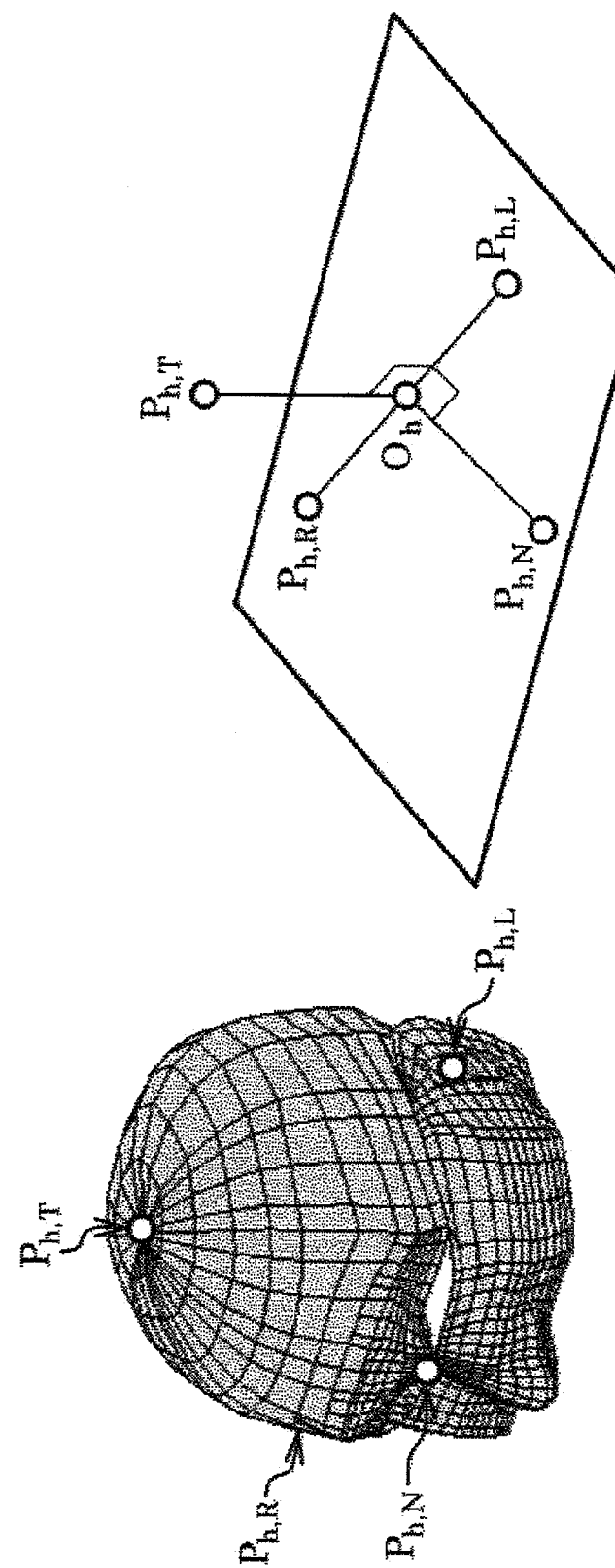
FIG. 16 is a view for explaining the calculation of approximation of a three-dimensional head image to a three-dimensional semi-ellipsoid.

FIG. 16 is a view showing calculation processing of approximating a three-dimensional head image to a three-dimensional semi-ellipsoid.

The midpoint $O_h$ of the right ear $P_{h.R}$ and the left ear $P_{h.L}$ is found, and $\overrightarrow{O_h P_{hR}}$ is set as Rvx. A perpendicular is drawn from Nasion $P_{h.N}$ to the straight line $P_{h.R}P_{h.L}$, a distance between a point of the foot and $P_{h.N}$, and it is set as Rvy. A perpendicular is drawn from the crown $P_{h.T}$ to the plane including the midpoint $O_h$ of the right ear $P_{h.R}$ and the left ear $P_{h.L}$, a distance between a point of the foot and $P_{h.T}$, and it is set as Rvz.

(4. Calculation of the Length of an Ellipse Arc)

Figure 17:
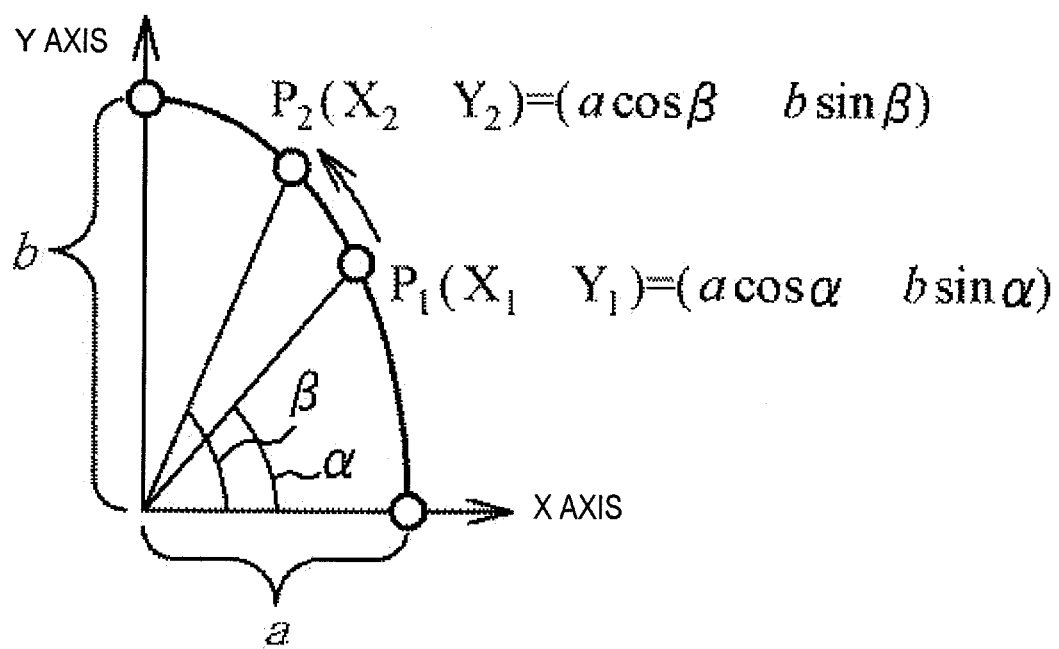
FIG. 17 is a view for explaining a method of calculating the length of an ellipse arc.

A method of calculating the length of an ellipse arc will be described on the basis of FIG. 17. FIG. 17 is a view showing an example of calculating the length of an ellipse arc.

The problem of finding the length of an ellipse arc is known as a problem of calculating an elliptic integral. Since it cannot be calculated by an elementary function, it can be approximately calculated by numerical integration. Although several methods are proposed as numerical integration, the calculation is performed by mensuration by parts using the extended midpoint rule in the present embodiment.

The radii of an ellipse are set to a and b and its center is set (0, 0), and the length L of an arc between two points $P_1(X_1\ Y_1)$ and $P_2(X_2\ Y_2)$ on the ellipse is calculated.

The two points $P_1$ and $P_2$ are expressed as follows using the angles of deflection $\alpha$ and $\beta$ $$P_1(X_1Y_1) = (a \cos \alpha, b \sin \alpha)$$

$$P_2(X_2Y_2) = (a \cos \beta, b \sin \beta)$$

Here, $\alpha < \beta$ is assumed because the universalness is satisfied even if $\alpha < \beta$.

The length L of the arc of the ellipse is expressed by the following definite integral.

$$L = a \int_\alpha^\beta g(\theta) d\theta,$$

$$g(\theta) = \sqrt{1 - \left(1 - \frac{b^2}{a^2}\right)\sin^2\theta}$$

(I) In the case of $$-\frac{\pi}{2} \leq \alpha < \beta \leq \frac{\pi}{2}$$

$$L = a \int_{\sin\alpha}^{\sin\beta} f(x) dx,$$

$$f(x) = \frac{\sqrt{1 - \left(1 - \frac{b^2}{a^2}\right)x^2}}{\sqrt{1 - x^2}}$$

Approximate calculation of this definite integral is performed as follows by mensuration by parts using the extended midpoint rule.

$$L \approx a \sum_{k=0}^{N-1} f\left(x_{k+\frac{1}{2}}\right) \times h$$

N: Division number in mensuration by parts $$h = \frac{\sin\beta - \sin\alpha}{N}$$

$$x_{k+\frac{1}{2}} = \left(k + \frac{1}{2}\right) \times \frac{\sin\beta - \sin\alpha}{N} + \sin\alpha$$

$(k = 0 \text{ to } N - 1)$ (II) Other cases

As shown in the following table, definite integral is decomposed, and the decomposed definite integral is calculated according to approximation calculation of (I).

| Conditions of $\alpha$ | Conditions of $\beta$ | Length of an arc of an ellipse |
|---|---|---|
| $-\pi \le \alpha < -\frac{\pi}{2}$ | $\alpha \le \beta < -\frac{\pi}{2}$ | $L = a \int_\alpha^\beta g(\theta) d\theta = a \int_{\sin(-\beta-\pi)}^{\sin(-\alpha-\pi)} f(x) dx$ |
| | $-\frac{\pi}{2} \le \beta \le \frac{\pi}{2}$ | $L = a \int_\alpha^{-\frac{\pi}{2}} g(\theta) d\theta + a \int_{-\frac{\pi}{2}}^\beta g(\theta) d\theta$ |
| | | $= a \int_{\sin\left(-\frac{\pi}{2}\right)}^{\sin(-\alpha-\pi)} f(x) dx + a \int_{\sin\left(-\frac{\pi}{2}\right)}^{\sin\beta} f(x) dx$ |
| | $\frac{\pi}{2} < \beta \le \pi$ | $L = a \int_\alpha^{-\frac{\pi}{2}} g(\theta) d\theta + a \int_{-\frac{\pi}{2}}^{\frac{\pi}{2}} g(\theta) d\theta + a \int_{\frac{\pi}{2}}^\beta g(\theta) d\theta$ |
| | | $= a \int_{\sin\left(-\frac{\pi}{2}\right)}^{\sin(-\alpha-\pi)} f(x) dx + a \int_{\sin\left(-\frac{\pi}{2}\right)}^{\sin\frac{\pi}{2}} f(x) dx + a \int_{\sin(\pi-\beta)}^{\sin\frac{\pi}{2}} f(x) dx$ |
| $-\frac{\pi}{2} \le \alpha \le \frac{\pi}{2}$ | $\alpha \le \beta \le \frac{\pi}{2}$ | $L = a \int_{\sin\alpha}^{\sin\beta} f(x) dx$ |
| | $\frac{\pi}{2} < \beta \le \pi$ | $L = a \int_\alpha^{\frac{\pi}{2}} g(\theta) d\theta + a \int_{\frac{\pi}{2}}^\beta g(\theta) d\theta$ |
| | | $= a \int_{\sin\alpha}^{\sin\frac{\pi}{2}} f(x) dx + a \int_{\sin(\pi-\beta)}^{\sin\frac{\pi}{2}} f(x) dx$ |
| $\frac{\pi}{2} < \alpha \le \pi$ | $\alpha \le \beta \le \pi$ | $L = a \int_\alpha^\beta g(\theta) d\theta = a \int_{\sin(\pi-\beta)}^{\sin(\pi-\alpha)} f(x) dx$ |

(5. Calculation of the Point Coordinates at which the Length of an Ellipse Arc Becomes a Designated Distance)

A method of calculating the point coordinates which are away from a certain point on an ellipse by a designated distance will be described on the basis of FIG. 17.

The coordinates of the point $P_2$ at which the distance on the ellipse to the point $P_1$ is L are calculated.

The point $P_1$ is expressed as follows using $\alpha$.

$P_1(X_1 Y_1) = (a \cos \alpha, b \sin \alpha)$

On the other hand, the point $P_2$ is expressed as follows using the angle of deflection $\beta$.

$P_2(X_2 Y_2) = (a \cos \beta, b \sin \beta)$

In addition, the angle of deflection $\beta$ is calculated.

Here, $\alpha < \beta$ and $a < b$ are assumed because the universalness is satisfied even if $\alpha < \beta 0$ and $a < b$.

As previously described, since the length of an ellipse arc cannot be calculated in a deductive way, it is calculated by approximation calculation. Therefore, the length of an ellipse arc is calculated for the candidate value of the angle of deflection $\beta$ in a possible range and the angle of deflection which is closest to the designated distance is adopted. Specifically, the calculation is performed as follows.

(i) The range of a value that the angle of deflection $\beta$ can have is as follows.

$$\alpha + \frac{L}{b} < \beta < \alpha + \frac{L}{a}$$

(ii) The candidate value of $\beta$ is generated by dividing the range of the possible value by an appropriate division number N.

Candidate value of $\beta$ $$\alpha + \frac{L}{b} + h \cdot 1, \alpha + \frac{L}{b} + h \cdot 2 \ldots, \alpha + \frac{L}{b} + h \cdot (N-1)$$

$$\left(\text{Here, } h = \frac{1}{N}\left(\frac{L}{a} - \frac{L}{b}\right)\right)$$

(iii) The length of the ellipse arc is calculated for each candidate value of $\beta$, and the value closest to the designated distance L is set as $\beta$.

(6. Actual Calculation Processing)

Hereinafter, the procedure of calculating a light irradiation position and a light detection position (S2110) on a three-dimensional head image on the basis of the probe position (S2010) on a two-dimensional head image set on the software by the user will be described.

(Calculation Processing A of Calculating a Light Irradiation Position and a Light Detection Position from the Coordinate Position of the Probe Center (S2080))

Figure 18:
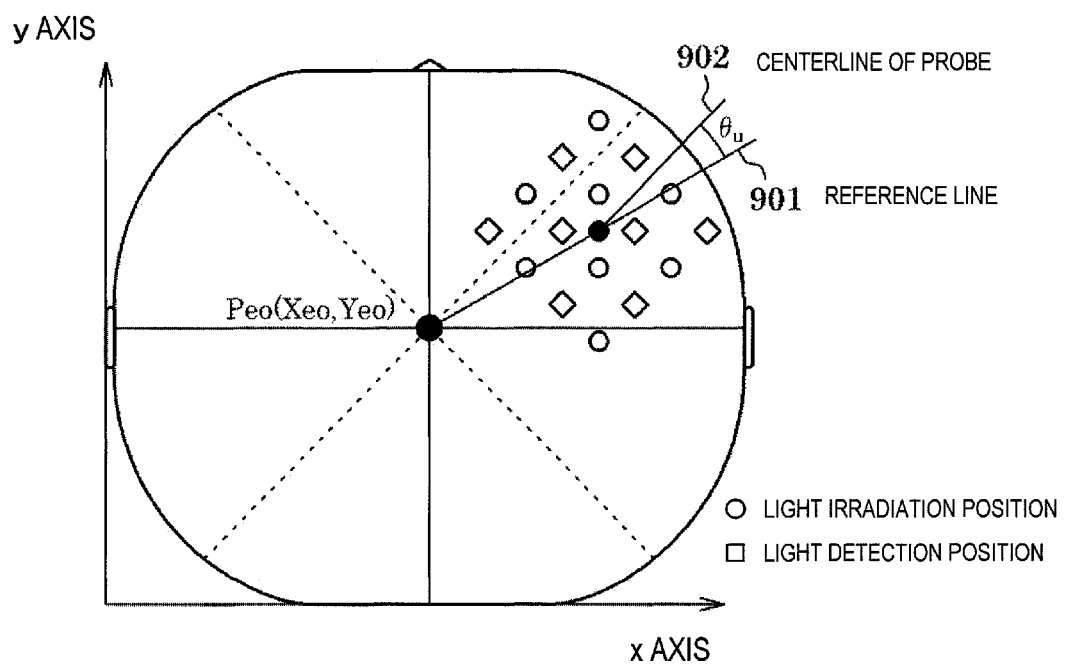
FIG. 18 is a view for explaining the setting of a probe position on a two-dimensional head image.
Figure 19:
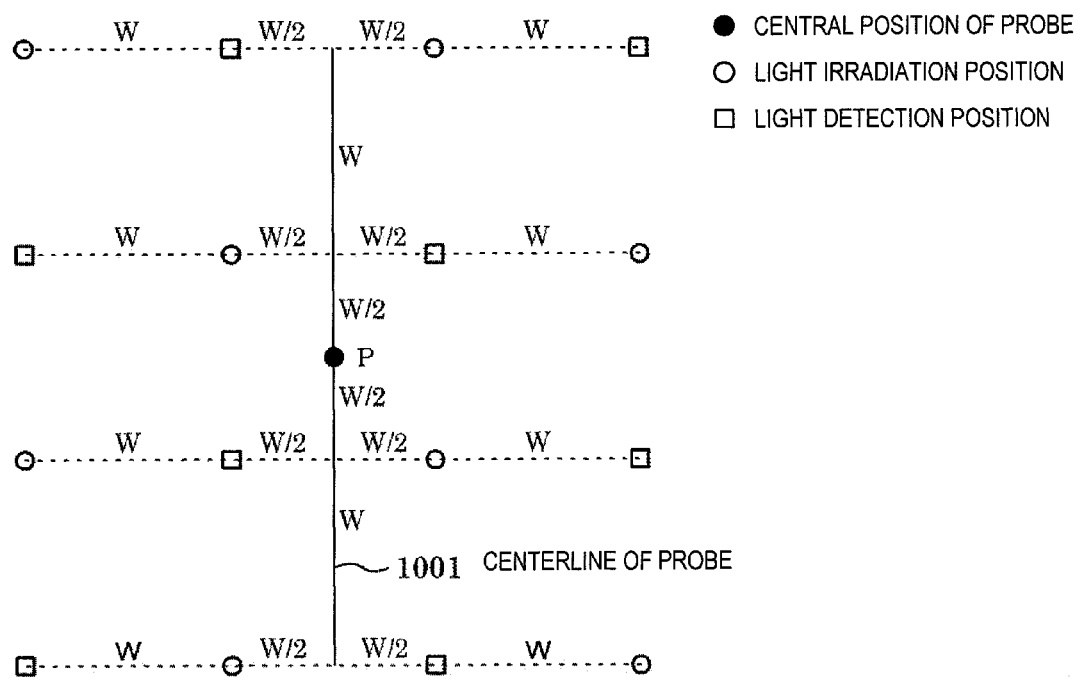
FIG. 19 is a view for explaining the shape information of a probe on the two-dimensional plane.
Figure 20:
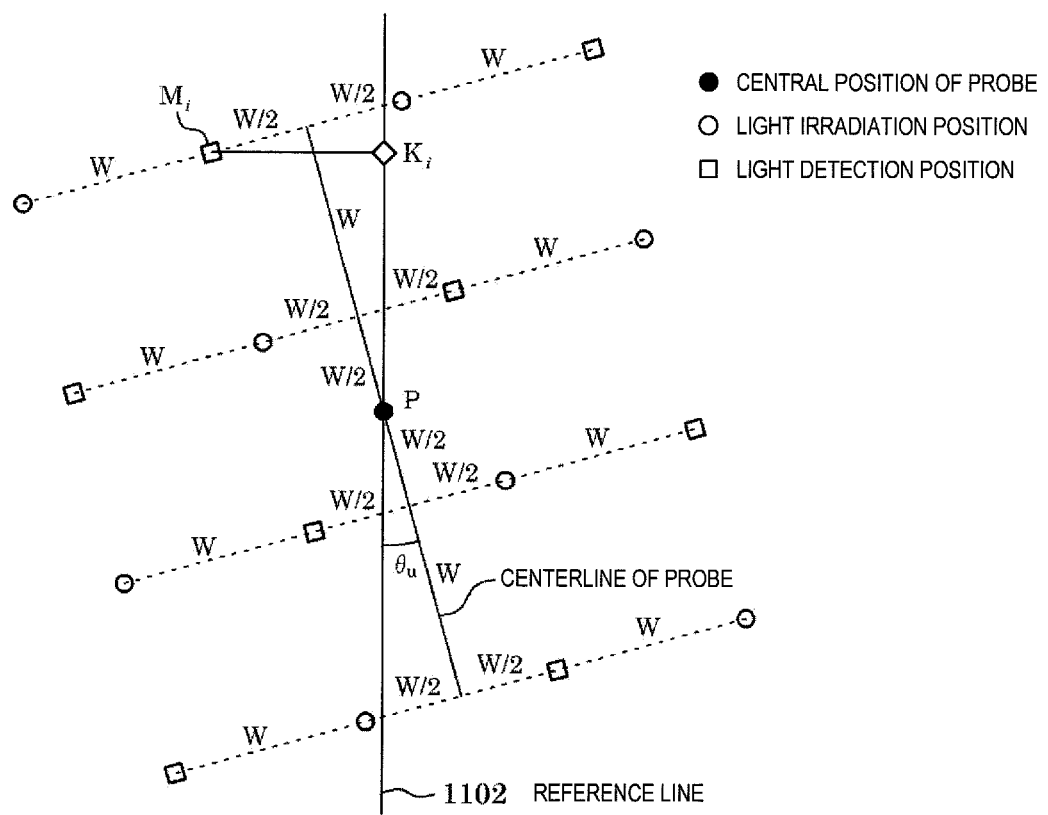
FIG. 20 is a view for explaining the shape information of a probe on the two-dimensional plane.

The calculation processing A (S2080) will be described below using FIGS. 18, 19, and 20. FIG. 18 is a view explaining an example of setting the probe position on a two-dimensional head image, FIG. 19 is a view explaining the shape information (before rotation) regarding a probe on a two-dimensional plane, and FIG. 20 is a view explaining the shape information (after rotation) regarding a probe on a two-dimensional plane.

A light irradiation position and a light detection position on a three-dimensional semi-ellipsoidal surface are calculated from the coordinate position of the probe center on the three-dimensional semi-ellipsoidal surface.

In the present embodiment, it is assumed that a probe on a two-dimensional head image is disposed as shown in FIG. 18, for example.

The inclination of a reference line (901) which connects the central point of a probe and the central point of a two-dimensional head image is set to $\alpha_u$, and the inclination of a centerline (902) of the probe with respect to the reference line (901) is set to $\theta_u$.

In order to calculate a light irradiation position and a light detection position on the three-dimensional semi-ellipsoidal surface from the coordinate position of the probe center on the three-dimensional semi-ellipsoidal surface, the information regarding the relationship between the probe center and the light irradiation position and the light detection position in the probe is used as known probe shape information.

As the probe shape information, it is usually preferable to assume a sheet-like probe, in which a certain fixed number of light irradiation positions and light detection positions are mixed together, and to use the shape information.

It is very difficult to make a probe with a shape, which completely matches the head shape, due to individual difference of the head shape of a subject body or shape difference depending on a fixing position. Usually, a probe with a shape, which matches the head shapes of many subject bodies in a possible range, is used.

In the present embodiment, the calculation processing A (S2080) in the case where two of the shape on the two-dimensional plane and the shape disposed on the three-dimensional spherical surface are assumed as the probe shape information will be described.

(6.1. Case where a Shape on a Two-Dimensional Plane is Used)

First, the case is assumed in which each light irradiation position and each light detection position are arrayed on the sheet shape on the two-dimensional plane as the probe shape information. For example, it is assumed that the shape information shown in FIG. 19 is used as the probe shape information. All distances between the light irradiation positions and the light detection positions were set to W.

The coordinates of the central position of the probe on the two-dimensional plane is set to (0 0).

The coordinate points of N light irradiation positions and N light detection positions on the two-dimensional plane are set to $M_1(x_1 \ y_1), \ldots, M_i(x_i \ y_i) \ldots, M_N(x_N \ y_N)$.

Then, rotation of the probe set on the two-dimensional head image is reflected in the probe shape information on the two-dimensional plane. The coordinate points of the N light irradiation positions and the N light detection positions on the two-dimensional plane are as follows, as shown in FIG. 20.

$M_1(x_1 \cos\theta_u - y_1 \sin\theta_u, x_1 \sin\theta_u + y_1 \cos\theta_u)$ $M_i(x_i \cos\theta_u - y_i \sin\theta_u, x_i \sin\theta_u + y_i \cos\theta_u)$ $M_N(x_N \cos\theta_u - y_N \sin\theta_u, x_N \sin\theta_u + y_N \cos\theta_u)$ For a reference line passing through the central line of the probe, perpendiculars are drawn from each light irradiation position and each light detection position. Each foot of the perpendiculars is set as a reference point.

$K_1(0 x_1 \sin\theta_u + y_1 \cos\theta_u), \ldots, K_i(0 x_i \sin\theta_u + y_i \cos\theta_u), \ldots, K_N(0 x_N \sin\theta_u + y_N \cos\theta_u)$ When calculating each light irradiation position and each light detection position on the three-dimensional semi-ellipsoid, a distance (expression 2) from the center of a probe to a reference point and a distance (expression 3) from the reference point to each light irradiation position and each light detection position are used from the shape information of the probe.

$\overline{PK_1}, \ldots \overline{PK_i}, \ldots, \overline{PK_N}$ (Expression 2)

$\overline{K_1M_1}, \ldots \overline{K_iM_i}, \ldots, \overline{K_NM_N}$ (Expression 3)

In order to calculate the position of $M_i$ on the three-dimensional semi-ellipsoid, the following two steps of calculation are performed.

(I) Along the reference line on the three-dimensional semi-ellipsoid, the coordinates of the reference point $K_i$ on the three-dimensional semi-ellipsoid, at which the distance on the three-dimensional semi-ellipsoid from the central point of the probe on the three-dimensional semi-ellipsoid becomes (expression 4), are calculated.

(II) A coordinate point at which the distance on the three-dimensional semi-ellipsoid from the reference point $K_i$ on the three-dimensional semi-ellipsoid becomes (expression 5) is calculated, and this is set as $M_i$ on the three-dimensional semi-ellipsoid.

$\overline{PK_i}$ (Expression 4)

$\overline{K_iM_i}$ (Expression 5)

Hereinafter, details of calculation processing of (I) and (II) will be described.

(I) The coordinates of the reference point $K_i$ on the three-dimensional semi-ellipsoid are calculated.

Figure 21:
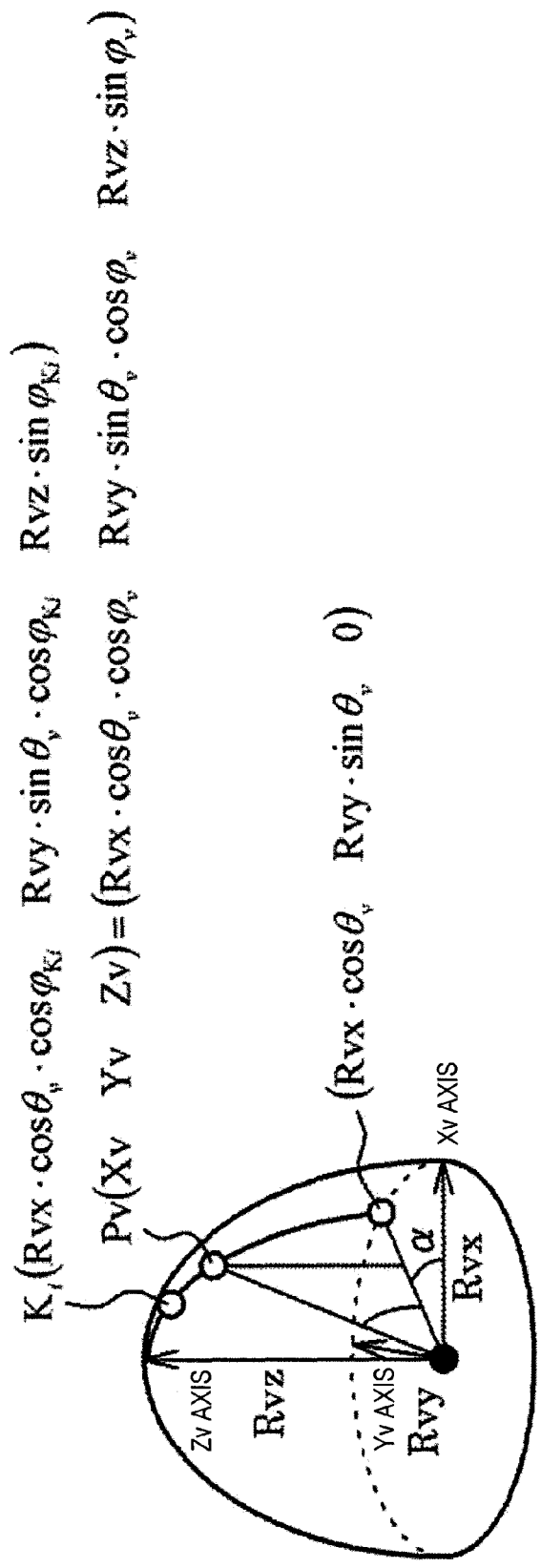
FIG. 21 is a view for explaining a method of calculating the coordinate position of a reference point.
Figure 22:
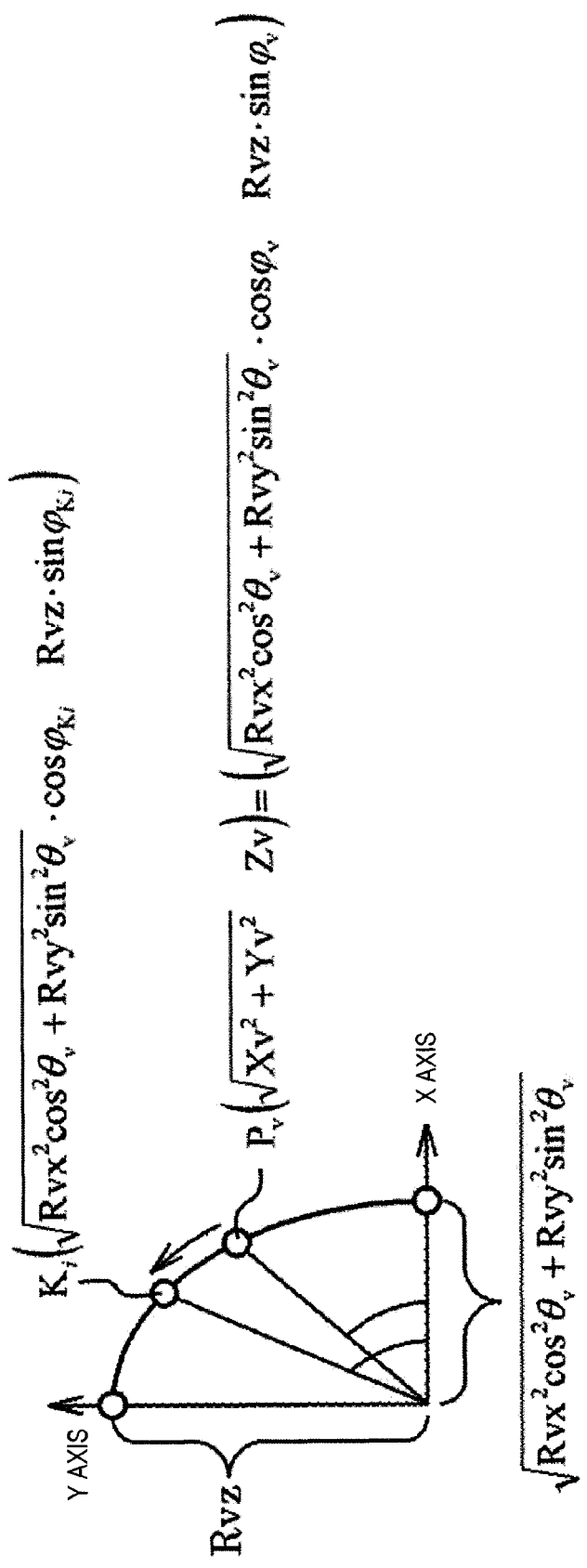
FIG. 22 is a view for explaining a method of calculating the coordinate position of a reference point.

The procedure of calculating the reference point $K_i$ as a point on the reference line passing through the central point Pv of a probe on a three-dimensional semi-ellipsoid and the apex of a semi-ellipsoid will be described using FIGS. 21 and 22. FIG. 21 is a view explaining the calculation (three-dimensional semi-ellipsoid) of the coordinate position of a reference point, and FIG. 22 is a view explaining the calculation (cut ellipsoid S1) of the coordinate position of a reference point.

In FIG. 21, the central point Pv of a probe is expressed as follows.

$Pv(Xv Yv Zv) = (Rvx \cdot \cos\theta_v \cdot \cos\phi_v, Rvy \cdot \sin\theta_v \cdot \cos\phi_v, Rvz \cdot \sin\phi_v)$ Here, $\theta_v$ and $\phi_v$ are angles of deflection in polar coordinate expression and are calculated as follows.

$$\varphi_v = \arcsin\left(\frac{Zv}{Rvz}\right)$$

-continued

If $Yv \geq 0$, $\theta_v = \arccos\left(\dfrac{Xv}{Rvx \times \cos\varphi_v}\right)(0 \leq \theta_v \leq \pi)$ If $Yv < 0$, $\theta_v = -\arccos\left(\dfrac{Xv}{Rvx \times \cos\varphi_v}\right)(-\pi \leq \theta_v \leq 0)$ The reference point $K_i$ can be expressed using the angle of deflection $\phi_{Ki}$ and $K_i(X_i Y_i Z_i)=(Rvx\cdot\cos\theta_v\cdot\cos\phi_{Ki}$ $Rvy\cdot\sin\theta_v\cdot\cos\phi_{Ki}$ $Rvz\cdot\sin\phi_{Ki})$ as a point on the reference line.

On an ellipse formed on a cut plane including the reference line passing through the apex of a semi-ellipsoid and the central point Pv of the probe on the three-dimensional semi-ellipsoid, a point at which the distance from the central point Pv of the probe becomes (expression 4) is calculated. (refer to FIG. 22)

On the cut ellipsoidal surface $S_1$, the points Pv and $K_i$ are expressed as follows.

$$Pv\left(\sqrt{Xv^2 + Yv^2}\ Zv\right) = \left(\sqrt{Rvx^2\cos^2\theta_v + Rvy^2\sin^2\theta_v}\ \cdot\cos\varphi_v, Rvz\cdot\sin\varphi_v\right)$$

$$K_i\left(\sqrt{Rvx^2\cos^2\theta_v + Rvy^2\sin^2\theta_v}\ \cdot\cos\varphi_{Ki}, Rvz\cdot\sin\varphi_{Ki}\right)$$

On the other hand, the reference point $K_i$ at which the distance from the central point Pv of the probe becomes (expression 4) is calculated by calculating the angle of deflection $\psi_{Ki}$ using the "calculation of the point coordinates at which the length of an ellipse arc becomes a designated distance" method described previously.

Moreover, here, the angle $\alpha$ between the Xv axis and a line segment, which is obtained by projecting the reference line to the XvYv coordinate plane, is calculated as follows.

(1) In the case of $(Xv\ Yv) \neq (0\ 0)$ $$\alpha = \arccos\left(\dfrac{Xv}{\sqrt{Xv^2 + Yv^2}}\right)$$

is calculated if $Yv \geq 0$, and $$\alpha = -\arccos\left(\dfrac{Xv}{\sqrt{Xv^2 + Yv^2}}\right)$$

is calculated if $Yv < 0$ (2) In the case of $(Xv\ Yv)=(0\ 0)$, $\alpha=\theta_u$ is calculated.

(II) The coordinates of $M_i$ on the three-dimensional semi-ellipsoid are calculated.

A method of calculating the coordinates of $M_i$ on the three-dimensional semi-ellipsoid will be described below.

The point $M_i$ is calculated as a point, at which the distance from the reference point $K_i$ becomes (expression 5), on the curve (curve $L_2$) formed as a line of intersection of an ellipsoid and a cross section (cross section $S_2$) which is perpendicular to the "tangential plane at the point $K_i$ on the ellipsoid" and which is perpendicular to the "cross section (cross section $S_1$) perpendicular to the bottom surface of the ellipsoid passing through the point $K_i$". The calculation procedure is as follows.

(i) Find the expression of the tangential line $L_1$ at the point $K_i$, which is included in the cross section $S_1$, to the ellipsoid.
(ii) Find the expression of the cross section $S_2$.
(iii) Find the expression of the curve $L_2$.
(iv) Find a point, at which the distance from the reference point $K_i$ becomes (expression 5), on the curve $L_2$.

Details of each calculation procedure differ depending on the coordinate value (expression 6) of the reference point $K_i$.

$$(X_{Ki} Y_{Ki} Z_{Ki}) \quad \text{(Expression 6)}$$

The coordinate value of the reference point $K_i$ is related to each of the following six conditions, and details of the calculation procedures (i) to (iv) will be described below.

Condition 1    $X_{Ki} \neq 0$, $Y_{Ki} \neq 0$, $Z_{Ki} \neq 0$

Condition 2    $X_{Ki} \neq 0$, $Y_{Ki} = 0$, $Z_{Ki} \neq 0$

Condition 3    $Z_{Ki} = 0$

Condition 4    $X_{Ki} = 0$, $Y_{Ki} \neq 0$, $Z_{Ki} \neq 0$

Condition 5    $X_{Ki} = 0$, $Y_{Ki} = 0$, $\alpha \neq \pm\dfrac{\pi}{2}$

Condition 6    $X_{Ki} = 0$, $Y_{Ki} = 0$, $\alpha = \pm\dfrac{\pi}{2}$ (1) In the case of condition 1

$(X_{Ki} \neq 0, Y_{Ki} \neq 0, Z_{Ki} \neq 0)$ (i) Find the expression of the tangential line $L_1$ at the point $K_i$, which is included in the cross section $S_1$, to the ellipsoid.

Figure 23:
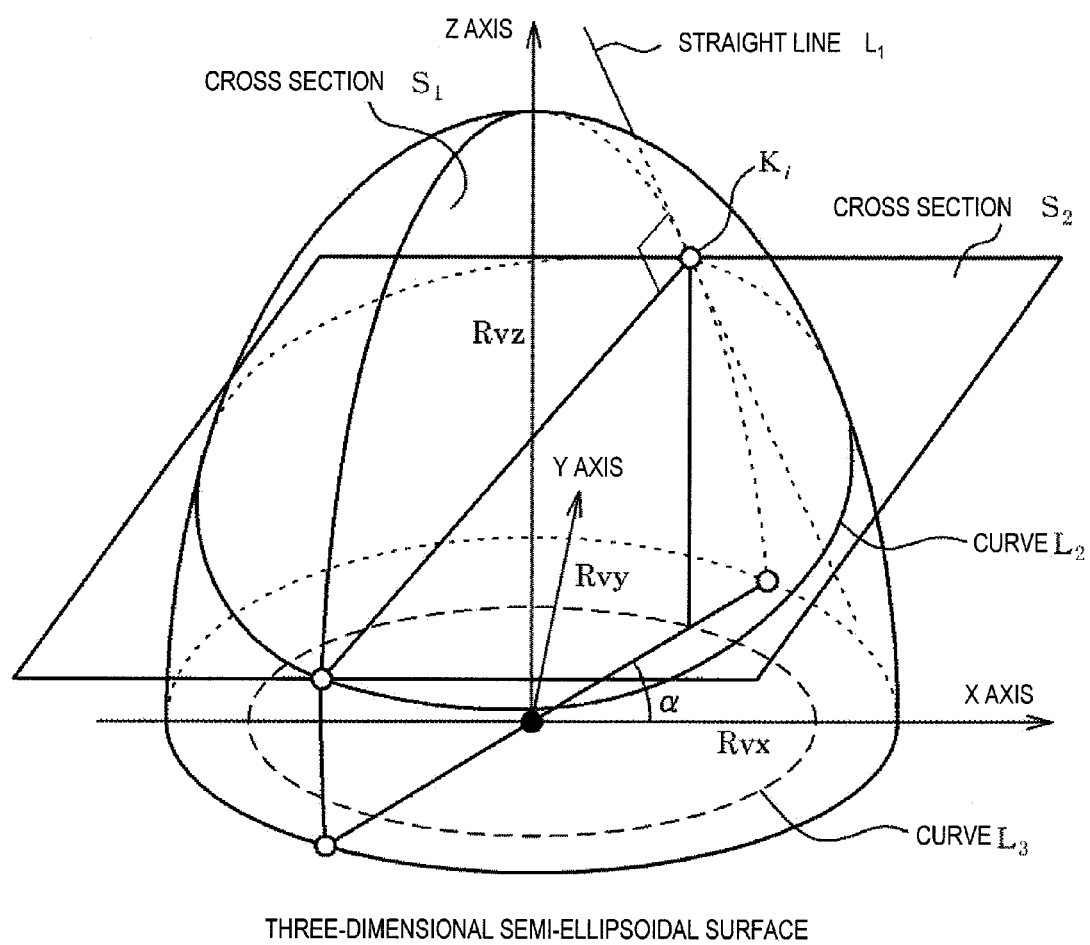
FIG. 23 is a view for explaining a calculation method of expressions of a cross section and a straight line and a curve on the three-dimensional semi-ellipsoid in condition 1.
Figure 24:
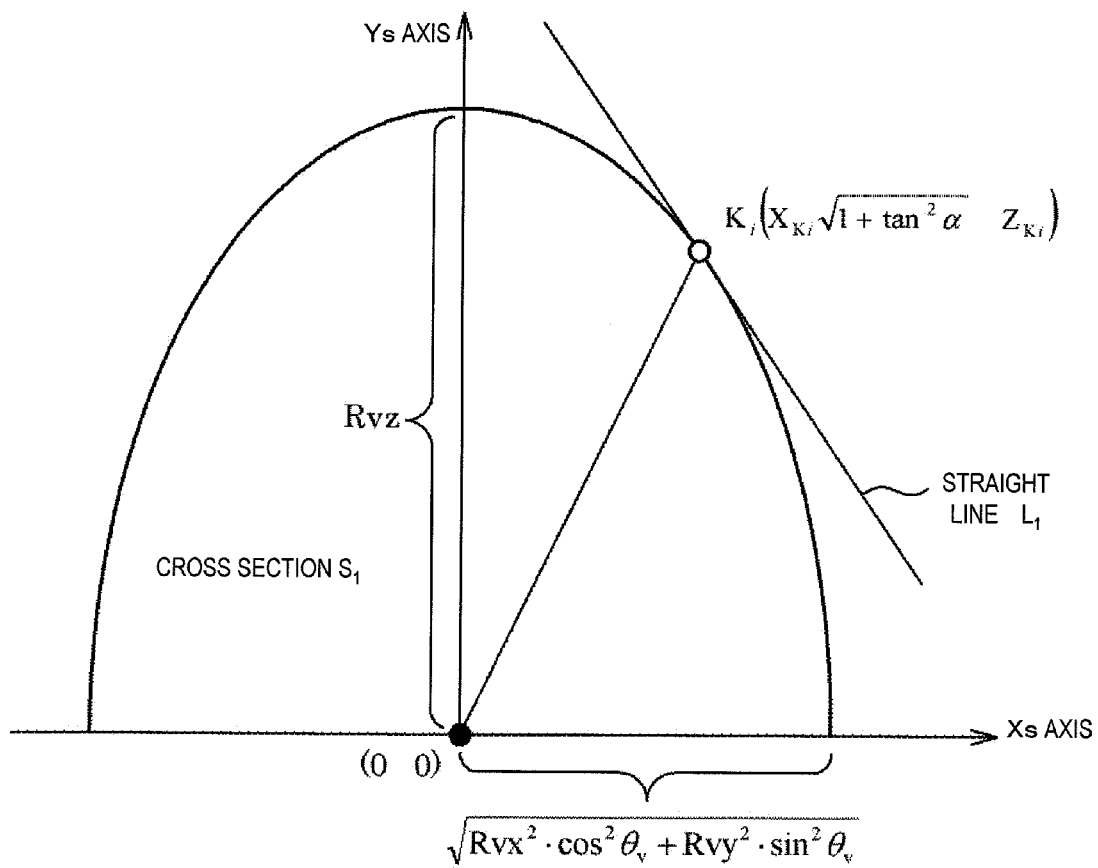
FIG. 24 is a view for explaining a calculation method of the expression of a straight line L1 on a cross section S1 in condition 1.

As shown in FIG. 24, the cross section $S_1$ shown in FIG. 23 becomes a semi-elliptical shape with radii of ($\sqrt{Rvx^2\cdot\cos^2\theta_v + Rvy^2\cdot\sin^2\theta_v}$) and Rvz.

In the XsYs coordinate system on the cross section $S_1$, the point $K_i$ is expressed as follows.

$$\text{Point } K_i(X_{Ki}\sqrt{1+\tan^2\alpha}\ Z_{Ki})$$

The straight line $L_1$ in the XsYs coordinate system on the cross section $S_1$ is expressed as follows.

$$\dfrac{X_S \cdot X_K \sqrt{1+\tan^2\alpha}}{Rvx^2 \cdot \cos^2\theta_v + Rvy^2 \cdot \sin^2\theta_v} + \dfrac{Y_s \cdot Z_K}{Rvz^2} = 1$$

In addition, FIG. 23 is a view showing the relationship of the curves L1, L2, and L3 and the cross sections S1 and S2 on the three-dimensional semi-ellipsoid in the condition 1, and FIG. 24 is a view showing the straight line $L_1$ on the cross section S1 in the condition 1.

The following relational expressions are satisfied between the coordinate system on the cross section $S_1$ shown in FIG. 24 and the three-dimensional coordinate system shown in FIG. 23.

$$X_s = X\sqrt{1+\tan^2\alpha}$$

$$Y_s = Z$$

$$Y = X\cdot\tan\alpha$$

Taking the above into consideration, the following is obtained.

$$Y = X \cdot \tan\alpha$$

$$\text{Straight line } L_1 \quad \dfrac{X \cdot X_K}{Rvx^2 \cdot \cos^2\theta_K} + \dfrac{Z \cdot Z_K}{Rvz^2} = 1$$

(ii) Find the expression of the cross section $S_2$.

As shown in FIG. 23, as a plane perpendicular to the straight line $L_1$, the cross section $S_2$ is calculated as follows.

Cross section $S_2(X-X_{Ki})+h_2 \cdot (Y-Y_{Ki})-h_3 \cdot (Z-Z_{Ki})=0$

Here, $h_2 = \tan \alpha$ $$h_3 = \frac{Rvz}{Rvx} \cdot \frac{1}{\cos\theta_v \cdot \tan\varphi_{Ki}}$$

(iii) Find the expression of the curve $L_2$.
The expression of the ellipsoid becomes as follows.

$$\frac{X^2}{Rvx^2} + \frac{Y^2}{Rvy^2} + \frac{Z^2}{Rvz^2} = 1$$

Here, the expression of the cross section $S_2$ found previously is changed.

$$Z = \frac{X - X_{Ki}}{h_3} + \frac{h_2 \cdot (Y - Y_{Ki})}{h_3} + Z_{Ki}$$

This expression of the cross section $S_2$ is substituted into the expression of the ellipsoid to find a cross-sectional line formed by the line of intersection of the cross section $S_2$ and the ellipsoid.

$$\frac{X^2}{Rvx^2} + \frac{Y^2}{Rvy^2} + \frac{\left(\frac{X-X_{Ki}}{h_3} + \frac{h_2 \cdot (Y-Y_{Ki})}{h_3} + Z_{Ki}\right)^2}{Rvz^2} = 1$$

Figure 25:
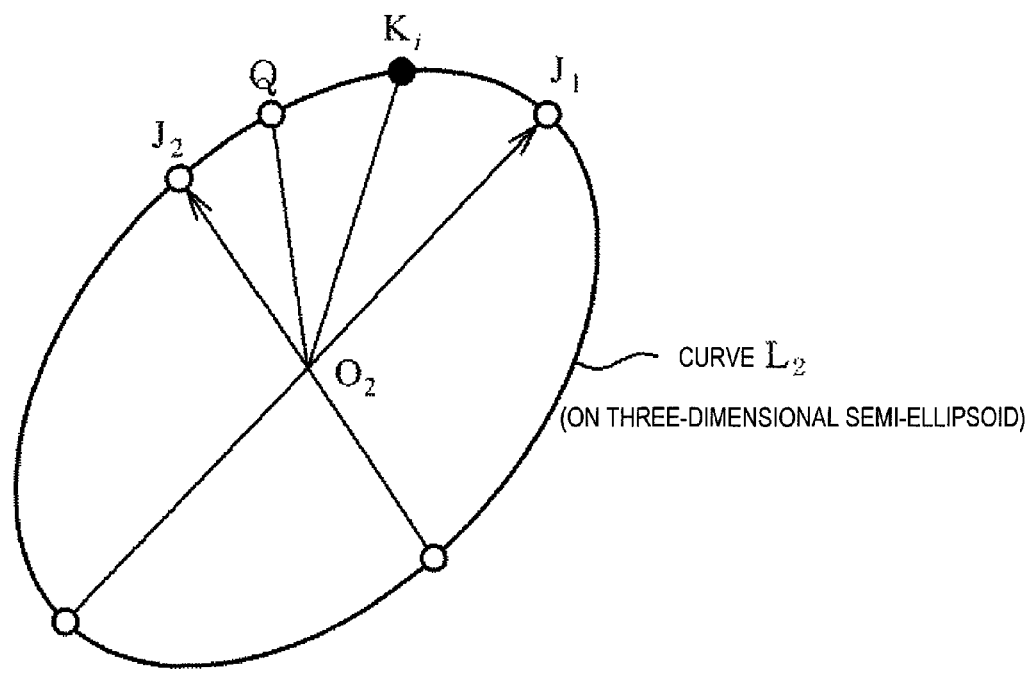
FIG. 25 is a view for explaining a calculation method of curves L2 and L3 in condition 1.
Figure 25:
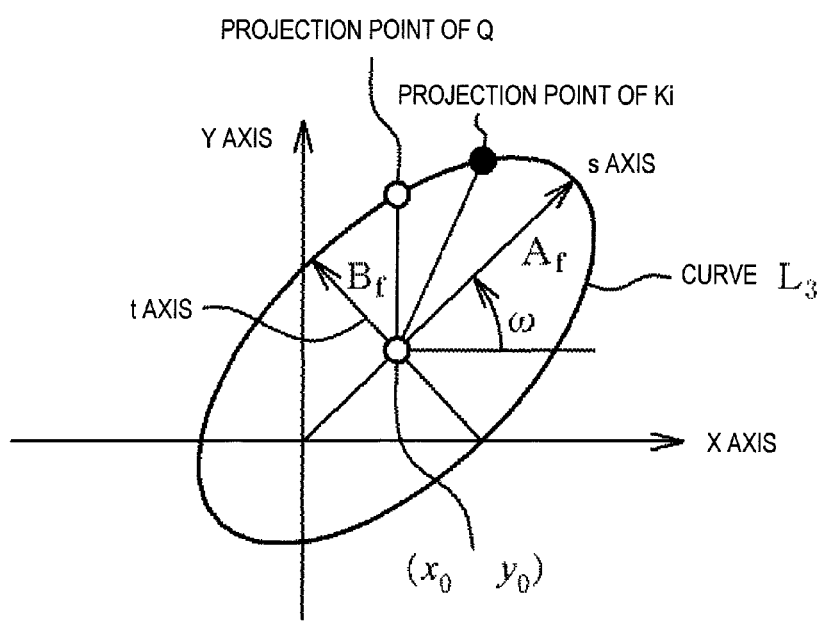

After changing the above expression, the following expression is obtained. The following expression indicates a curve $L_3$ which is defined by projecting the curve $L_2$ on the XY plane, and is shown in FIGS. 23 and 25. FIG. 25 is a view showing the relationship between the curve L2 on the three-dimensional semi-ellipsoid and the curve L3 on the XY plane in the condition 1.

$$\frac{s^2}{A_f^2} + \frac{t^2}{B_f^2} = 1$$

$$\begin{pmatrix} s \\ t \end{pmatrix} = \begin{pmatrix} \cos\omega & -\sin\omega \\ \sin\omega & \cos\omega \end{pmatrix} \begin{pmatrix} X - x_0 \\ Y - y_0 \end{pmatrix}$$

$$m_1 = \frac{Rvz^2 \cdot h_3^2}{Rvx^2} + 1$$

$$m_2 = \frac{Rvz^2 \cdot h_3^2}{Rvy^2} + h_2^2$$

$$m_3 = 2(X_K + h_2 Y_K - h_3 Z_K)$$

$$m_4 = (X_K + h_2 Y_K - h_3 Z_K)^2 - Rvz^2 \cdot h_3^2$$

$$m_5 = m_1 x_0^2 + m_2 y_0^2 + 2h_2 x_0 y_0 - m_4$$

$$x_0 = \frac{m_3(m_2 - h_2^2)}{2(m_1 m_2 - h_2^2)},$$

$$y_0 = \frac{m_3 h_2 (m_1 - 1)}{2(m_1 m_2 - h_2^2)}$$

In the case of $h_2 \geq 0$, $$\phi = \arccos\left(\frac{m_1 - m_2}{\sqrt{(m_1 - m_2)^2 + 4h_2^2}}\right)$$

$(0 \leq \phi \leq \pi)$

In the case of $h_2 < 0$, $$\phi = -\arccos\left(\frac{m_1 - m_2}{\sqrt{(m_1 - m_2)^2 + 4h_2^2}}\right)$$

$(-\pi \leq \phi \leq 0)$ $$\omega = -\frac{\phi}{2} \left(-\frac{\pi}{2} \leq \omega \leq \frac{\pi}{2}\right)$$

$$A_f = \sqrt{\frac{m_5}{m_1 \cos^2\omega + m_2 \sin^2\omega - 2h_2 \cdot \sin\omega \cdot \cos\omega}}$$

$$B_f = \sqrt{\frac{m_5}{m_1 \sin^2\omega + m_2 \cos^2\omega + 2h_2 \cdot \sin\omega \cdot \cos\omega}}$$

Using the above, the arbitrary point Q on the curve $L_2$ is expressed as follows.

$$\begin{pmatrix} X_Q \\ Y_Q \\ Z_Q \end{pmatrix} = \begin{pmatrix} A_f \cos\theta_Q \cos\omega + B_f \sin\theta_Q \sin\omega + x_0 - \\ A_f \cos\theta_Q \sin\omega + B_f \sin\theta_Q \cos\omega + y_0 \\ A_f \cos\theta_Q \cos\omega + B_f \sin\theta_Q \sin\omega + x_0 + \\ h_2(-A_f \cos\theta_Q \sin\omega + B_f \sin\theta_Q \cos\omega - y_0) - \\ \dfrac{(X_I + h_z Y_I - h_3 Z_I)}{h_3} \end{pmatrix}$$

Here, the parameter $\theta_Q$ was defined in the curve $L_3$ obtained by projecting the curve $L_2$ on the XY plan, as shown in FIG. 25.

(iv) Find a point, at which the distance from the reference point $K_i$ becomes (expression 5), on the curve $L_2$.

(1) A parameter $\theta_s$ in the expression of the coordinates of the point $K_i$ on the curve $L_2$ is calculated.

$$\begin{pmatrix} s_{Ki} \\ t_{Ki} \end{pmatrix} = \begin{pmatrix} (X_{Ki} - x_0)\cos\omega - (Y_{Ki} - y_0)\sin\omega \\ (X_{Ki} - x_0)\sin\omega + (Y_{Ki} - y_0)\cos\omega \end{pmatrix}$$

In the case of $t_{Kj} \geq 0$, $$\theta_S = \arccos\left(\frac{s_{Ki}}{A_f}\right)$$

$(0 \leq \theta_S \leq \pi)$

In the case of $t_{Kj} < 0$, $$\theta_S = -\arccos\left(\frac{s_{Ki}}{A_f}\right)$$

$(-\pi \leq \theta_S \leq 0)$ (2) Coordinates of a point $O_2$ obtained by projecting the central point of the curve $L_3$ to the cross section $S_2$ and coordinates of two points $J_1$ and $J_2$ on the curve $L_2$ are calculated, and $|\overrightarrow{O_2J_1}|$, $|\overrightarrow{O_2J_2}|$, and $\overrightarrow{O_2J_1} \cdot \overrightarrow{O_2J_2}$ are calculated.

$$\text{Point } O_2 \begin{pmatrix} x_0 \\ y_0 \\ \dfrac{x_0 + h_2 \cdot y_0 - (X_{Ki} + h_2 \cdot Y_{Ki} - h_3 Z_{Ki})}{h_3} \end{pmatrix}$$

$$\text{Point } J_3 \begin{pmatrix} A_f \cos\omega + x_0 \\ -A_f \sin\omega + y_0 \\ \dfrac{A_f \cos\omega + x_0 + h_2 \cdot (-A_f \sin\omega + y_0) - (X_{Ki} + h_2 \cdot Y_{Ki} - h_3 Z_{Ki})}{h_3} \end{pmatrix}$$

$$\text{Point } J2 \begin{pmatrix} B_f \sin\omega + x \\ B_f \cos\omega + y_0 \\ \dfrac{B_f \sin\omega + x_0 + h_2 \cdot (B_f \cos\omega + y_0) - (X_{Ki} + h_2 \cdot Y_{Ki} - h_3 Z_{Ki})}{h_3} \end{pmatrix}$$

$$|\overrightarrow{O_2J_1}| = A_f \sqrt{1 + \left(\dfrac{\cos\omega - h_2\sin\omega}{h_3}\right)^2},$$

$$|\overrightarrow{O_2J_2}| = B_f \sqrt{1 + \left(\dfrac{\sin\omega + h_2\cos\omega}{h_3}\right)^2}$$

$$\overrightarrow{O_2J_1} \cdot \overrightarrow{O_2J_2} = \dfrac{A_f B_f}{h_3}(\sin\omega\cos\omega(1-h_2^2) + h_2(\cos^2\omega - \sin^2\omega))$$

(3) The minimum value $|\overrightarrow{O_2Q}|_{min}$ and the maximum value $|\overrightarrow{O_2Q}|_{max}$ of $|\overrightarrow{O_2Q}|$ are calculated.

Figure 36:
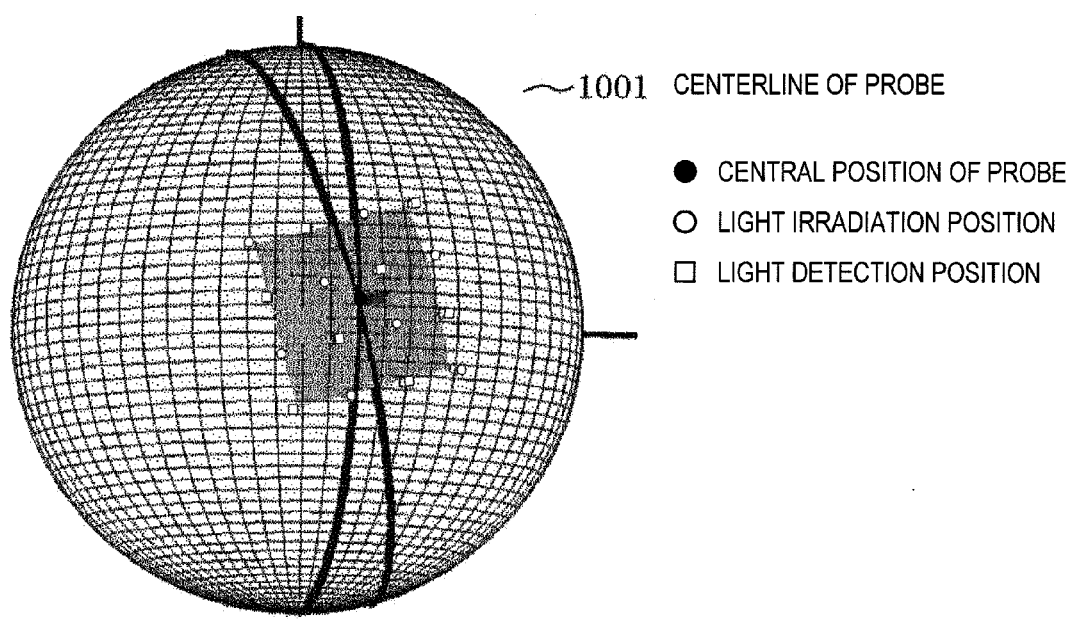
FIG. 36 is a view for explaining the shape of a probe disposed on the three-dimensional spherical surface.

(i) In the case of $|\overrightarrow{O_2J_1}| \geq |\overrightarrow{O_2J_2}|$ $|\overrightarrow{O_2Q}|_{min} = \max(\sqrt{|\overrightarrow{O_2J_2}|^2 - |\overrightarrow{O_2J_1} \cdot \overrightarrow{O_2J_2}|}, 0)$ $|\overrightarrow{O_2Q}|_{max} = \sqrt{2}|\overrightarrow{O_2J_1}|$ (ii) n the case of $|\overrightarrow{O_2J_1}| < |\overrightarrow{O_2J_2}|$ $|\overrightarrow{O_2Q}|_{min} = \max(\sqrt{|\overrightarrow{O_2J_1}|^2 - |\overrightarrow{O_2J_1} \cdot \overrightarrow{O_2J_2}|}, 0)$ $|\overrightarrow{O_2Q}|_{max} = \sqrt{2}|\overrightarrow{O_2J_2}|$ (4) $\theta_Q$ obtained when the length Ld of an arc on the curve $L_2$ between the point $K_i$ and the point Q becomes a designated distance $\overline{K_iM_i}$ in the counterclockwise direction in FIG. 36 is in the following range.

$$\theta_S + \dfrac{\overline{K_iM_i}}{|\overrightarrow{O_2Q}_{max}|} \leq \theta_Q \leq \theta_S + \dfrac{\overline{K_iM_i}}{|\overrightarrow{O_2Q}_{min}|}$$

(5) The length Ld of the arc on the curve $L_2$ between point $K_i$ and the point Q can be calculated according to the following expression.

$$Ld = \int_{\theta_S}^{\theta_Q} \sqrt{\left(\dfrac{dX}{d\theta}\right)^2 + \left(\dfrac{dY}{d\theta}\right)^2 + \left(\dfrac{dZ}{d\theta}\right)^2}\, d\theta$$

$Ld =$ $$\int_{\theta_S}^{\theta_Q} \sqrt{\begin{array}{c} A_f^2 \sin^2\theta + B_f^2 \cos^2\theta + \\ A_f^2\sin^2\theta\dfrac{(-\cos\omega + h_2\sin\omega)^2}{h_3^2} + B_f^2\cos^2\theta\dfrac{(\sin\omega + h_2\cos\omega)^2}{h_3^2} + \\ 2A_f B_f \sin\theta\cos\theta\dfrac{(-\cos\omega + h_2\sin\omega)(\sin\omega + h_2\cos\omega)}{h_3^2} \end{array}}\, d\theta$$

By this definite integral, it is not possible acquire a solution in a deductive way. Therefore, the solution can be approximately calculated by mensuration by parts using the extended midpoint rule. In the extended midpoint rule, the calculation is performed as follows using an appropriate division number N.

$$Ld = \sum_{j=0}^{N-1} f\left(\theta_{j+\frac{1}{2}}\right) \times h$$

$$\theta_{j+\frac{1}{2}} = \left(j + \dfrac{1}{2}\right) \times \dfrac{\theta_Q - \theta_S}{N} + \theta_S \quad (j = 0 \text{ to } N-1)$$

$$f(\theta) = \sqrt{\begin{array}{c} A_f^2 \sin^2\theta + B_f^2 \cos^2\theta + \\ A_f^2\sin^2\theta\dfrac{(-\cos\omega + h_2\sin\omega)^2}{h_3^2} + B_f^2\cos^2\theta\dfrac{(\sin\omega + h_2\cos\omega)^2}{h_3^2} + \\ 2A_f B_f \sin\theta\cos\theta\dfrac{(-\cos\omega + h_2\sin\omega)(\sin\omega + h_2\cos\omega)}{h_3^2} \end{array}}$$

(6) In order to calculate the coordinates of a point at which Ld becomes the designated distance $\overline{K_iM_i}$, a possible range of $\theta_Q$ as a candidate value of $\theta_Q$ is divided by an appropriate division number T, Ld is approximately calculated for each of the candidate values using the mensuration by parts using the extended midpoint rule, and the candidate value of $\theta_Q$ at which the calculated value of Ld becomes closest to the designated distance $\overline{K_iM_i}$ is adopted.

Candidate value of $\theta_Q$ $$\theta_S + \dfrac{\overline{K_iM_i}}{|\overrightarrow{OQ}_{max}|}, \theta_S + \dfrac{\overline{K_iM_i}}{|\overrightarrow{OQ}_{max}|} + v, \theta_S + v \cdot 2,$$

$$\ldots, \theta_S + \dfrac{\overline{K_iM_i}}{|\overrightarrow{OQ}_{max}|} + v \cdot (T-1), \theta_S + \dfrac{\overline{K_iM_i}}{|\overrightarrow{OQ}_{min}|}$$

Here, $v = \dfrac{1}{T}\left(\dfrac{\overline{K_iM_i}}{|\overrightarrow{OQ}_{min}|} - \dfrac{\overline{K_iM_i}}{|\overrightarrow{OQ}_{max}|}\right)$ As described above, the coordinates of the point $M_i$, at which the distance from the reference point $K_i$ becomes (expression 5), on the curve $L_2$ are calculated.

(2) In the case of condition 2 (in the case of expression 7)

$(X_{Ki} \neq 0, Y_{Ki} = 0, Z_{Ki} \neq 0)$ (expression 7)

(i) Find the expression of the tangential line $L_1$ at the point $K_i$, which is included in the cross section $S_1$, to the ellipsoid.

The point $K_i$ is expressed as $K_i(X_{Ki}\ 0\ Z_{Ki}) = (Rvx \cdot \cos\phi_{Ki}\ 0\ Rvz \cdot \sin\phi_{Ki})$ using the polar coordinates.

Figure 26:
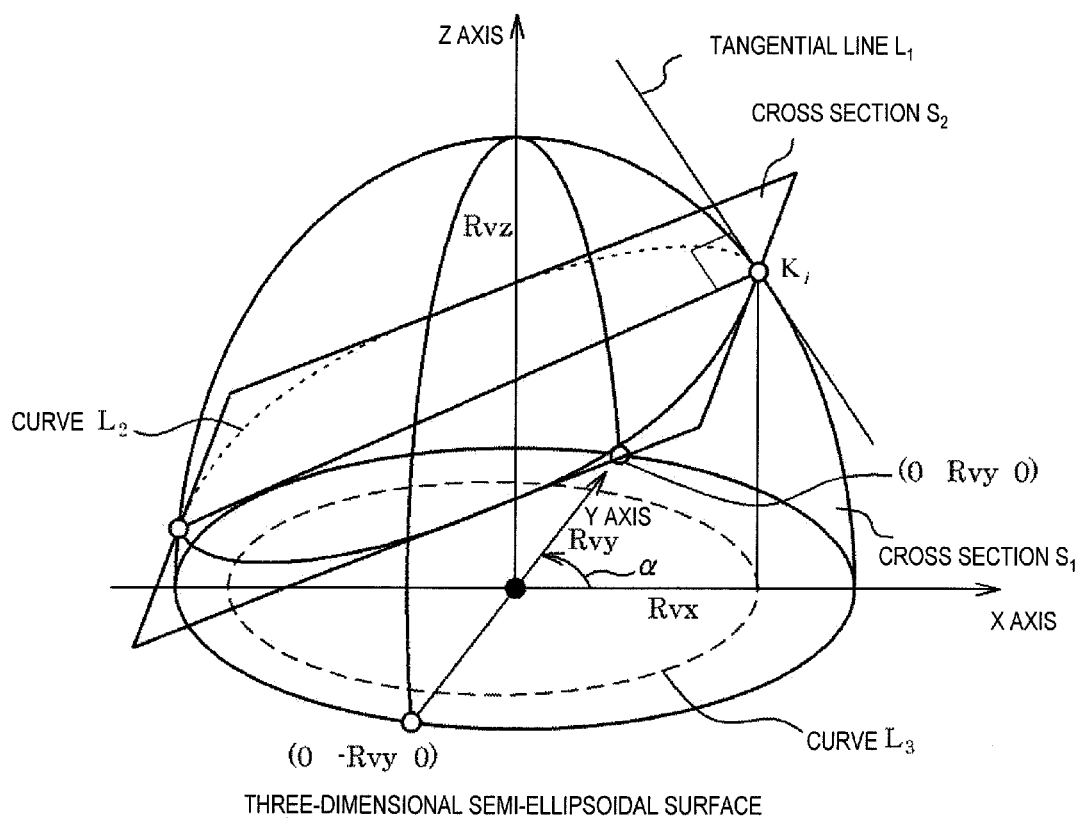
FIG. 26 is a view for explaining a calculation method of expressions of a cross section and a straight line on the three-dimensional semi-ellipsoid and a curve in condition 2.
Figure 27:
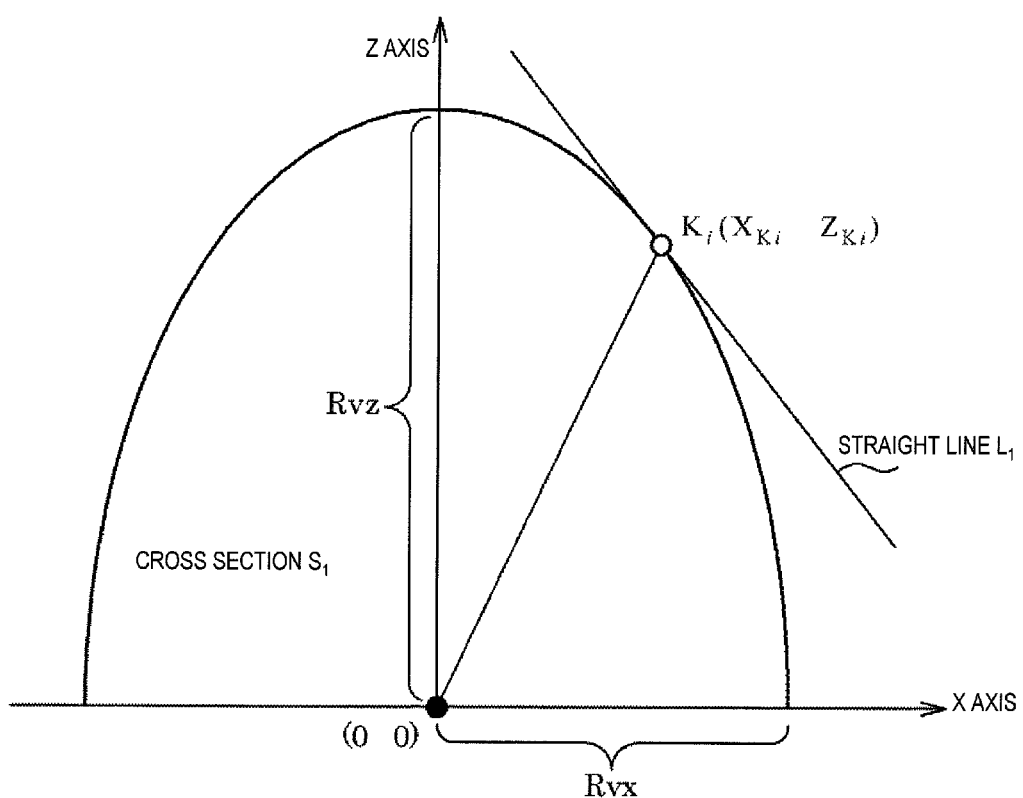
FIG. 27 is a view for explaining a calculation method of the expression of a straight line L1 on a cross section S1 in condition 2.

As shown in FIG. 27, the cross section $S_1$ shown in FIG. 26 becomes a semi-elliptical shape with radii of Rvx and Rvz.

In the coordinate system on the cross section $S_1$, the point $K_i$ is expressed as $(X_{Ki}\ Z_{Ki})$.

The straight line $L_1$ is calculated as follows.

$$\dfrac{X \cdot X_{Ki}}{Rvx^2} + \dfrac{Z \cdot Z_{Ki}}{Rvz^2} = 1$$

$$Z = -\dfrac{Rvz^2 X_{Ki}}{Rvx^2 Z_{Ki}} Y + \dfrac{Rvz^2}{Z_{Ki}}$$

(ii) Find the expression of the cross section $S_2$.

As shown in FIG. 26, as a plane perpendicular to the straight line $L_1$, the cross section $S_2$ is calculated as follows.

Cross section $S_2(X - X_{Ki}) - h_3(Z - Z_{Ki}) = 0$

Here, $$h_3 = \frac{Rvz^2 X_{Ki}}{Rvx^2 Z_{Ki}}$$

(iii) Find the expression of the curve $L_2$.
The expression of the ellipsoid is as follows.

$$\frac{X^2}{Rvx^2} + \frac{Y^2}{Rvy^2} + \frac{Z^2}{Rvz^2} = 1$$

The following expression is obtained by changing the expression of the cross section $S_2$.

$$Z = \frac{X - X_{Ki} + h_3 \cdot Z_{Ki}}{h_3}$$

The expression of the cross section $S_2$ is substituted into the expression of the ellipsoid to find a cross-sectional line formed by the line of intersection of the cross section $S_2$ and the ellipsoid.

$$\frac{X^2}{Rvx^2} + \frac{Y^2}{Rvy^2} + \frac{\left(\frac{X - X_{Ki} + h_3 \cdot Z_{Ki}}{h_3}\right)^2}{Rvz^2} = 1$$

After changing the above expression, the following expression is obtained. The following expression indicates a curve $L_3$ which is defined by projecting the curve $L_2$ on the XY plane, and is shown in FIGS. 23 and 25.

$$\frac{(X - x_0)^2}{A_f^2} + \frac{Y^2}{B_f^2} = 1$$

$$m_1 = \frac{Rvz^2 \cdot h_3^2}{Rvx^2} + 1 \quad m_2 = \frac{Rvz^2 + h_3^2}{Rvy^2}$$

$$m_3 = 2(X_1 - h_3 \cdot Z_1) \quad m_4 = (X_1 - h_3 \cdot Z_1)^2 - Rvz^2 \cdot h_3^2$$

$$m_5 = -m_4 + \frac{m_3^2}{4m_1}$$

$$A_f = \sqrt{\frac{m_5}{m_1}}, \quad B_f = \sqrt{\frac{m_5}{m_2}}$$

$$x_0 = \frac{m_3}{2m_1}$$

Using the above, the arbitrary point Q on the curve $L_2$ is expressed as follows using the parameter $\theta_Q$.

$$\begin{pmatrix} X_Q \\ Y_Q \\ Z_Q \end{pmatrix} = \begin{pmatrix} A_f \cos\theta_Q + x_0 \\ B_f \sin\theta_Q \\ \frac{A_f \cos\theta_Q + x_0 - X_1 + h_3 \cdot Z_1}{h_3} \end{pmatrix}$$

(iv) Find a point, at which the distance from the reference point $K_i$ becomes (expression 5), on the curve $L_2$.
(1) A parameter $\theta_s$ in the expression of the coordinates of the point $K_i$ on the curve $L_2$ is calculated.

$$\begin{pmatrix} X_{Ki} \\ 0 \\ Z_{Ki} \end{pmatrix} = \begin{pmatrix} A_f \cos\theta_S + x_0 \\ B_f \sin\theta_S \\ \frac{A_f \cos\theta_S + x_0 - X_1 + h_3 \cdot Z_1}{h_3} \end{pmatrix}$$

In the case of $X_{Ki} - x_0 \geq 0$, $\theta_s = 0$
In the case of $X_{Ki} - x_0 < 0$, $\theta_s = \pi$ (2) Coordinates of a point $O_2$ obtained by projecting the central point of the curve $L_3$ to the cross section $S_2$ and coordinates of two points $J_1$ and $J_2$ on the curve $L_2$ are calculated, and $|\overrightarrow{O_2 J_1}|$, $|\overrightarrow{O_2 J_2}|$, and $\overrightarrow{O_2 J_1} \cdot \overrightarrow{O_2 J_2}$ are calculated.

Point $O_2 \left( x_0 \quad 0 \quad \frac{x_0 - X_{Ki} + h_3 \cdot Z_{Ki}}{h_3} \right)$ Point $J_1 \left( A_f + x_0 \quad 0 \quad \frac{A_f + x_0 - X_{Ki} + h_3 \cdot Z_{Ki}}{h_3} \right)$ Point $J_2 \left( x_0 \quad B_f \quad \frac{x_0 - X_{Ki} + h_3 \cdot Z_{Ki}}{h_3} \right)$ $$|\overrightarrow{O_2 J_1}| = A_f \sqrt{1 + \frac{1}{h_3^2}}, \quad |\overrightarrow{O_2 J_2}| = B_f$$

$$\overrightarrow{O_2 J_1} \cdot \overrightarrow{O_2 J_2} = 0$$

(3) The minimum value $|\overrightarrow{O_2 Q}|_{min}$ and the maximum value $|\overrightarrow{O_2 Q}|_{max}$ of $|\overrightarrow{O_2 Q}|$ are calculated.

$$|\overrightarrow{O_2 Q}|_{min} = \min(|\overrightarrow{O_2 J_1}| \cdot |\overrightarrow{O_2 J_2}|)$$

$$|\overrightarrow{O_2 Q}|_{max} = \max(|\overrightarrow{O_2 J_1}| \cdot |\overrightarrow{O_2 J_2}|)$$

Figure 28:
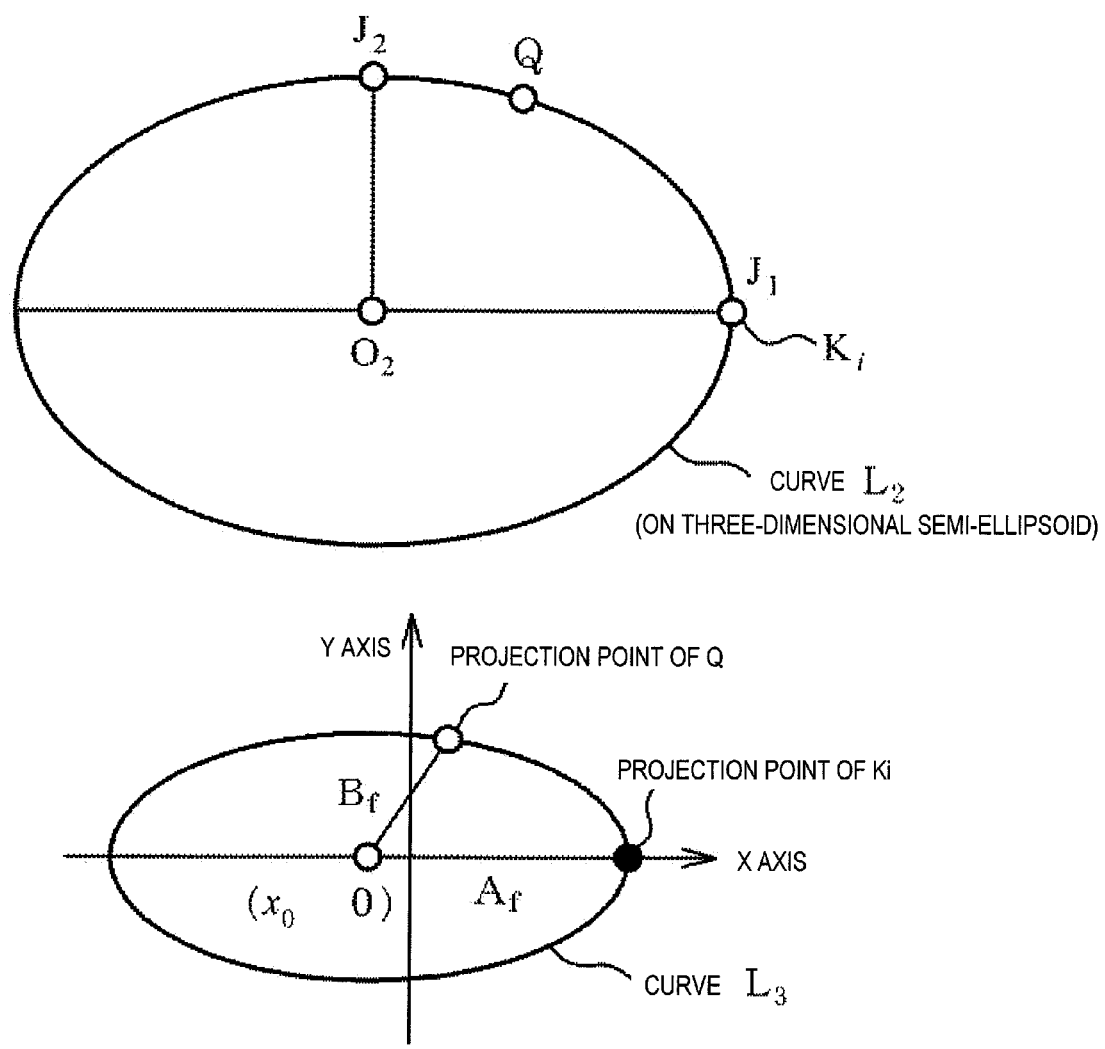
FIG. 28 is a view for explaining a calculation method of curves L2 and L3 in condition 2.

(4) $\theta_Q$ obtained when the length Ld of an arc on the curve $L_2$ between the point $K_i$ and the point Q becomes a designated distance $\overline{K_i M_i}$ in the counterclockwise direction in FIG. 28 is in the following range (Also in the case where it becomes the designated distance $\overline{K_i M_i}$ in the clockwise direction, it can be calculated similarly. Accordingly, the explanation is omitted).

$$\theta_S + \frac{\overline{K_i M_i}}{|\overrightarrow{O_2 Q_{max}}|} \leq \theta_Q \leq \theta_S + \frac{\overline{K_i M_i}}{|\overrightarrow{O_2 Q_{min}}|}$$

(5) The length Ld of the arc on the curve $L_2$ between the point $K_i$ and the point Q can be calculated according to the following expression.

$$Ld = \left| \int_{\theta_S}^{\theta_Q} \sqrt{\left(\frac{dX}{d\theta}\right)^2 + \left(\frac{dY}{d\theta}\right)^2 + \left(\frac{dZ}{d\theta}\right)^2} \, d\theta \right|$$

$$Ld = \left| \int_{\theta_S}^{\theta_Q} \sqrt{A_f^2 \left(1 + \frac{1}{h_3^2}\right) \sin^2\theta + B_f^2 \cos^2\theta} \, d\theta \right|$$

By this definite integral, it is not possible acquire a solution in a deductive way. Therefore, the solution can be approximately calculated by mensuration by parts using the extended midpoint rule. In the extended midpoint rule, the calculation is performed as follows using an appropriate division number N.

$$Ld = \sum_{j=0}^{N-1} f\left(\theta_{j+\frac{1}{2}}\right) \times h$$

$$\theta_{j+\frac{1}{2}} = \left(j + \frac{1}{2}\right) \times \frac{\theta_Q - \theta_S}{N} + \theta_S \quad (j = 0 \text{ to } N-1)$$

$$f(\theta) = \sqrt{A_f^2\left(1 + \frac{1}{h_3^2}\right)\sin^2\theta + B_f^2\cos^2\theta}$$

(6) In order to calculate the coordinates of a point at which Ld becomes the designated distance $\overline{K_iM_i}$, a possible range of $\theta_Q$ as a candidate value of $\theta_Q$ is divided by an appropriate division number T, Ld is approximately calculated for each of the candidate values using the mensuration by parts using the extended midpoint rule, and the candidate value of $\theta_Q$ at which the calculated value of Ld becomes closest to the designated distance $\overline{K_iM_i}$ is adopted.

Candidate value of $\theta_Q$ $$\theta_S + \frac{\overline{K_iM_i}}{|\overrightarrow{OQ_{max}}|}, \theta_S + \frac{\overline{K_iM_i}}{|\overrightarrow{OQ_{max}}|} + v,$$

$$\theta_S + v \cdot 2, \ldots, \theta_S + \frac{\overline{K_iM_i}}{|\overrightarrow{OQ_{max}}|} + v \cdot (T-1),$$

$$\theta_S + \frac{\overline{K_iM_i}}{|\overrightarrow{OQ_{min}}|}$$

Here, $$v = \frac{1}{T}\left(\frac{\overline{K_iM_i}}{|\overrightarrow{OQ_{min}}|} - \frac{\overline{K_iM_i}}{|\overrightarrow{OQ_{max}}|}\right)$$

As described above, the coordinates of the point $M_i$, at which the distance from the reference point $K_i$ becomes (expression 5), on the curve $L_2$ are calculated.

(3) In the case of condition 3 ($Z_{Ki}=0$)
(i) Find the expression of the tangential line $L_1$ at the point $K_i$, which is included in the cross section $S_1$, to the ellipsoid.

Tangential line $L_1 X = X_1, Y = Y_i$ (ii) Find the expression of the cross section $S_2$. Since the bottom surface of the semi-ellipsoid is the cross section $S_2$, expression of the cross section $S_2$ is $Z=0$.

(iii) Find the expression of the curve $L_2$.
Since an ellipse of the bottom surface of the semi-ellipsoid is the curve $L_2$, expression of curve $L_2$ is (expression 8).

$$\frac{X^2}{Rvx^2} + \frac{Y^2}{Rvy^2} = 1 \quad \text{(expression 8)}$$

(iv) Find a point, at which the distance from the reference point $K_i$ becomes (expression 5), on the curve $L_2$.

Since the curve $L_2$ is an ellipse, the coordinate value of the point, at which the distance from the reference point $K_i$ becomes (expression 5), on the curve $L_2$ is calculated using the "calculation of the point coordinates at which the length of an ellipse arc becomes a designated distance" method described previously.

(4) In the case of condition 4

($X_{Ki}=0, Y_{Ki}\neq 0, Z_{Ki}\neq 0$)

(i) Find the expression of the tangential line $L_1$ at the point $K_i$, which is included in the cross section $S_1$, to the ellipsoid.

The point $K_i$ is expressed as $K_i(0\ Y_{Ki}\ Z_{Ki}) = (0\ Rvy \cdot \cos\phi_{Ki}\ Rvz \cdot \sin\phi_{Ki})$ using the polar coordinates.

Figure 29:
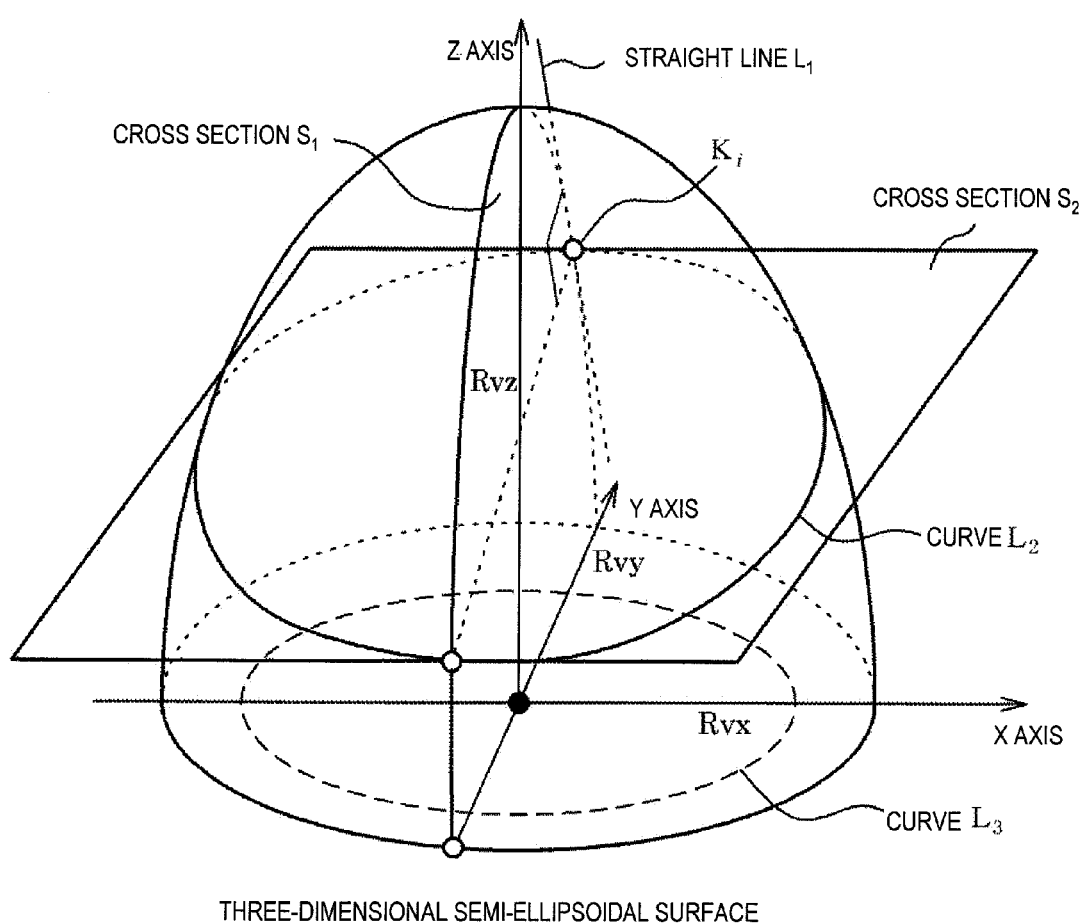
FIG. 29 is a view for explaining a calculation method of expressions of a cross section and a straight line on the three-dimensional semi-ellipsoid and a curve in condition 4.
Figure 30:
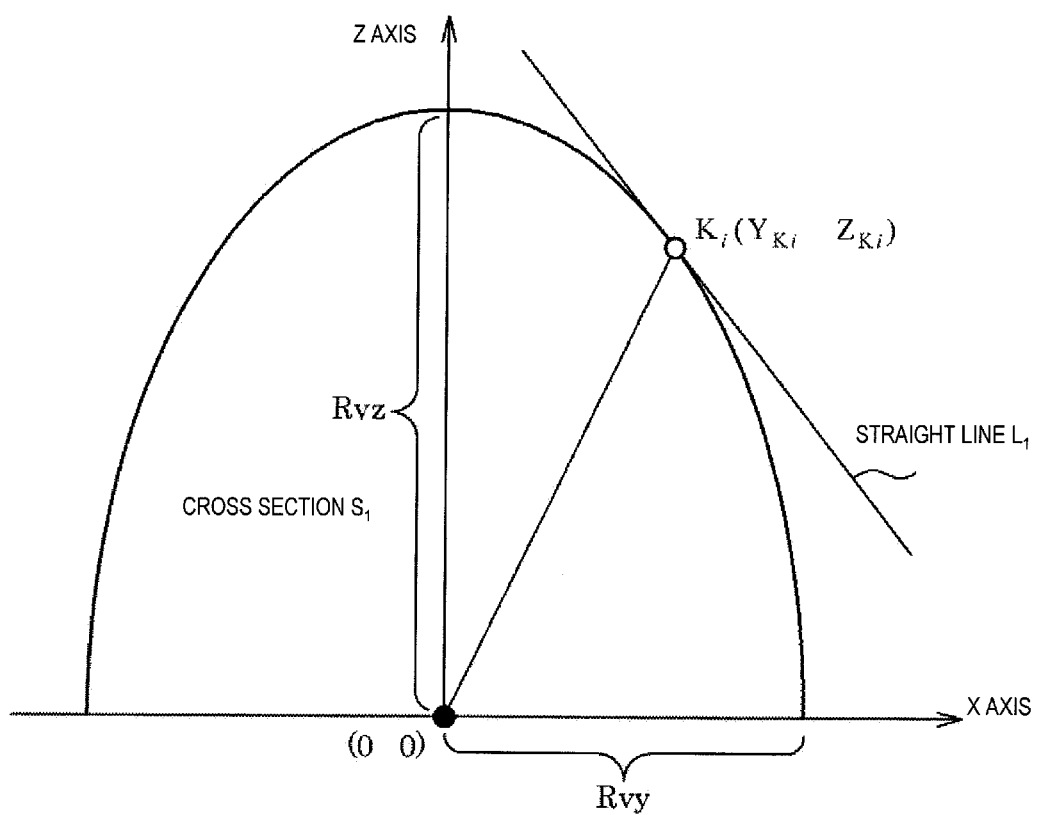
FIG. 30 is a view for explaining a calculation method of the expression of a straight line L1 on a cross section S1 in condition 4.

As shown in FIG. 30, the cross section $S_1$ shown in FIG. 29 becomes a semi-elliptical shape with radii of Rvy and Rvz.

In the coordinate system on the cross section $S_1$, the point $K_i$ is expressed as $(Y_{Ki}\ Z_{Ki})$.

The straight line $L_1$ is calculated as follows.

$$\frac{Y \cdot Y_{Ki}}{Rvy^2} + \frac{Z \cdot Z_{Ki}}{Rvz^2} = 1$$

$$Z = -\frac{Rvz^2}{Rvy^2}\frac{Y_{Ki}}{Z_{Ki}}Y + \frac{Rvz^2}{Z_{Ki}}$$

(ii) Find the expression of the cross section $S_2$.

As shown in FIG. 29, as a plane perpendicular to the straight line $L_1$, the cross section $S_2$ is calculated as follows.

Cross section $S_2(Y-Y_{Ki})-h_3(Z-Z_{Ki})=0$

Here, $$h_3 = \frac{Rvz^2 Y_{Ki}}{Rvy^2 Z_{Ki}}$$

(iii) Find the expression of the curve $L_2$.
The expression of the ellipsoid is as follows.

$$\frac{X^2}{Rvx^2} + \frac{Y^2}{Rvy^2} + \frac{Z^2}{Rvz^2} = 1$$

The following expression is obtained by changing the expression of the cross section $S_2$.

$$Z = \frac{Y - Y_{Ki} + h_3 \cdot Z_{Ki}}{h_3}$$

By substituting the expression of the cross section $S_2$ into the expression of the ellipsoid, a cross-sectional line formed as a line of intersection of the cross section $S_2$ and the ellipsoid is calculated.

$$\frac{X^2}{Rvx^2} + \frac{Y^2}{Rvy^2} + \frac{\left(\frac{Y - Y_{Ki} + h_3 \cdot Z_{Ki}}{h_3}\right)^2}{Rvz^2} = 1$$

After changing the above expression, the following expression is obtained. The following expression indicates a curve $L_3$ which is defined by projecting the curve $L_2$ on the XY plane, and is shown in FIGS. 23 and 25.

$$\frac{X^2}{A_f^2} + \frac{(Y-y_0)^2}{B_f^2} = 1$$

$$m_1 = \frac{Rvz^2 \cdot h_3^2}{Rvx^2} \quad m_2 = \frac{Rvz^2 \cdot h_3^2}{Rvy^2} + 1$$

$$m_3 = 2(Y_1 - h_3 \cdot Z_1) \quad m_4 = (Y_1 - h_3 \cdot Z_1)^2 - Rvz^2 \cdot h_3^2$$

$$m_5 = -m_4 + \frac{m_3^2}{4m_2}$$

-continued $$A_f = \sqrt{\frac{m_5}{m_1}}, B_f = \sqrt{\frac{m_5}{m_2}}$$

$$y_0 = \frac{m_3}{2m_2}$$

Using the above, the arbitrary point Q on the curve $L_2$ is expressed as follows using the parameter $\theta_Q$.

$$\begin{pmatrix} X_Q \\ Y_Q \\ Z_Q \end{pmatrix} = \begin{pmatrix} A_f \cos\theta_Q \\ B_f \sin\theta_Q + y_0 \\ \frac{B_f \sin\theta_Q + y_0 - Y_1 + h_3 \cdot Z_1}{h_3} \end{pmatrix}$$

(iv) Find a point, at which the distance from the reference point $K_i$ becomes (expression 5), on the curve $L_2$.

(1) A parameter $\theta_s$ in the expression of the coordinates of the point $K_i$ on the curve $L_2$ is calculated.

$$\begin{pmatrix} 0 \\ Y_{Ki} \\ Z_{Ki} \end{pmatrix} = \begin{pmatrix} A_f \cos\theta_S \\ B_f \sin\theta_S + y_0 \\ \frac{B_f \sin\theta_S + y_0 - Y_1 + h_3 \cdot Z_1}{h_3} \end{pmatrix}$$

In the case of $Y_{Ki} - y_0 \geq 0$, $$\theta_S = \frac{\pi}{2}$$

In the case of $Y_{Ki} - y_0 < 0$, $$\theta_S = -\frac{\pi}{2}$$

(2) Coordinates of a point $O_2$ obtained by projecting the central point of the curve $L_3$ to the cross section $S_2$ and coordinates of two points $J_1$ and $J_2$ on the curve $L_2$ are calculated, and $|\overrightarrow{O_2J_1}|$, $|\overrightarrow{O_2J_2}|$, and $\overrightarrow{O_2J_1} \cdot \overrightarrow{O_2J_2}$ are calculated.

Point $O_2 \left( 0 \quad y_0 \quad \frac{y_0 - Y_{Ki} + h_3 \cdot Z_{Ki}}{h_3} \right)$ Point $J_1 \left( A_f \quad y_0 \quad \frac{y_0 - Y_{Ki} + h_3 \cdot Z_{Ki}}{h_3} \right)$ Point $J_2 \left( 0 \quad B_f + y_0 \quad \frac{B_f + y_0 - Y_{Ki} + h_3 \cdot Z_{Ki}}{h_3} \right)$ $|\overrightarrow{O_2J_1}| = A_f$, $|\overrightarrow{O_2J_2}| = B_f \sqrt{1 + \frac{1}{h_3^2}}$ $\overrightarrow{O_2J_1} \cdot \overrightarrow{O_2J_2} = 0$ (3) The minimum value $|\overrightarrow{O_2Q}|_{min}$ and the maximum value $|\overrightarrow{O_2Q}|_{max}$ of $|\overrightarrow{O_2Q}|$ are calculated.

Figure 31:
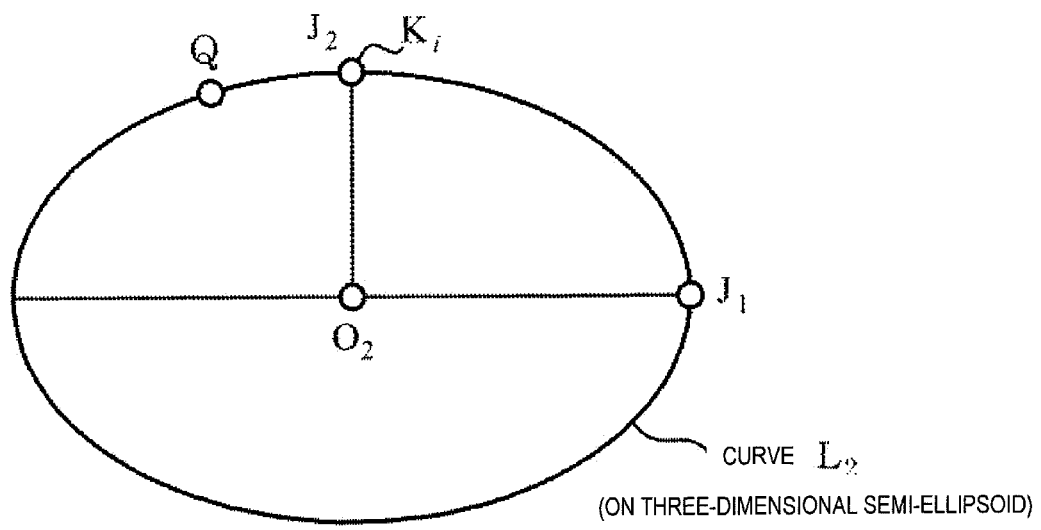
FIG. 31 is a view for explaining a calculation method of curves L2 and L3 in condition 4.
Figure 31:
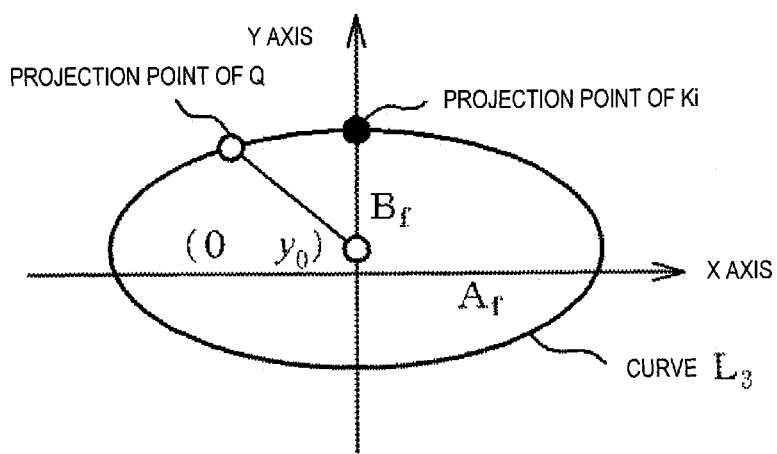

$|\overrightarrow{O_2Q}|_{min} = \min(|\overrightarrow{O_2J_1}|, |\overrightarrow{O_2J_2}|)$ $|\overrightarrow{O_2Q}|_{max} = \max(|\overrightarrow{O_2J_1}|, |\overrightarrow{O_2J_2}|)$ (4) $\theta_Q$ obtained when the length Ld of an arc on the curve $L_2$ between the point $K_i$ and the point Q becomes a designated distance $\overline{K_iM_i}$ in the counterclockwise direction in FIG. 31 is in the following range (Also in the case where it becomes designated distance $\overline{K_iM_i}$ in the clockwise direction, it can be calculated similarly. Accordingly, the explanation is omitted).

$$\theta_S + \frac{\overline{K_iM_i}}{|\overrightarrow{O_2Q_{max}}|} \leq \theta_Q \leq \theta_S + \frac{\overline{K_iM_i}}{|\overrightarrow{O_2Q_{min}}|}$$

(5) The length Ld of the arc on the curve $L_2$ between the point $K_i$ and the point Q can be calculated according to the following expression.

$$Ld = \left| \int_{\theta_S}^{\theta_Q} \sqrt{\left(\frac{dX}{d\theta}\right)^2 + \left(\frac{dY}{d\theta}\right)^2 + \left(\frac{dZ}{d\theta}\right)^2} \, d\theta \right|$$

$$Ld = \left| \int_{\theta_S}^{\theta_Q} \sqrt{A_f^2 \sin^2\theta + B_f^2 \left(1 + \frac{1}{h_3^2}\right) \cos^2\theta} \, d\theta \right|$$

By this definite integral, it is not possible to acquire a solution in a deductive way. Therefore, the solution can be approximately calculated by mensuration by parts using the extended midpoint rule. In the extended midpoint rule, the calculation is performed as follows using an appropriate division number N.

$$Ld = \sum_{j=0}^{N-1} f\left(\theta_{j+\frac{1}{2}}\right) \times h$$

$$\theta_{j+\frac{1}{2}} = \left(j + \frac{1}{2}\right) \times \frac{\theta_Q - \theta_S}{N} + \theta_S \quad (j = 0 \text{ to } N - 1)$$

$$f(\theta) = \sqrt{A_f^2 \sin^2\theta + B_f^2 \left(1 + \frac{1}{h_3^2}\right) \cos^2\theta}$$

(6) In order to calculate the coordinates of a point at which Ld becomes the designated distance $\overline{K_iM_i}$, a possible range of $\theta_Q$ as a candidate value of $\theta_Q$ is divided by an appropriate division number T, Ld is approximately calculated for each of the candidate values using the mensuration by parts using the extended midpoint rule, and the candidate value of $\theta_Q$ at which the calculated value of Ld becomes closest to the designated distance $\overline{K_iM_i}$ is adopted.

Candidate value of $\theta_Q$ $$\theta_S + \frac{\overline{K_iM_i}}{|\overrightarrow{OQ_{max}}|}, \theta_S + \frac{\overline{K_iM_i}}{|\overrightarrow{OQ_{max}}|} + v,$$

$$\theta_S + v \cdot 2, \ldots, \theta_S + \frac{\overline{K_iM_i}}{|\overrightarrow{OQ_{max}}|} + v \cdot (T - 1),$$

$$\theta_S + \frac{\overline{K_iM_i}}{|\overrightarrow{OQ_{min}}|}$$

Here, $$v = \frac{1}{T}\left(\frac{\overline{K_iM_i}}{|\overrightarrow{OQ_{min}}|} - \frac{\overline{K_iM_i}}{|\overrightarrow{OQ_{max}}|}\right)$$

As described above, the coordinates of the point $M_i$, at which the distance from the reference point $K_i$ becomes (expression 5), on the curve $L_2$ are calculated (5) In the case of condition 5

$$\left(X_{Ki} = 0, Y_{Ki} = 0, \alpha \neq \pm \frac{\pi}{2}\right)$$

(i) Find the coordinates of the point $Q_2$.
The coordinates of the point $Q_2$ shown in FIG. 32 can be set as ($Rvx \cdot \cos\theta_2$, $Rvy \cdot \sin\theta_2$, 0)
Here, $\theta_2$ is calculated as follows.

In the case of $$-\pi < \alpha < 0, \theta_2 = \arctan\left(\frac{Rvy}{Rvx}\tan\left(a + \frac{\pi}{2}\right)\right)$$

In the case of $$0 < \alpha < \frac{\pi}{2}, \theta_2 = \arctan\left(\frac{Rvy}{Rvx}\tan\left(a + \frac{\pi}{2}\right)\right) + \pi$$

In the case of $$\frac{\pi}{2} < \alpha < \pi, \theta_2 = \arctan\left(\frac{Rvy}{Rvx}\tan\left(a + \frac{\pi}{2}\right)\right) - \pi$$

(ii) Find the expression of the curve $L_2$.

Figure 32:
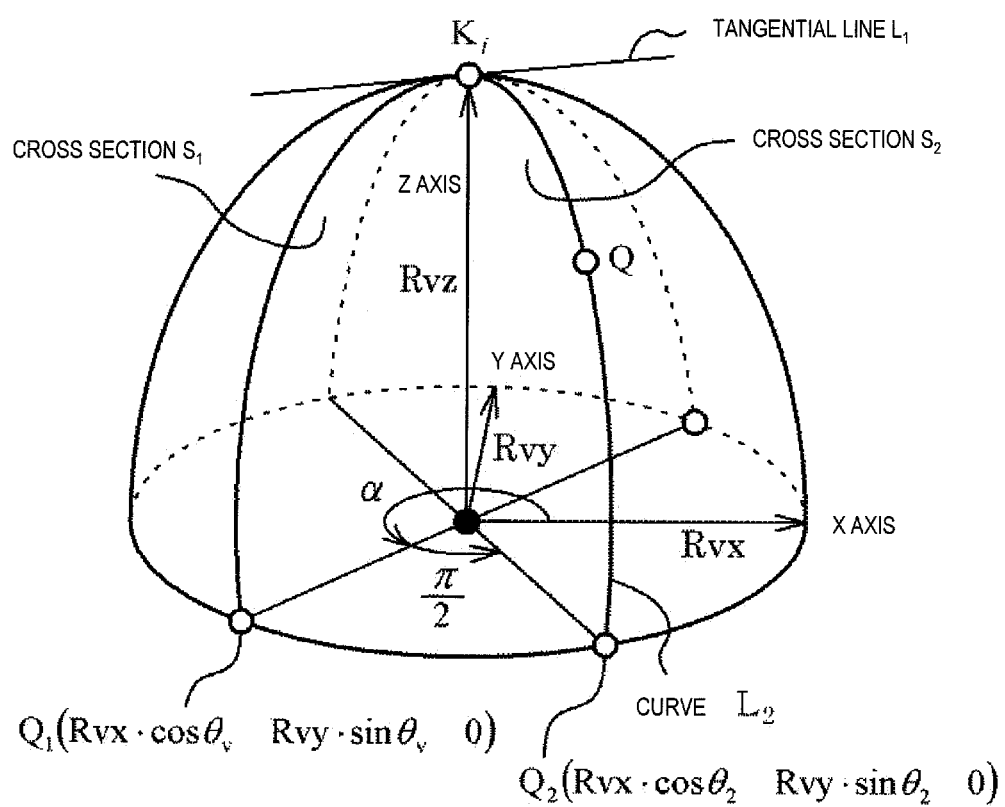
FIG. 32 is a view for explaining a calculation method of expressions of a cross section and a straight line on the three-dimensional semi-ellipsoid and a curve in condition 5.
Figure 33:
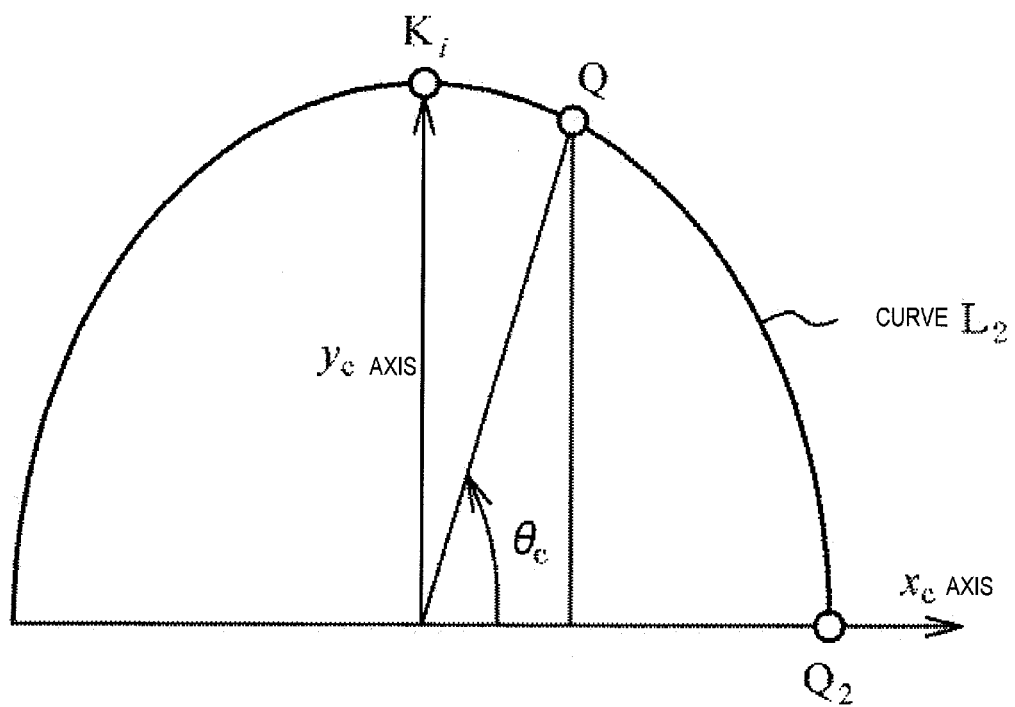
FIG. 33 is a view for explaining a straight line L2 on a cross section S2 in condition 5.

As shown in FIGS. 32 and 33, the curve $L_2$ is an ellipse with radii of ($\sqrt{Rvx^2\cos^2\theta_2 + Rvy^2\sin^2\theta_2}$) and Rvz on the cross section $S_2$.

In the $X_c Y_c$ coordinate system shown in FIG. 33, the expression of the curve $L_2$ is as follows.

$$\left(\frac{X_c^2}{\sqrt{Rvx^2\cos^2\theta_2 + Rvy^2\sin^2\theta_2}}\right) + \frac{Y_c^2}{Rvz^2} = 1$$

Accordingly, the coordinates of the point Q on the curve $L_2$ is expressed as follows using the angle of deflection $\theta_c$.

Point Q on the curve $L_2$ ($\sqrt{Rvx^2\cos^2\theta_2 + Rvy^2\sin^2\theta_2}\cos\theta_c$ Rvz·sin $\theta_c$)

(iii) The coordinates of the point Q on the curve $L_2$ in the ellipsoid are as follows.

$$\begin{pmatrix} \sqrt{Rvx^2\cos^2\theta_2 + Rvy^2\sin^2\theta_2} \cos\theta_c \cdot \cos\left(a + \frac{\pi}{2}\right) \\ \sqrt{Rvx^2\cos^2\theta_2 + Rvy^2\sin^2\theta_2} \cos\theta_c \cdot \sin\left(a + \frac{\pi}{2}\right) \\ Rvz \cdot \sin\theta_c \end{pmatrix}$$

(iv) Find a point, at which the distance from the reference point $K_i$ becomes (expression 5), on the curve $L_2$.

By calculating the point, at which the distance from the reference point $K_i$ becomes (expression 5), on the curve $L_2$ using the "calculation of the point coordinates at which the length of an ellipse arc becomes a designated distance" method described previously and calculating the angle of deflection $\theta_c$ of the point, the coordinate value of the point on the three-dimensional semi-ellipsoid is calculated.

(6) In the case of condition 6

$$\left(X_{Ki} = 0, Y_{Ki} = 0, \alpha = \pm\frac{\pi}{2}\right)$$

Figure 34:
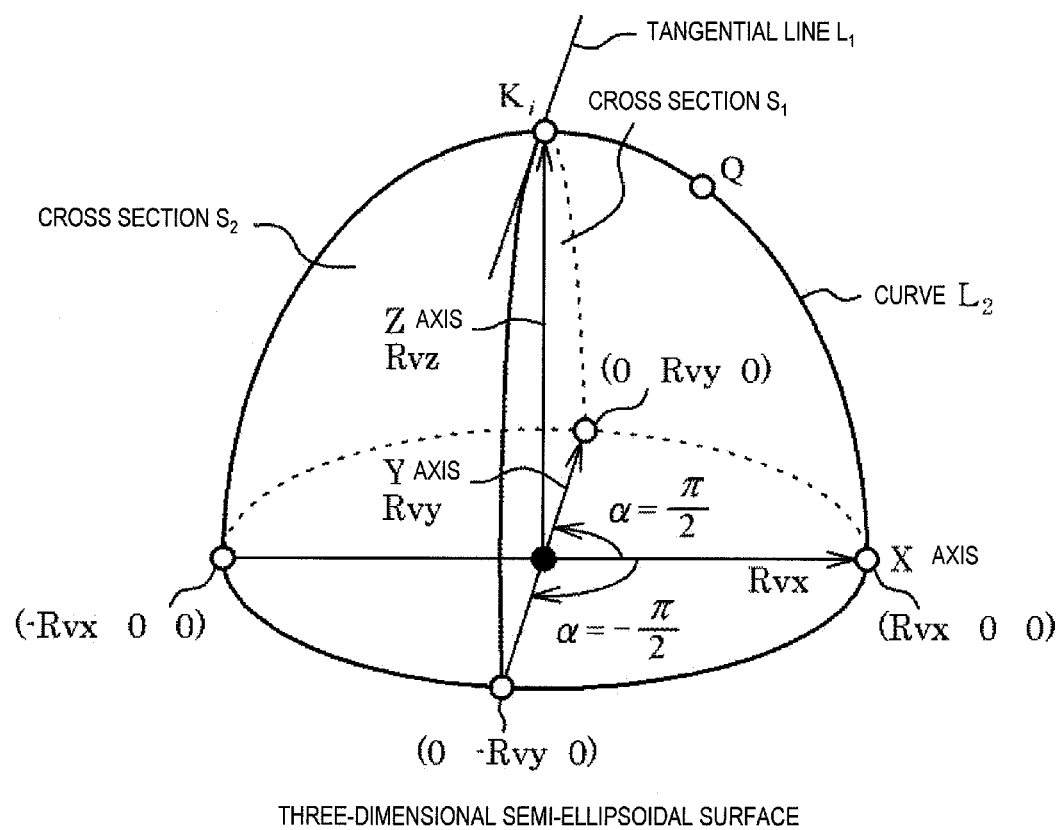
FIG. 34 is a view for explaining a calculation method of expressions of a cross section and a straight line on the three-dimensional semi-ellipsoid and a curve in condition 6.

As shown in FIG. 34, the cross section $S_2$ is an XZ coordinate plane.

Since the curve $L_2$ is an ellipse on the XZ coordinate plane, it is calculated as follows.

$$\frac{X^2}{Rvx^2} + \frac{Z^2}{Rvz^2} = 1$$

On the other hand, using the "calculation of the point coordinates at which the length of an ellipse arc becomes a designated distance" method described previously, the point, at which the distance from the reference point $K_i$ becomes (expression 5), on the curve $L_2$ is calculated.

(6.2. In the Case where the Shape Disposed on a Three-Dimensional Spherical Surface is Used)

Next, the case is assumed in which the shape disposed on a three-dimensional spherical surface is used as probe shape information.

Figure 35:
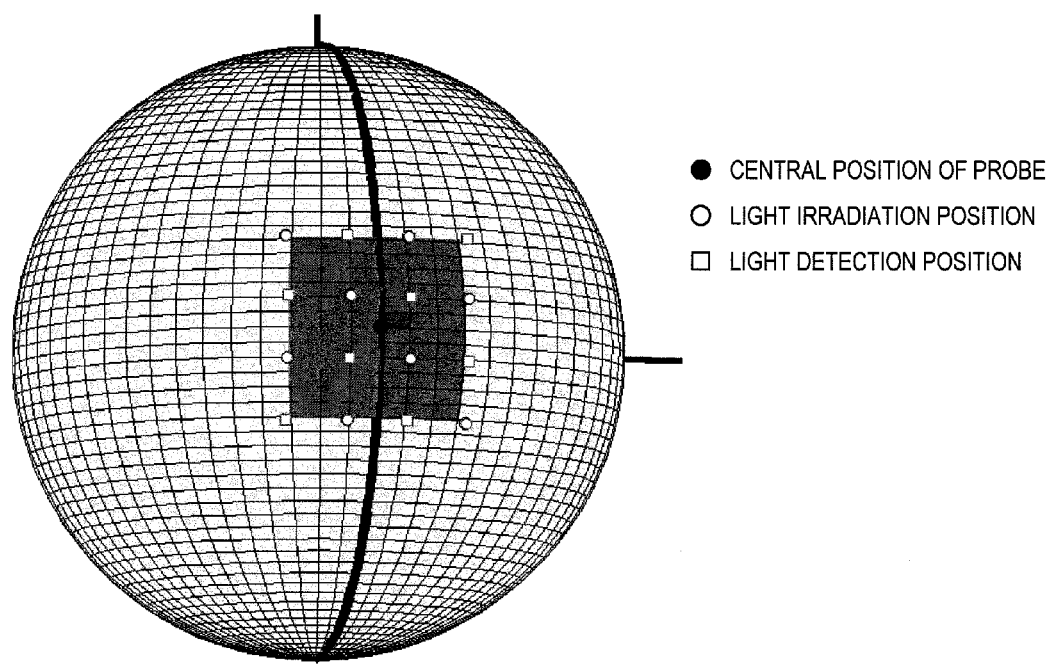
FIG. 35 is a view for explaining the shape of a probe disposed on the three-dimensional spherical surface.

The radius of a three-dimensional sphere is set to Rs. The central point of a probe is set to P (Rs 0 0). For example, it is assumed that the shape information shown in FIG. 35 is used as the probe shape information. A light irradiation position and a light detection position are disposed on the three-dimensional spherical surface with the x axis on three dimensions as the center. The coordinate points of light irradiation positions and light detection positions of N points on three dimensions are set to $M_1(x_1\,y_1\,z_1), \ldots, M_i(x_i\,y_i\,Z_i)\ldots, M_N(x_N\,y_N\,z_N)$ Then, rotation of the probe set on the two-dimensional head image is reflected in the probe shape information on the three-dimensional spherical surface.

The rotation is assumed to be performed with the x axis on three dimensions as the center. (refer to FIG. 36) The coordinate points of light irradiation positions and light detection positions of N points on three dimensions are set as follows, as shown in FIG. 36.

$$M_1(x_1, y_1\cos\theta_u - z_1\sin\theta_u, y_1\sin\theta_u + z_1\cos\theta_u)$$

$$M_i(x_i, y_i\cos\theta_u - z_i\sin\theta_u, y_i\sin\theta_u + z_i\cos\theta_u)$$

$$M_N(X_N, y_N\cos\theta_u - Z_N\sin\theta_u, y_N\sin\theta_u + Z_N\cos\theta_u)$$

At each point of the light irradiation position and the light detection position, a point which becomes the foot onto the reference point of the probe is calculated. These are set as reference points $K_1, \ldots K_i, \ldots, K_N$ with respect to each point of the light irradiation position and the light detection position. For example, for $M_i$, the reference point $K_i$ is calculated as follows.

$$K_i(\sqrt{R_s^2 - (y_i\sin\theta_u + z_i\cos\theta_u)^2}\,0\,y_i\sin\theta_u + z_i\cos\theta_u)$$

Moreover, on the three-dimensional spherical surface, an arc length (expression 2) between the central point of the probe and each reference point and an arc length (expression 3) between each reference point and each point of the light irradiation position and the light detection position are calculated. For example, (expression 4) and (expression 5) found for $M_i$ and the reference point $K_i$ are as follows.

Figure 37:
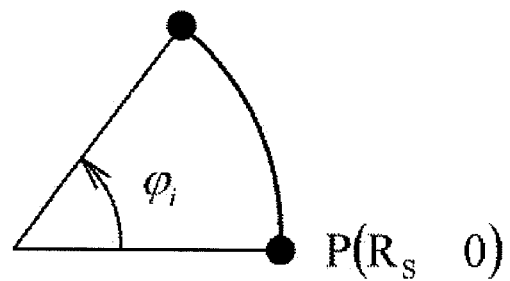
FIG. 37 is a view for explaining the relationship on the cross section parallel to the yz plane of a reference point Ki and a central point P of a probe on the three-dimensional spherical surface.

Since a cross section cut by the plane, which passes through $M_i$ and is parallel to the yz plane, is as shown in FIG. 37, the following expression is obtained.

$$\overline{PK_i} = |R_S \cdot \varphi_i|,$$

$$\varphi_i = \arccos\left(\frac{\sqrt{R_S^2 - (y_i\sin\theta_u + z_i\cos\theta_u)^2}}{R_S}\right)$$

Figure 38:
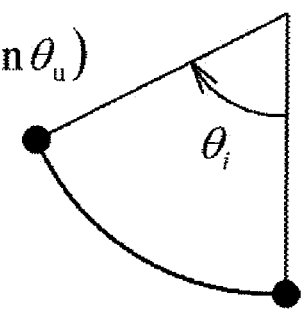
FIG. 38 is a view for explaining the relationship on the cross section parallel to the xy plane of a light irradiation position and light detection position Mi and a reference point Ki of a probe on the three-dimensional spherical surface.

Since a cross section cut by the plane, which passes through $M_i$ and is parallel to the xy plane, is as shown in FIG. 38, the following expression is obtained.

$$\overline{K_iM_i} = \left|\sqrt{R_S^2 - (y_i\sin\theta_u + z_i\cos\theta_u)^2} \cdot \theta_i\right|,$$

$$\theta_i = \arccos\left(\frac{x_i}{\sqrt{R_S^2 - (y_i\sin\theta_u + z_i\cos\theta_u)^2}}\right)$$

Using the arc length (expression 2) from the central point of the probe to the reference point and the arc length (expression 3) from the reference point to each point of the light irradiation position and the light detection position as probe shape information, the coordinate positions of the light irradiation position and the light detection position on the three-dimensional elliptical hemisphere can be calculated, similar to the case where the shape on the two-dimensional plane is used.

(7. Display Function of an Electroencephalographic Electrode Position)

In the present embodiment, using the coordinate transformation processing A, B, C, and D (S2020, 52040, S2060, S2100), it is possible to display an electroencephalographic electrode position on a two-dimensional head image, a two-dimensional circle image, a three-dimensional hemispherical surface, a three-dimensional semi-ellipsoidal surface, and a three-dimensional head image. Hereinafter, the display function of the electroencephalographic electrode position will be described using FIGS. 39 and 40 (40A, 40B, and 40C).

Figure 39:
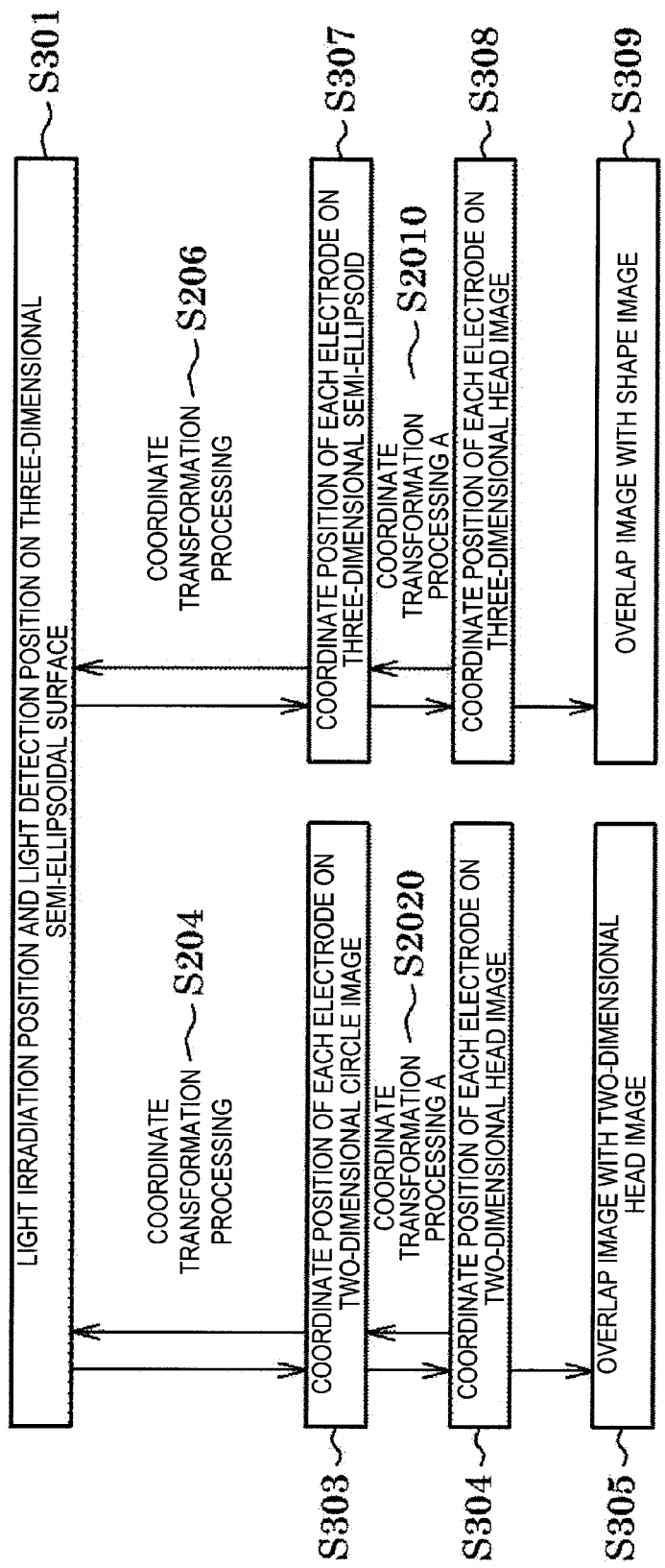
FIG. 39 is a view for explaining the flow chart of application of the present invention to a display function of the electroencephalographic electrode position.
Figure 40A:
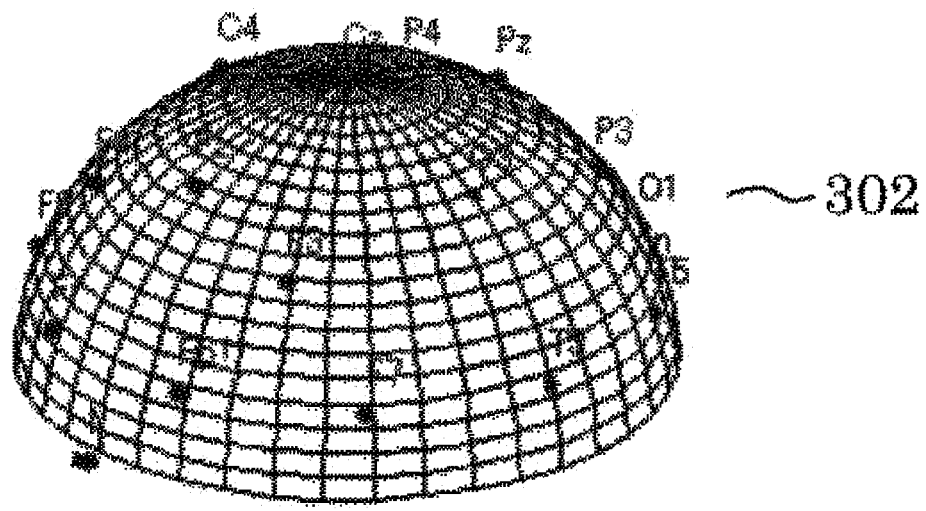
FIG. 40A is a view showing a result presented after calculating the coordinate position of each electrode on the three-dimensional hemisphere in the embodiment of FIG. 39.

FIG. 39 shows a flow chart of the display function of the electroencephalographic electrode position.

As the electroencephalographic electrode position, for example, a 10-20 electrode arrangement method is generally known. Details of the 10-20 electrode arrangement method are disclosed, for example, in Non-patent Document 1 (new clinical examination technician lecture 7, clinical physiology (third edition), Igaku-Shoin Ltd., pp. 174-176) and the like. In the present embodiment, this 10-20 electrode arrangement method is used. According to the defined arrangement method, the coordinate position (301) of each electrode on the three-dimensional hemisphere is calculated. The calculated result is like 302 of FIG. 40A.

The coordinate position (303) of each electrode on a two-dimensional circle image can be obtained by performing the coordinate transformation processing B (S2040) on the coordinate position (301) of each electrode on the three-dimensional hemisphere.

In addition, the coordinate position (305) of each electrode on a two-dimensional head image can be obtained by performing the coordinate transformation processing A (S2020) on the coordinate position (303) of each electrode on the two-dimensional circle image.

Figure 40B:
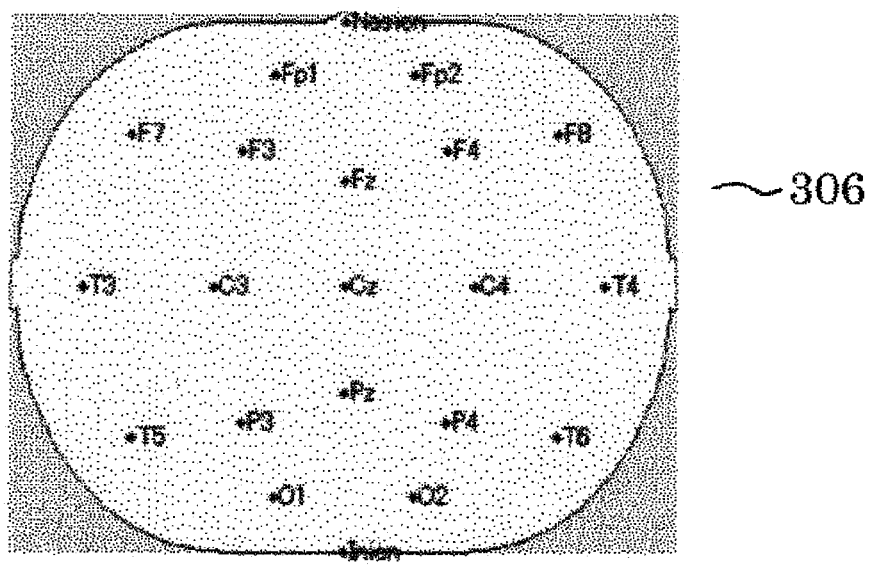
FIG. 40B is a view showing a result presented after obtaining an overlap image with a two-dimensional head image using the coordinate position of each electrode on a two-dimensional head image in the embodiment of FIG. 39.

Using the coordinate position (305) of each electrode on the two-dimensional head image, an overlap image (306) with the two-dimensional head image 2012 can be obtained and presented as shown in FIG. 40B.

In addition, the coordinate position (307) of each electrode on a three-dimensional semi-ellipsoid can be obtained by performing the coordinate transformation processing C (S2060) on the coordinate position (301) of each electrode on the three-dimensional hemisphere. In addition, the coordinate position (308) of each electrode on a three-dimensional head image 3100 can be obtained by performing the coordinate transformation processing D (S2080) on the coordinate position (307) of each electrode on the three-dimensional semi-ellipsoid.

Figure 40C:
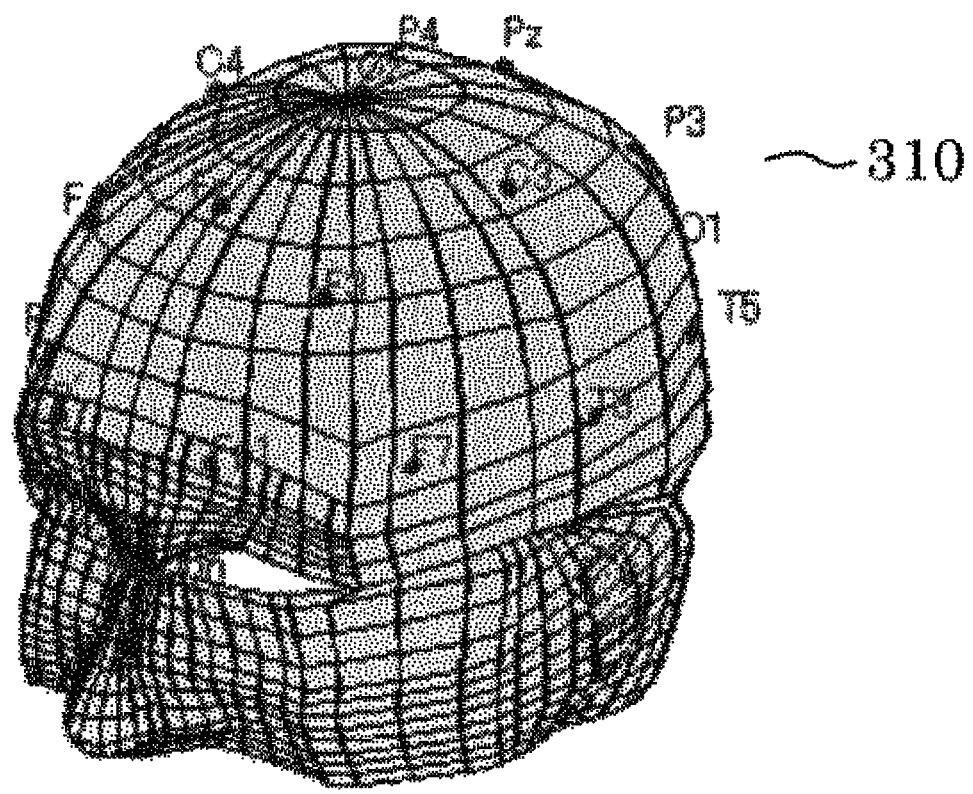
FIG. 40C is a view showing a result presented after obtaining an overlap image with a shape image using the coordinate position of each electrode on a three-dimensional head image in the embodiment of FIG. 39.

Using the coordinate position (308) of each electrode on the obtained three-dimensional head image, an overlap image (310) with the shape head can be obtained and presented as shown in FIG. 40C.

In addition, using the calculation result on each of the above-described images (the three-dimensional head image, the three-dimensional semi-ellipsoidal image, the three-dimensional hemispherical image, the two-dimensional circle image, and the two-dimensional head image), it is also possible to display the electroencephalographic electrode position and the biological light measurement result so as to overlap each other.

REFERENCE SIGNS LIST

100: biological light measurement device
101: light source unit
102: light measurement unit
103: control unit
104: semiconductor laser
105: optical module
106: optical fiber
107: subject body
108: probe holder
109: optical fiber for detection
110: photoelectric conversion element
111: lock-in amplifier
112: A/D converter
113: signal processing unit
114: display unit
115: storage unit
116: input/output unit
201: head shape data selecting section
202: probe position easy-input unit
203: coordinate transformation section
204: two-dimensional coordinate to three-dimensional coordinate transformation section
205: three-dimensional coordinate to two-dimensional coordinate transformation section
206: stimulus presenting section
207: topographic image generating section based on a light irradiation position
208: overlap processing section of a topographic image and the head shape
209: overlap display section of a topographic image and the head shape
2011: operation screen
2012: two-dimensional head image
2013: two-dimensional probe
3100: three-dimensional head image.

The invention claimed is:

1. A biological light measurement device including a light source unit that irradiates near-infrared light, a two-dimensional probe that measures a transmitted light intensity of the near-infrared light at two-dimensional measurement points of a subject body and outputs a signal corresponding to the transmitted light intensity at each measurement point as measurement data for every measurement channel, a signal processing unit that processes the measurement data of the two-dimensional probe to be imaged, and a display unit that displays the imaged measurement data, the biological light measurement device comprising:

a storage unit that stores data regarding a head shape for display; and a control unit having a coordinate transformation section which performs coordinate transformation of positional information of the two-dimensional probe, which is set on a two-dimensional head image selected from the data regarding the head shape, in order to calculate a light irradiation position and a light detection position on a three-dimensional head image or the position of the measurement channel.

2. The biological light measurement device according to claim 1, wherein the display unit displays a shape corresponding to a three-dimensional probe which forms the light irradiation position and the light detection position in the two-dimensional probe or the measurement channel.

3. The biological light measurement device according to claim 1, wherein the coordinate transformation section calculates the light irradiation position and the light detection position or the calculation position of the measurement channel by sequentially repeating coordinate transformation processing between shapes approximated on the way from the two-dimensional head image to the three-dimensional head image.

4. The biological light measurement device according to claim 3,
wherein the coordinate transformation section calculates a coordinate position of a two-dimensional probe center on a two-dimensional circle image from the center coordinate position of the probe on the two-dimensional head image, calculates a coordinate position of the probe center on a three-dimensional hemispherical surface from the coordinate position of the probe center on the two-dimensional circle image, calculates a coordinate position of a three-dimensional probe center on a three-dimensional semi-ellipsoidal surface from the coordinate position of the probe center on the three-dimensional hemispherical surface, and calculates the light irradiation position and the light detection position on the three-dimensional semi-ellipsoidal surface 2 or the position of the measurement channel from the coordinate position of the three-dimensional probe center on the three-dimensional semi-ellipsoidal surface and sets the position as the light irradiation position and the light detection position on the three-dimensional head image or the calculation position of the measurement channel.

5. The biological light measurement device according to claim 3,
wherein the coordinate transformation section calculates a coordinate position of the probe center on a three-dimensional semi-ellipsoidal surface using coordinate transformation processing from the three-dimensional probe center on the three-dimensional head image when a position equivalent to the central point of the probe on the three-dimensional head image is set, calculates a coordinate position of the probe center on the three-dimensional hemispherical surface using coordinate transformation processing from the coordinate position of the three-dimensional probe center on the three-dimensional semi-ellipsoidal surface, calculates a coordinate position of the two-dimensional probe center on the two-dimensional circle image using coordinate transformation processing from the coordinate position of the probe center on the three-dimensional hemispherical surface, and calculates a position of the two-dimensional probe on the two-dimensional head image using coordinate transformation processing from the coordinate position of the probe center on the two-dimensional circle image.

6. The biological light measurement device according to claim 3,
wherein a plurality of electroencephalographic electrodes are provided in the measurement channel, and
the control unit acquires a coordinate position of each electrode on the two-dimensional circle image by performing coordinate transformation processing on a coordinate position of each electrode on the three-dimensional hemisphere, acquires a coordinate position of each electrode on the two-dimensional head image by performing coordinate transformation processing on a coordinate position of each electrode on the two-dimensional circle image, generates and displays an overlap image with the two-dimensional head image 2 using the coordinate position of each electrode on the two-dimensional head image, acquires a coordinate position of each electrode on the three-dimensional semi-ellipsoid by performing coordinate transformation processing on a coordinate position of each electrode on the three-dimensional hemisphere, acquires a coordinate position of each electrode on the three-dimensional head image by performing coordinate transformation processing on a coordinate position of each electrode on the three-dimensional semi-ellipsoid, and generates an overlap image with a shape image using the obtained coordinate position of each electrode on the three-dimensional head image and displays the overlap image on the display unit.

7. The biological light measurement device according to claim 6,
wherein the control unit displays the electroencephalographic electrode position and the biological light measurement result on the display unit so as to overlap each other, using a calculation result on each image of the three-dimensional head image, the three-dimensional semi-ellipsoidal image, the three-dimensional hemispherical image, the two-dimensional circle image, and the two-dimensional head image.

8. The biological light measurement device according to claim 1,
wherein the display unit simultaneously displays the two-dimensional probe and a corresponding three-dimensional head image and three-dimensional probe so as to overlap the two-dimensional head image.

9. The biological light measurement device according to claim 1, further comprising:
an overlap display unit that displays a processing result of the measurement data from the two-dimensional probe on the display unit so as to overlap the light irradiation position and the light detection position on the three-dimensional head image or the calculation position of the light measurement unit in the measurement channel.

10. A position display method of a light irradiation position and a light detection position or a measurement channel in a biological light measurement device including a light source unit that irradiates near-infrared light, a two-dimensional probe that measures a transmitted light intensity at two-dimensional measurement points of a subject body and outputs a signal corresponding to the transmitted light intensity at each measurement point as measurement data for every measurement channel, a signal processing unit that processes the measurement data of the two-dimensional probe to be imaged, a storage unit that stores data regarding a head shape for display, a display unit that displays the imaged measurement data, and a control unit having a coordinate transformation section, the position display method of a light irradiation position and a light detection position or a measurement channel in a biological light measurement device comprising:
displaying a two-dimensional head image and a two-dimensional probe on the display unit;
performing coordinate transformation of positional information of the two-dimensional probe on the two-dimensional head image displayed in order to calculate a three-dimensional probe and the light irradiation position and the light detection position on a three-dimensional head image or the position of the measurement channel; and
displaying the two-dimensional probe and the corresponding three-dimensional head image and three-dimensional probe on the display unit so as to overlap the two-dimensional head image.

11. The position display method of a light irradiation position and a light detection position or a measurement channel in a biological light measurement device according to claim 10,
wherein the light irradiation position and the light detection position of the three-dimensional probe or the calculation position of the measurement channel is calculated by sequentially repeating coordinate transformation processing between shapes approximated on the way from the two-dimensional head image to the three-dimensional head image, and a processing result of measurement data from the light measurement unit is displayed on the display unit so as to overlap the light irradiation position and the light detection position of the three-dimensional probe on the three-dimensional head image or the calculation position of the measurement channel.

* * * * *